(12) United States Patent
Choo

(10) Patent No.: US 8,802,376 B2
(45) Date of Patent: Aug. 12, 2014

(54) METHODS FOR IDENTIFYING CANDIDATE CYTOTOXIC ANTIBODY MOLECULES

(75) Inventor: Boon Hwa Andre Choo, Singapore (SG)

(73) Assignee: Agency for Science, Technology and Research, Connexis (SG)

( * ) Notice: Subject to any disclaimer, the term of this patent is extended or adjusted under 35 U.S.C. 154(b) by 12 days.

(21) Appl. No.: 13/811,068

(22) PCT Filed: Jul. 21, 2011

(86) PCT No.: PCT/SG2011/000262
§ 371 (c)(1),
(2), (4) Date: Jan. 18, 2013

(87) PCT Pub. No.: WO2012/011876
PCT Pub. Date: Jan. 26, 2012

(65) Prior Publication Data
US 2013/0115627 A1    May 9, 2013

Related U.S. Application Data

(60) Provisional application No. 61/366,193, filed on Jul. 21, 2010.

(51) Int. Cl.
*G01N 33/53* (2006.01)
(52) U.S. Cl.
USPC ............................................ 435/7.1; 436/518
(58) Field of Classification Search
None
See application file for complete search history.

(56) References Cited

FOREIGN PATENT DOCUMENTS

| WO | WO-2007102787 A1 | 9/2007 |
|---|---|---|
| WO | WO-2010033084 A1 | 3/2010 |

OTHER PUBLICATIONS

Blixt, O. et al., Printed Covalent Glycan Array for Ligand Profiling of Diverse Glycan Binding Proteins, PNAS, 101(49):17033-17038 (2004).
Chin, A.C.P. et al., Define and Serum-Free Media Support Undifferentiated Human Embryonic Stem Cell Growth, Stem Cells and Development, 19(6):753-764 (2010).
Choo, A.B. et al., Selection Against Undifferentiated Human Embryonic Stem Cells by a Cytotoxic Antibody Recognizing Podocalyxin-Like Protein-1, Stem Cells, 26:1454-1463 (2008).
Fredman, P. et al., A Monoclonal Antibody that Precipitates the Glycoprotein Receptor for Epidermal Growth Factor is Directed Against the Human Blood Group H Type 1 Antigen, The Journal of Biological Chemistry, 258(18):11206-11210 (1983).
Lee, J. et al., Adaptation of Hybridomas to Protein-Free Media Results in a Simplified Two-Step Immunoglobulin M Purification Process, Journal of Chromatography A, 1216:2683-2688 (2009).
Tan, H.L. et al., mAb 84, A Cytotoxic Antibody that Kills Undifferentiated Human Embryonic Stem Cells via Oncosis, Stem Cells, 27:1792-1801 (2009).
Tscheliessnig, A. et al., Engineering of a Two-Step Purification Strategy for a Panel of Monoclonal Immunoglobulin M Directed Against Undifferentiated Human Embryonic Stem Cells, Journal of Chromatography A, 1216:7851-7864 (2009).

*Primary Examiner* — Jacob Cheu
(74) *Attorney, Agent, or Firm* — Choate, Hall & Stewart, LLP; Charles E. Lyon

(57) ABSTRACT

The disclosure relates to methods for screening candidate antibody molecules which bind to podocalyxin-like protein (PODXL) and/or to undifferentiated pluripotent stem cells and particularly, although not exclusively, to methods for identifying candidate cytotoxic antibody molecules.

22 Claims, 51 Drawing Sheets

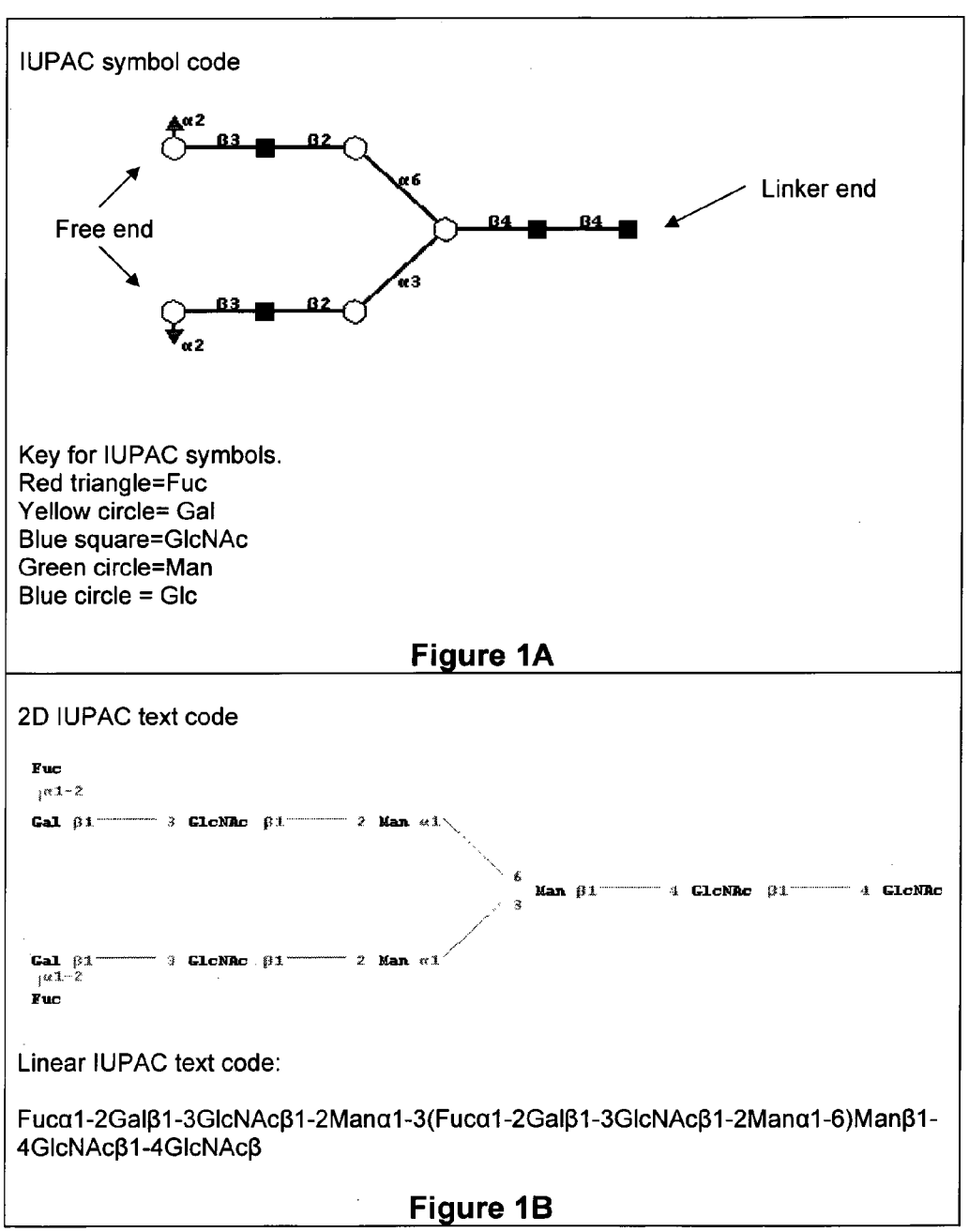

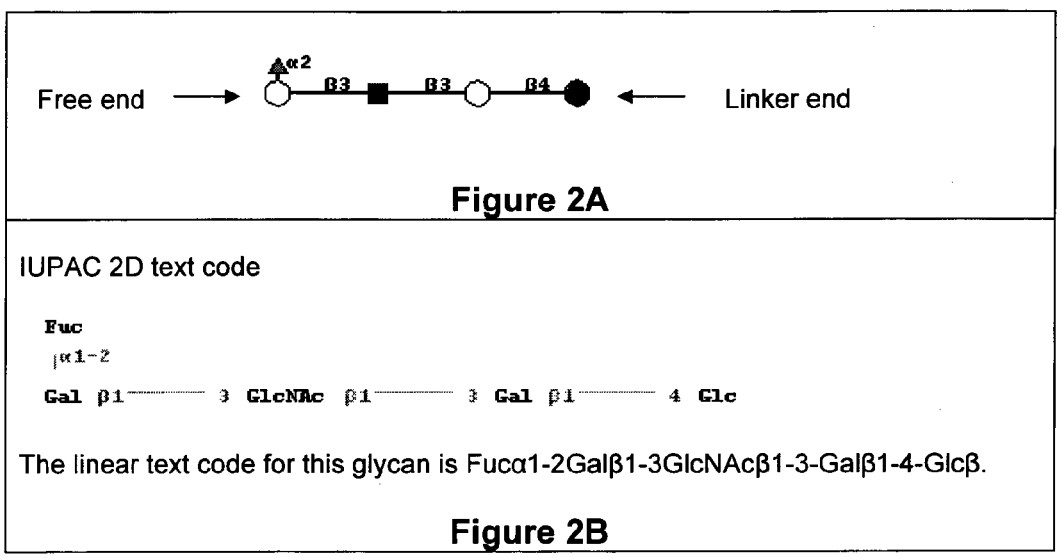

| Glycan number on array | Glycan Structure | Average | StDEV | SEM | % CV |
|---|---|---|---|---|---|
| 65 | Fucα1-2Galβ1-3GlcNAcβ1-3Galβ1-4Glcβ-Sp8 | 28216 | 7695 | 3848 | 27 |
| 458 | Neu5Acα2-6Galβ1-4GlcNAcβ1-6(Fucα1-2Galβ1-3GlcNAcβ1-3)Galβ-4Glc-Sp21 | 27746 | 1940 | 970 | 7 |
| 67 | Fucα1-2Galβ1-3GlcNAcβ-Sp0 | 26640 | 3034 | 1517 | 11 |
| 66 | Fucα1-2Galβ1-3GlcNAcβ1-3Galβ1-4Glcβ-Sp10 | 25696 | 2256 | 1128 | 9 |
| 421 | Fucα1-2Galβ1-3GlcNAcβ1-3GalNAc-Sp14 | 25670 | 2579 | 1289 | 10 |
| 428 | Fucα1-2Galβ1-3GlcNAcβ1-3(Galβ1-4GlcNAcβ1-6)Galβ1-4Glc-Sp21 | 24411 | 1909 | 954 | 8 |
| 367 | Fucα1-2Galβ1-3GlcNAcβ1-3(Galβ1-4(Fucα1-3)GlcNAcβ1-6)Galβ1-4Glc-Sp21 | 22081 | 3784 | 1892 | 17 |
| 68 | Fucα1-2Galβ1-3GlcNAcβ1-3GlcNAcβ-Sp8 | 21144 | 1104 | 552 | 5 |
| 359 | Fucα1-2Galβ1-3GlcNAcβ1-2Manα1-3(Fucα1-2Galβ1-3GlcNAcβ1-2Manα1-6)Manβ1-4GlcNAcβ-Sp20 | 18744 | 11882 | 5941 | 63 |
| 25 | [3OSO3]Galβ1-4[6OSO3]Glcβ-Sp0 | 92 | 37 | 18 | 40 |
| 341 | GlcNAcα1-4Galβ1-4GlcNAcβ1-3Galβ1-4GlcNAcβ-Sp0 | 44 | 15 | 8 | 34 |
| 377 | Neu5Acα2-3Galβ1-4(Fucα1-3)GlcNAcβ1-3GalNAcα-Sp14 | 35 | 15 | 7 | 43 |
| 401 | Galα1-4Galβ1-4GlcNAcβ1-2Manα1-3(Galα1-4Galβ1-4GlcNAcβ1-2Manα1-6)Manβ1-4GlcNAcβ1-4GlcNAcβ-Sp19 | 35 | 22 | 11 | 63 |
| 353 | Galβ1-3(Fucα1-4)GlcNAcβ1-2Manα1-3(Galβ1-3(Fucα1-4)GlcNAcβ1-2Manα1-6)Manβ1-4GlcNAcβ1-4GlcNAcβ-Sp19 | 30 | 19 | 9 | 62 |
| 364 | Galβ1-3(Fucα1-4)GlcNAcβ1-2Manα1-3(Galβ1-3(Fucα1-4)GlcNAcβ1-2Manα1-6)Manβ1-4GlcNAcβ1-4(Fucα1-6)GlcNAcβ-Sp22 | 27 | 13 | 6 | 47 |
| 425 | Fucα1-2Galβ1-3GlcNAcβ1-2Manα1-3(Fucα1-2Galβ1-3GlcNAcβ1-2Manα1-6)Manβ1-4GlcNAcβ1-4(Fucα1-6)GlcNAcβ-Sp22 | 25 | 7 | 4 | 29 |
| 297 | Galβ1-3(Neu5Acα2-3Galβ1-4(Fucα1-3)GlcNAcβ1-3)GlcNAcβ1-6)GalNAcα-Sp14 | 23 | 20 | 10 | 88 |
| 336 | GlcNAcα1-4Galβ1-4GlcNAcβ1-3Galβ1-4GlcNAcβ-Sp0 | 21 | 16 | 8 | 76 |
| 88 | GlcNAcβ1-3Galβ1-3GalNAcα-Sp8 | 21 | 4 | 2 | 22 |
| 370 | Galα1-3(Fucα1-2)Galβ1-4GlcNAcβ1-2Manα1-3(Galα1-3(Fucα1-2)Galβ1-4GlcNAcβ1-2Manα1-6)Manβ1-4GlcNAcβ1-4GlcNAcβ-Sp20 | 20 | 8 | 4 | 39 |
| 190 | GlcNAcβ1-6GalNAcα-Sp8 | 18 | 11 | 5 | 60 |

Figure 3A

| | | | | | |
|---|---|---|---|---|---|
| 192 | GlcNAcβ1-6Galβ1-4GlcNAcβ-Sp8 | 18 | 14 | 7 | 81 |
| 463 | Galα1-3(Fucα1-2)Galβ1-3GalNAcb-Sp8 | 17 | 17 | 9 | 98 |
| 427 | Galβ1-3GlcNAcβ1-2Manα1-3(Galβ1-3GlcNAcβ1-2(Galβ1-3GlcNAcβ1-6)Manα1-6)Manβ1-4GlcNAcβ1-4GlcNAcβ-Sp19 | 17 | 16 | 8 | 93 |
| 460 | Galβ1-4GlcNAcβ1-6(Galβ1-4GlcNAcβ1-2)Manα1-6(Galβ1-4GlcNAcβ1-2Manα1-3)Manβ1-4GlcNAcβ1-4GlcNAcβ-Sp19 | 17 | 3 | 1 | 16 |
| 284 | Neu5Gcα2-6Galβ1-4GlcNAcβ-Sp0 | 17 | 11 | 6 | 68 |
| 53 | Galβ1-4GlcNAcβ1-2Manα1-3(Galβ1-4GlcNAcβ1-2Manα1-6)Manβ1-4GlcNAcβ1-4GlcNAcβ-Sp12 | 17 | 17 | 8 | 100 |
| 417 | GalNAcα1-3(Fucα1-2)Galβ1-4(Fucα1-3)GlcNAcβ1-3GalNAc-Sp14 | 17 | 8 | 4 | 48 |
| 340 | GlcNAcα1-4Galβ1-4GlcNAcβ1-3Galβ1-4(Fucα1-3)GlcNAcβ1-3Galβ1-4(Fucα1-3)GlcNAcβ-Sp0 | 17 | 8 | 4 | 47 |
| 57 | Neu5Acα2-6Galβ1-4GlcNAcβ1-2Manα1-3(Neu5Acα2-6Galβ1-2Manα1-6)Manβ1-4GlcNAcβ1-4GlcNAcβ-Sp13 | 16 | 5 | 3 | 32 |
| 23 | [3OSO3]Galβ1-4(Fucα1-3)[6OSO3]Glc-Sp0 | 16 | 13 | 6 | 77 |
| 424 | Galα1-3Galβ1-3GlcNAcβ1-3GalNAc-Sp14 | 16 | 22 | 11 | 135 |
| 50 | Manα1-3(Manα1-6)Manβ1-4GlcNAcβ1-4GlcNAcβ-Sp13 | 16 | 12 | 6 | 75 |
| 415 | Fucα1-2Galβ1-4(Fucα1-3)GlcNAcβ1-3GalNAc-Sp14 | 16 | 6 | 3 | 39 |
| 255 | Neu5Acα2-3Galβ1-3GlcNAcβ1-3Galβ1-4GlcNAcβ-Sp8 | 16 | 6 | 3 | 36 |
| 390 | Galβ1-3GlcNAcα1-3GalNAcα-Sp14 | 15 | 7 | 3 | 44 |
| 405 | Galβ1-3GlcNAcα1-6Galβ1-4GlcNAcβ-Sp0 | 15 | 5 | 3 | 35 |
| 454 | Neu5Acα2-8Neu5Acα2-3Galβ1-3GalNAcβ1-4(Neu5Acα2-8Neu5Acα2-3)Galβ1-4Glcb-sp0 | 15 | 12 | 6 | 76 |
| 448 | Galβ1-4GlcNAcβ1-6GalNAcα-Sp14 | 15 | 4 | 2 | 30 |
| 249 | Neu5Acα2-3Galβ1-4[6OSO3]GlcNAcβ-Sp8 | 14 | 8 | 4 | 55 |
| 420 | GlcNAcβ1-2Manα1-3(GlcNAcβ1-2(GlcNAcβ1-6)Manα1-6)Manβ1-4GlcNAcβ1-4GlcNAcβ-Sp19 | 14 | 5 | 3 | 36 |
| 161 | Galβ1-4GlcNAcβ1-3Galβ1-4GlcNAcβ-Sp0 | 14 | 9 | 5 | 68 |
| 82 | GalNAcα1-3(Fucα1-2)Galβ1-3GlcNAcβ1-4Glcβ-Sp0 | 14 | 16 | 8 | 115 |
| 274 | Neu5Acα2-8Neu5Acα2-3Galβ1-4Glcβ-Sp0 | 14 | 12 | 6 | 89 |
| 73 | Fucα1-2Galβ1-4Glcα1-4Galβ1-4GlcNAcβ-Sp10 | 14 | 9 | 4 | 63 |
| 465 | Glcα1-4Glcα1-4Glcβ-Sp10 | 14 | 12 | 6 | 86 |
| 94 | GalNAcβ1-3GalNAcα-Sp8 | 13 | 13 | 7 | 99 |

Figure 3A Cont...

| | | | | | |
|---|---|---|---|---|---|
| 426 | Galα1-3(Fucα1-2)Galβ1-4GlcNAcβ1-2Manα1-3(Galα1-3(Fucα1-2)Galβ1-4GlcNAcβ1-2Manα1-6)Manβ1-4GlcNAcβ1-4(Fucα1-6)GlcNAcβ-Sp22 | 13 | 4 | 2 | 33 |
| 168 | Galβ1-4GlcNAcβ-Sp8 | 13 | 4 | 2 | 30 |
| 250 | Neu5Acα2-3Galβ1-4(Fucα1-3)[6OSO3]GlcNAcβ-Sp8 | 13 | 9 | 5 | 71 |
| 248 | Neu5Acα2-3Galβ1-3GlcNAcβ-Sp8 | 13 | 6 | 3 | 47 |
| 349 | Galβ1-4GlcNAcβ1-2Manα1-3(Manα1-6)Manβ1-4GlcNAcβ1-4GlcNAcβ-Sp12 | 13 | 6 | 3 | 48 |
| 288 | Galβ1-4(Fucα1-3)[6OSO3]GlcNAc-Sp0 | 13 | 14 | 7 | 112 |
| 175 | GlcNAcβ1-3(GlcNAcβ1-6)Galβ1-4GlcNAcβ-Sp8 | 12 | 7 | 4 | 60 |
| 2 | Glcα-Sp8 | 12 | 17 | 8 | 134 |
| 360 | Fucα1-2Galβ1-4GlcNAcβ1-2Manα1-3(Fucα1-2Galβ1-4GlcNAcβ1-2Manα1-6)Manβ1-4GlcNAcβ1-4GlcNAcβ-Sp20 | 12 | 2 | 1 | 16 |
| 393 | Galα1-3Galβ1-3GlcNAcβ1-2Manα1-3(Galα1-3Galβ1-3GlcNAcβ1-2Manα1-6)Manβ1-4GlcNAcβ1-4GlcNAc-Sp19 | 12 | 3 | 1 | 24 |
| 295 | [6OSO3]Galβ1-4[6OSO3]GlcNAcβ-Sp0 | 12 | 3 | 1 | 25 |
| 185 | GlcNAcβ1-4Galβ1-4GlcNAcβ-Sp8 | 12 | 9 | 4 | 71 |
| 445 | Fucα1-2Galβ1-4GlcNAcβ1-2(Fucα1-2Galβ1-4GlcNAcβ1-4)Manα1-3(Fucα1-2Galβ1-4 GlcNAcβ1-2Manα1-6)Manβ1-4GlcNAcβ1-4GlcNAcβ-Sp12 | 12 | 6 | 3 | 47 |
| 409 | Neu5Acα2-6Galβ1-3GlcNAcβ1-4(GalβNAcβ1-4GlcNAcβ1-6)Galβ1-4Glc-Sp21 | 12 | 8 | 4 | 64 |
| 344 | Neu5Acα2-6Galβ1-4GlcNAcβ1-2Manα1-3(Manα1-6)Manβ1-4GlcNAcβ1-4GlcNAc-Sp12 | 12 | 4 | 2 | 33 |
| 83 | GalNAcα1-3(Fucα1-2)Galβ1-4(Fucα1-3)GlcNAcβ-Sp0 | 12 | 5 | 2 | 40 |
| 20 | GlcNAcβ1-3(GlcNAcβ1-4)(GlcNAcβ1-6)GlcNAcα-Sp8 | 12 | 4 | 2 | 34 |
| 158 | Galβ1-4GalNAcβ1-3GalNAcα-Sp14 | 11 | 4 | 2 | 34 |
| 77 | Fucα1-2Galβ1-4Glcβ-Sp0 | 11 | 5 | 3 | 46 |
| 55 | Neu5Acα2-6Galβ1-4GlcNAcβ1-2Manα1-3(Neu5Acα2-6Galβ1-4GlcNAcβ1-2Manα1-6)Manβ1-4GlcNAcβ1-4GlcNAcβ-Sp8 | 11 | 9 | 4 | 77 |
| 112 | Galα1-3GalNAcβ-Sp8 | 11 | 5 | 2 | 43 |
| 444 | [6OSO3]Galβ1-3[6OSO3]GlcNAc-Sp0 | 11 | 8 | 4 | 72 |
| 446 | Fucα1-2Galβ1-4(Fucα1-3)GlcNAcβ1-2(Fucα1-2Galβ1-4(Fucα1-3)GlcNAcβ1-4)Manα1-6)Manβ1-4GlcNAcβ1-4GlcNAcβ-Sp12 | 11 | 11 | 5 | 97 |
| 69 | Fucα1-2Galβ1-4(Fucα1-3)GlcNAcβ1-3Galβ1-4(Fucα1-3)GlcNAcβ-Sp0 | 11 | 7 | 4 | 65 |

Figure 3A Cont...

| | | | | | |
|---|---|---|---|---|---|
| 282 | Neu5Gcα2-3Galβ1-4Glcβ-Sp0 | 11 | 11 | 5 | 100 |
| 111 | Galα1-3GalNAcα-Sp16 | 11 | 5 | 2 | 44 |
| 49 | Manα1-3(Manα1-6)Manβ1-4GlcNAcβ1-4GlcNAcβ-Sp12 | 11 | 12 | 6 | 114 |
| 204 | KDNα2-3Galβ1-4GlcNAcβ-Sp0 | 11 | 16 | 8 | 148 |
| 237 | Neu5Acα2-3Galβ1-3(Fucα1-4)GlcNAcβ-Sp8 | 11 | 5 | 3 | 48 |
| 303 | Galβ1-4GlcNAcβ1-6Galβ1-4GlcNAcβ-Sp0 | 11 | 4 | 2 | 37 |
| 51 | GlcNAcβ1-2Manα1-3(GlcNAcβ1-2Manα1-6)Manβ1-4GlcNAcβ1-4GlcNAcβ-Sp12 | 11 | 7 | 4 | 68 |
| 1 | Galα-Sp8 | 11 | 9 | 4 | 82 |
| 378 | (GalNAcβ1-4GlcNAcβ1-2Manα1-6)GalNAcβ1-4GlcNAcβ1-2Manα1-3Manβ1-4GlcNAcβ1-4GlcNAc-Sp12 | 10 | 6 | 3 | 54 |
| 40 | 6-H2PO3Manα-Sp8 | 10 | 13 | 7 | 129 |
| 280 | Neu5Gcα2-3Galβ1-4(Fucα1-3)GlcNAcβ-Sp0 | 10 | 6 | 3 | 63 |
| 388 | Fucα1-2Galβ1-3GalNAcα1-3(Fucα1-2)Galβ1-4Glcβ-Sp0 | 10 | 10 | 5 | 95 |
| 351 | Galβ1-4GlcNAcβ1-2Manα1-3(Galβ1-4GlcNAcβ1-2Manα1-6)Manβ1-4GlcNAcβ1-4(Fucα1-6)GlcNAcβ-Sp22 | 10 | 7 | 4 | 74 |
| 59 | Fucα1-2Galβ1-3GalNAcβ1-3Galα1-4Galβ1-4Glcβ-Sp9 | 10 | 11 | 6 | 110 |
| 231 | Neu5Acα2-3(GalNAcβ1-4)Galβ1-4Glcβ-Sp0 | 10 | 6 | 3 | 60 |
| 435 | Galβ1-4GlcNAcβ1-4(Galβ1-4GlcNAcβ1-2)Manα1-3(GlcNAcβ1-4)(Galβ1-4GlcNAcβ1-2Manα1-6)Manβ1-4GlcNAcβ1-4GlcNAc-Sp21 | 10 | 9 | 4 | 87 |
| 407 | GlcNAcβ1-6(GlcNAcβ1-3)GalNAcα-Sp14 | 10 | 9 | 5 | 93 |
| 350 | GlcNAcβ1-2Manα1-3(GlcNAcβ1-2Manα1-6)Manβ1-4GlcNAcβ1-4(Fucα1-6)GlcNAcβ-Sp22 | 10 | 3 | 1 | 30 |
| 285 | Neu5Gcα-Sp8 | 10 | 5 | 2 | 51 |
| 406 | GalNAcβ1-3Galα1-6Galβ1-4Glcβ-Sp8 | 10 | 1 | 1 | 16 |
| 78 | Fucα1-2Galβ1-4Glcβ-Sp8 | 10 | 10 | 5 | 102 |
| 186 | GlcNAcβ1-4GlcNAcβ1-4GlcNAcβ1-4GlcNAcβ1-4GlcNAcβ1-4β-Sp8 | 9 | 3 | 2 | 34 |
| 306 | GlcNAcβ1-2Manα1-3(Neu5Acα2-6Galβ1-4GlcNAcβ1-2Manα1-6)Manβ1-4GlcNAcβ1-4GlcNAcβ-Sp12 | 9 | 6 | 3 | 67 |
| 155 | Galβ1-4GalNAcα1-3(Fucα1-2)Galβ1-4GlcNAcβ-Sp8 | 9 | 7 | 3 | 76 |
| 376 | Neu5Acα2-6Galβ1-4GlcNAcβ1-3GalNAc-Sp14 | 9 | 11 | 5 | 120 |
| 212 | Manα1-3(Manα1-2Manα1-2Manα1-6)Manα-Sp9 | 9 | 2 | 1 | 20 |

Figure 3A Cont...

| # | Glycan | | | |
|---|---|---|---|---|
| 252 | Neu5Acα2-3Galβ1-4(Fucα1-3)GlcNAcβ-Sp0 | 9 | 6 | 3 | 71 |
| 321 | Neu5Gcβ2-6Galβ1-4GlcNAc-Sp8 | 9 | 7 | 4 | 83 |
| 418 | Galβ1-4(Fucα1-3)GlcNAcβ1-2Manα1-3(Galβ1-4(Fucα1-3)GlcNAcβ1-2Manα1-6)Manβ1-4GlcNAcβ1-4(Fucα1-6)GlcNAcβ-Sp22 | 9 | 5 | 2 | 53 |
| 361 | Fucα1-2Galβ1-4(Fucα1-3)GlcNAcβ1-2Manα1-3(Fucα1-2Galβ1-4(Fucα1-3)GlcNAcβ1-2Manα1-6)Manβ1-4GlcNAcβ1-4GlcNAβ-Sp20 | 9 | 3 | 1 | 28 |
| 269 | Neu5Acα2-6Galβ1-4GlcNAcβ1-3Galβ1-4GlcNAcβ-Sp0 | 9 | 2 | 1 | 26 |
| 330 | Neu5Acα2-6Galβ1-4GlcNAcβ1-3Galβ1-4GlcNAcβ-Sp0 | 9 | 4 | 2 | 42 |
| 348 | Galβ1-4GlcNAcβ1-2Manα1-6Manβ1-4GlcNAcβ1-4GlcNAc-Sp12 | 9 | 2 | 1 | 25 |
| 318 | Neu5Acα2-6Galβ1-4GlcNAcβ1-2Manα1-3(Galβ1-2Manα1-6)Manβ1-4GlcNAcβ1-4GlcNAcβ-Sp12 | 9 | 6 | 3 | 64 |
| 352 | Galβ1-3GlcNAcβ1-2Manα1-3(Galβ1-3GlcNAcβ1-2Manα1-6)Manβ1-4GlcNAcβ1-4(Fucα1-6)GlcNAcβ-Sp22 | 9 | 14 | 7 | 161 |
| 307 | GlcNAcβ1-3Man-Sp10 | 9 | 1 | 1 | 17 |
| 337 | GlcNAcα1-4Galβ1-4GlcNAcβ-Sp0 | 9 | 6 | 3 | 73 |
| 441 | Neu5Acα2-3Galβ1-4GlcNAcβ1-3Galβ-Sp8 | 9 | 4 | 2 | 46 |
| 81 | Fucβ1-3GlcNAcβ-Sp8 | 9 | 15 | 7 | 175 |
| 392 | GalNAcα1-3(Fucα1-2)Galβ1-3GalNAcα1-3(Fucα1-2)Galβ1-4GlcNAcβ-Sp8 | 8 | 6 | 3 | 76 |
| 179 | GlcNAcβ1-3Galβ1-4GlcNAcβ-Sp0 | 8 | 9 | 5 | 107 |
| 217 | [3OSO3]Galβ1-4(Fucα1-3)[6OSO3]GlcNAc-Sp8 | 8 | 7 | 3 | 79 |
| 385 | Galβ1-3GlcNAcβ1-3(Galβ1-3GalNAcβ1-4(Fucα1-3)GlcNAcβ1-6)Galβ1-4Glc-Sp21 | 8 | 9 | 4 | 102 |
| 432 | GlcNAcβ1-2Manα1-3(GlcNAcβ1-4)(GlcNAcβ1-6(GlcNAcβ1-2)Manα1-6)Manβ1-4GlcNAcβ1-4GlcNAc-Sp21 | 8 | 10 | 5 | 119 |
| 58 | Fucα1-2Galβ1-3GalNAcα1-3Galα-Sp9 | 8 | 5 | 3 | 64 |
| 105 | Galα1-3(Fucα1-2)Galβ1-4GlcNAc-Sp0 | 8 | 3 | 2 | 36 |
| 195 | Glcα1-6Glcα1-6Glcβ-Sp8 | 8 | 9 | 4 | 102 |
| 54 | Neu5Acα2-6Galβ1-4GlcNAcβ1-2Manα1-3(Neu5Acα2-6Galβ1-4GlcNAcβ1-2Manα1-6)Manβ1-4GlcNAcβ1-4GlcNAcβ-N(LT)AVL | 8 | 9 | 4 | 105 |
| 260 | Fucα1-2Galβ1-4[6OSO3]Glc-Sp0 | 8 | 7 | 4 | 84 |
| 224 | Neu5Acα2-8Neu5Acα2-8Neu5Acα2-3(GalNAcβ1-4)Galβ1-4Glcβ-Sp0 | 8 | 7 | 3 | 83 |
| 342 | GlcNAcα1-4Galβ1-3GalNAc-Sp14 | 8 | 2 | 1 | 25 |

Figure 3A Cont...

| | | | | | |
|---|---|---|---|---|---|
| 334 | GalNAcα1-3(Fucα1-2)Galβ1-4GlcNAcβ1-3Galβ1-4GlcNAcβ1-3Galβ1-4GlcNAcβ-Sp0 | 8 | 4 | 2 | 54 |
| 273 | Neu5Acα2-8Neu5Acα-Sp8 | 8 | 6 | 3 | 80 |
| 262 | Neu5Acα2-3Galβ1-4Glcβ-Sp8 | 8 | 5 | 3 | 65 |
| 39 | [4OSO3]Galβ1-4GlcNAcβ-Sp8 | 8 | 3 | 1 | 32 |
| 384 | Fucα1-2Galβ1-3(Fucα1-4)GlcNAcβ1-3(Galβ1-4(Fucα1-3)GlcNAcβ1-6)Galβ1-4Glc-Sp21 | 8 | 5 | 3 | 69 |
| 382 | Galβ1-3GlcNAcβ1-3(Galβ1-4(Fucα1-3)GlcNAcβ1-6)Galβ1-4Glc-Sp21 | 8 | 5 | 3 | 69 |
| 19 | Galβ1-4GlcNAcβ1-3(Galβ1-4GlcNAcβ1-6)GalNAcα-Sp8 | 8 | 5 | 3 | 70 |
| 363 | Manα1-3(Galβ1-4GlcNAcβ1-2Manα1-6)Manβ1-4GlcNAcβ1-4GlcNAcβ-Sp12 | 8 | 4 | 2 | 54 |
| 3 | Manα-Sp8 | 8 | 7 | 4 | 95 |
| 176 | GlcNAcβ1-3GalNAcα-Sp8 | 8 | 6 | 3 | 82 |
| 411 | Neu5Acα2-3Galβ1-3GalNAcβ1-4(Neu5Acα2-8Neu5Acα2-3)Galβ1-4Glcβ-Sp0 | 8 | 5 | 2 | 63 |
| 261 | Neu5Acα2-3Galβ1-4Glcβ-Sp0 | 8 | 4 | 2 | 50 |
| 270 | Neu5Acα2-6Galβ1-4Glcβ-Sp0 | 8 | 5 | 2 | 58 |
| 89 | GalNAcα1-3(Fucα1-2)Galβ-Sp8 | 8 | 6 | 3 | 81 |
| 371 | Galα1-3Galβ1-4(Fucα1-3)GlcNAcβ1-2Manα1-3(Galα1-3Galβ1-4(Fucα1-3)GlcNAcβ1-2Manα1-6)Manβ1-4GlcNAcβ1-4GlcNAcβ-Sp20 | 8 | 4 | 2 | 57 |
| 10 | Neu5Acα-Sp11 | 8 | 3 | 2 | 45 |
| 214 | Manα1-6(Manα1-3)Manα1-6(Manα1-3)Manβ1-4GlcNAcβ1-4GlcNAcβ-Sp12 | 8 | 15 | 8 | 198 |
| 263 | Neu5Acα2-6GalNAcα-Sp8 | 8 | 6 | 3 | 85 |
| 399 | Galβ1-4(Fucα1-3)GlcNAcβ1-3GalNAcα-Sp14 | 8 | 9 | 5 | 123 |
| 86 | GalNAcα1-3(Fucα1-2)Galβ1-4GlcNAcβ-Sp8 | 8 | 6 | 3 | 79 |
| 233 | Neu5Acα2-3(Neu5Acα2-6)GalNAcα-Sp8 | 8 | 7 | 4 | 95 |
| 400 | GalNAcα1-3GalNAcβ1-3Galα1-4Galβ1-4GlcNAcβ-Sp0 | 8 | 10 | 5 | 126 |
| 419 | Fucα1-2Galβ1-4GlcNAcβ1-3Galβ1-4GlcNAcβ1-2Manα1-3(Fucα1-2Galβ1-4GlcNAcβ1-2Manα1-6)Manβ1-4GlcNAcβ1-4(Fucα1-6)GlcNAcβ-Sp22 | 7 | 7 | 4 | 101 |
| 92 | GalNAcα1-3Galβ-Sp8 | 7 | 3 | 2 | 44 |
| 135 | Galβ1-3(Neu5Acβ2-6)GalNAcα-Sp8 | 7 | 6 | 3 | 84 |
| 373 | Galα1-3(Fucα1-2)Galβ1-3GlcNAcβ1-2Manα1-3(Galα1-3(Fucα1-2)Galβ1-3GlcNAcβ1-2Manα1-6)Manβ1-4GlcNAcβ1-4GlcNAcβ-Sp20 | 7 | 6 | 3 | 82 |

Figure 3A Cont...

| | | | | |
|---|---|---|---|---|
| 166 | Galβ1-3(Galβ1-4GlcNAcβ1-6)GalNAcα-Sp14 | | | 60 |
| 134 | Galβ1-3(Neu5Acα2-6)GalNAcα-Sp14 | 7 | 1 | 2 | 20 |
| 283 | Neu5Gcα2-6GalNAcα-Sp0 | 7 | 9 | 1 | 118 |
| 146 | Galβ1-3GlcNAcβ1-3Galβ1-4Glcβ-Sp10 | 7 | 3 | 4 | 45 |
| 459 | GalNAcα1-3(Fucα1-2)Galβ1-3GlcNAcβ1-2Manα1-3(Fucα1-2)Galβ1-3GlcNAcβ1-2Manα1-3)Manβ1-4GlcNAcβ1-4(Fucα1-6)GlcNAcβ-Sp22 | 7 | 5 | 2 | 75 |
| 160 | Galβ1-4GlcNAcβ1-3Galβ1-4GlcNAcβ1-3GalNAcβ1-4GlcNAcβ-Sp0 | 7 | 2 | 3 | 31 |
| 298 | Galβ1-3Galβ1-4GlcNAcβ-Sp8 | 7 | 12 | 1 | 169 |
| 319 | Neu5Acβ1-8Neu5Acβ-Sp17 | 7 | 12 | 6 | 167 |
| 423 | GalNAcα1-3(Fucα1-2)Galβ1-3GlcNAcβ1-3GalNAc-Sp14 | 7 | 6 | 6 | 81 |
| 452 | Galα1-3Fucα1-2Galβ1-4GlcNAcβ1-3(Galα1-3Fucα1-2Galβ1-4GlcNAcβ1-6)GalNAc-Sp14 | 7 | 2 | 3 | 26 |
| 397 | Neu5Acα2-3Galβ1-3GlcNAcβ1-3GalNAcα-Sp14 | 7 | 8 | 1 | 108 |
| 128 | Galβ1-3(Fucα1-4)GlcNAcβ-Sp8 | 7 | 6 | 4 | 83 |
| 5 | GalNAcα-Sp15 | 7 | 12 | 3 | 165 |
| 129 | Galβ1-3(Fucα1-4)GlcNAc-Sp8 | 7 | 6 | 6 | 91 |
| 275 | Galβ1-3(Fucα1-4)GlcNAcβ1-3Galβ1-3(Fucα1-4)GlcNAcβ-Sp0 | 7 | 6 | 3 | 81 |
| 326 | Neu5Ac(9Ac)α2-3Galβ1-4GlcNAcβ-Sp0 | 7 | 8 | 4 | 108 |
| 338 | GlcNAcα1-4Galβ1-3GlcNAcβ-Sp0 | 7 | 7 | 4 | 108 |
| 97 | GalNAcβ1-4(Fucα1-3)GlcNAcβ-Sp0 | 7 | 1 | 0 | 7 |
| 254 | Neu5Acα2-3Galβ1-4(Fucα1-3)GlcNAcβ1-3Galβ-Sp8 | 7 | 1 | 0 | 10 |
| 110 | Galα1-3GalNAcα-Sp8 | 7 | 5 | 3 | 80 |
| 216 | Neu5Acα2-3Galβ1-4GlcNAcβ1-3Galβ1-4(Fucα1-3)GlcNAc-Sp0 | 7 | 6 | 3 | 86 |
| 317 | Neu5Acα2-6Galβ1-4GlcNAcβ1-3Galβ1-4GlcNAcβ1-2Manα1-3(Galβ1-4GlcNAcβ1-2Manα1-6)Manβ1-4GlcNAcβ1-4GlcNAcβ-Sp12 | 7 | 7 | 3 | 100 |
| 438 | Galα1-3Galβ1-4Glc-Sp10 | 7 | 6 | 3 | 86 |
| 149 | Galβ1-4(Fucα1-3)GlcNAcβ-Sp0 | 7 | 2 | 1 | 34 |
| 268 | Neu5Acα2-6Galβ1-4GlcNAcβ1-3Galβ1-4(Fucα1-3)GlcNAcβ-Sp0 | 7 | 2 | 1 | 24 |
| 240 | Neu5Acα2-3Galβ1-3[6OSO3]GalNAcα-Sp8 | 7 | 2 | 1 | 30 |

Figure 3A Cont...

| | | | | | |
|---|---|---|---|---|---|
| 183 | GlcNAcβ1-4-MDPLys | 7 | 3 | 2 | 48 |
| 368 | Galβ1-4GlcNAcβ1-2(Galβ1-4GlcNAcβ1-4)Manα1-3(Galβ1-4GlcNAcβ1-2Manα1-6)Manβ1-4GlcNAcβ1-4GlcNAc-Sp21 | 7 | 8 | 4 | 122 |
| 140 | Galβ1-3GalNAcβ-Sp8 | 7 | 3 | 1 | 43 |
| 325 | Fucα1-3(Galβ1-4)GlcNAcβ1-2Manα1-3(Fucα1-3(Galβ1-4)GlcNAcβ1-2Manα1-6)Manβ1-4GlcNAcβ1-4GlcNAcβ-Sp20 | 7 | 8 | 4 | 115 |
| 413 | GalNAcα1-3(Fucα1-2)Galβ1-4GlcNAcβ1-3GalNAcα-Sp14 | 7 | 9 | 5 | 140 |
| 395 | Galβ1-4GlcNAcβ1-2Manα1-3(GlcNAcβ1-2Manα1-6)Manβ1-4GlcNAcβ1-4GlcNAc-Sp12 | 7 | 7 | 3 | 103 |
| 173 | GlcNAcβ1-2Galβ1-3GalNAcα-Sp8 | 6 | 5 | 2 | 74 |
| 209 | Manα1-2Manα1-6(Manα1-3)Manα1-6(Manα1-2Manα1-2Manα1-3)Manβ1-4GlcNAcβ1-4GlcNAcβ-Sp12 | 6 | 8 | 4 | 122 |
| 28 | [3OSO3]Galβ1-3GalNAcα-Sp8 | 6 | 8 | 4 | 125 |
| 436 | Galβ1-4GlcNAcβ1-2Manα1-3(GlcNAcβ1-4)(Galβ1-4GlcNAcβ1-6(Galβ1-4GlcNAcβ1-2)Manα1-6)Manβ1-4GlcNAcβ1-4GlcNAc-Sp21 | 6 | 3 | 1 | 40 |
| 333 | GalNAcα1-3(Fucα1-2)Galβ1-4GlcNAcβ1-3Galβ1-4GlcNAcβ-Sp0 | 6 | 3 | 2 | 48 |
| 450 | Galβ1-4GlcNAcβ1-2Manα-Sp0 | 6 | 5 | 2 | 71 |
| 345 | Neu5Acα2-6Galβ1-4GlcNAcβ1-2Manα1-6Manβ1-4GlcNAc-Sp12 | 6 | 5 | 3 | 81 |
| 229 | Neu5Acα2-3(GalNAcβ1-4)Galβ1-4GlcNAcβ-Sp0 | 6 | 2 | 1 | 25 |
| 244 | Neu5Acα2-3Galβ1-3GalNAcβ1-3Galα1-4Galβ1-4Glcβ-Sp0 | 6 | 8 | 4 | 120 |
| 178 | GlcNAcβ1-3Galβ-Sp8 | 6 | 4 | 2 | 64 |
| 8 | Rhaα-Sp8 | 6 | 8 | 4 | 130 |
| 310 | HOOC(CH3)CH-3-O-GlcNAcβ1-4GlcNAcβ-Sp10 | 6 | 4 | 4 | 127 |
| 238 | Neu5Acα2-3Galβ1-3(Fucα1-4)GlcNAcβ1-3Galβ1-4(Fucα1-3)GlcNAcβ-Sp0 | 6 | 4 | 2 | 69 |
| 381 | Galβ1-3GlcNAcβ1-3(Galβ1-3GlcNAcβ1-3Galβ1-4GlcNAcβ1-6)Galβ1-4Glcβ-Sp0 | 6 | 7 | 4 | 121 |
| 356 | KDNα2-6Galβ1-4GlcNAc-Sp0 | 6 | 5 | 2 | 81 |
| 258 | Neu5Acα2-3Galβ1-4GlcNAcβ-Sp8 | 6 | 4 | 2 | 63 |
| 109 | Galα1-3(Galα1-4)Galβ1-4GlcNAcβ-Sp8 | 6 | 8 | 4 | 125 |
| 207 | Manα1-2Manα1-3Manα-Sp9 | 6 | 1 | 1 | 17 |
| 44 | [6OSO3]Galβ1-4[6OSO3]Glcβ-Sp8 | 6 | 4 | 2 | 62 |

Figure 3A Cont...

| | | | | | |
|---|---|---|---|---|---|
| 301 | Galβ1-4GlcNAcβ1-3(GlcNAcβ1-6)Galβ1-4GlcNAc-Sp0 | 6 | 4 | 2 | 73 |
| 151 | Galβ1-4(Fucα1-3)GlcNAcβ1-3Galβ1-4(Fucα1-3)GlcNAcβ-Sp0 | 6 | 7 | 4 | 122 |
| 165 | Galβ1-3(Galβ1-4GlcNAcβ1-6)GalNAcα-Sp8 | 6 | 6 | 3 | 93 |
| 302 | Galβ1-4GlcNAcα1-6Galβ1-4GlcNAc-Sp0 | 6 | 8 | 4 | 125 |
| 63 | Fucα1-2Galβ1-3GalNAcβ1-4(Neu5Acα2-3)Galβ1-4Glcβ-Sp0 | 6 | 4 | 2 | 61 |
| 383 | Fucα1-2Galβ1-3(Fucα1-4)GlcNAcβ1-3(Galβ1-4GlcNAcβ1-6)Galβ1-4Glcβ-Sp21 | 6 | 8 | 4 | 139 |
| 102 | Galα1-3(Fucα1-2)Galβ1-3GlcNAcβ-Sp8 | 6 | 8 | 4 | 140 |
| 143 | Galβ1-3GalNAcβ1-4Galβ1-4Glcβ-Sp8 | 6 | 4 | 2 | 66 |
| 27 | [3OSO3]Galβ1-3(Fucα1-4)GlcNAcβ-Sp8 | 6 | 5 | 3 | 91 |
| 449 | Galβ1-4(Fucα1-3)GlcNAcβ1-6GalNAcα-Sp14 | 6 | 6 | 3 | 101 |
| 443 | [6OSO3]Galβ1-3GlcNAcβ-Sp0 | 6 | 5 | 3 | 92 |
| 246 | Fucα1-2[6OSO3]Galβ1-4Glc-Sp0 | 6 | 6 | 3 | 104 |
| 299 | Galβ1-4GlcNAcβ1-2Manα1-3(Neu5Acα2-6Galβ1-4GlcNAcβ1-2Manα1-6)Manβ1-4GlcNAcβ1-4GlcNAcβ-Sp12 | 6 | 5 | 2 | 84 |
| 391 | Neu5Acα2-3(GalNAcβ1-4)Galβ1-4GlcNAcβ1-3GalNAcα-Sp14 | 6 | 11 | 6 | 196 |
| 7 | Fucα-Sp9 | 6 | 5 | 3 | 93 |
| 36 | [3OSO3]Galβ1-4GlcNAcβ-Sp8 | 6 | 7 | 3 | 118 |
| 322 | Galβ1-3GlcNAcβ1-2Manα1-3(Galβ1-3GlcNAcβ1-2Manα1-6)Manβ1-4GlcNAcβ1-4GlcNAcβ-Sp19 | 6 | 4 | 2 | 65 |
| 309 | GlcNAcβ1-4GlcNAcβ-Sp12 | 6 | 3 | 2 | 57 |
| 447 | Galβ1-4GlcNAcβ1-3(Galβ1-4GlcNAcβ1-6)GalNAc-Sp14 | 6 | 2 | 1 | 28 |
| 85 | GalNAcα1-3(Fucα1-2)Galβ1-4GlcNAcβ-Sp0 | 6 | 6 | 3 | 107 |
| 354 | [6OSO3]GlcNAcβ1-3Galβ1-4GlcNAc-β-Sp0 | 6 | 6 | 3 | 115 |
| 202 | GlcAβ1-6Galβ-Sp8 | 6 | 8 | 4 | 140 |
| 130 | Galβ1-4GlcNAcβ1-6GalNAcα-Sp8 | 6 | 9 | 5 | 168 |
| 32 | [3OSO3]Galβ1-4(Fucα1-3)GlcNAcβ-Sp8 | 6 | 6 | 3 | 107 |
| 223 | Neu5Acα2-8Neu5Acα2-8Neu5Acα2-3(GalNAcβ1-4)Galβ1-4Glcβ-Sp0 | 5 | 3 | 1 | 52 |
| 95 | GalNAcβ1-3(Fucα1-2)Galβ-Sp8 | 5 | 5 | 3 | 93 |
| 84 | [3OSO3]Galβ1-4(Fucα1-3)Glc-Sp0 | 5 | 6 | 3 | 113 |

Figure 3A Cont...

| | | | | | |
|---|---|---|---|---|---|
| 362 | Galα1-3Galβ1-4GlcNAcβ1-2Manα1-3(Galα1-3Galβ1-4GlcNAcβ1-2Manα1-6)Manβ1-4GlcNAcβ1-4GlcNAcβ-Sp20 | 5 | 5 | 2 | 91 |
| 153 | Galβ1-4[6OSO3]Glcβ-Sp0 | 5 | 3 | 2 | 57 |
| 96 | GalNAcβ1-3Galα1-4Galβ1-4GlcNAcβ-Sp0 | 5 | 2 | 1 | 32 |
| 335 | Neu5Acα2-3-Galβ1-3(Galβ1-4(Fucα1-3)GlcNAcβ1-6)GalNAc-Sp14 | 5 | 5 | 3 | 103 |
| 343 | Manα1-3(Neu5Acα2-6Galβ1-4GlcNAcβ1-2Manα1-6)Manβ1-4GlcNAc-Sp12 | 5 | 3 | 2 | 67 |
| 104 | Galα1-3(Fucα1-2)Galβ1-4(Fucα1-3)GlcNAcβ-Sp8 | 5 | 4 | 2 | 79 |
| 357 | KDNα2-3Galβ1-4Glc-Sp0 | 5 | 9 | 4 | 167 |
| 264 | Neu5Acα2-6GalNAcβ1-4GlcNAcβ-Sp0 | 5 | 11 | 5 | 212 |
| 208 | Manα1-6(Manα1-2Manα1-3)Manα1-6(Manα1-2Manα1-3)Manβ1-4GlcNAcβ1-4GlcNAcβ-Sp12 | 5 | 2 | 1 | 30 |
| 410 | Galβ1-3GalNAcβ1-4(Neu5Acα2-8Neu5Acα2-3)Galβ1-4Glcβ-Sp0 | 5 | 3 | 2 | 61 |
| 107 | Galα1-3(Fucα1-2)Galβ-Sp8 | 5 | 5 | 3 | 106 |
| 339 | GlcNAcα1-4Galβ1-4GlcNAcβ1-3Galβ1-4GlcNAcβ-Sp0 | 5 | 5 | 2 | 91 |
| 259 | Neu5Acα2-3Galβ1-4GlcNAcβ1-3Galβ1-4GlcNAcβ-Sp0 | 5 | 12 | 6 | 228 |
| 251 | Neu5Acα2-3Galβ1-3GalNAcβ1-4(Fucα1-3)GlcNAcβ1-3Galβ1-4(Fucα1-3)GlcNAcβ-Sp0 | | 7 | 4 | 145 |
| 194 | Glcα1-4Glcα-Sp8 | 5 | 6 | 3 | 119 |
| 293 | Neu5Acα2-3Galβ1-4GlcNAcβ1-3Galβ1-3GlcNAcβ-Sp0 | 5 | 5 | 2 | 97 |
| 93 | GalNAcα1-4(Fucα1-2)Galβ1-4GlcNAcβ-Sp8 | 5 | 4 | 2 | 80 |
| 464 | Glcα1-6Glcα1-6Glcα1-6Glcβ-Sp10 | 5 | 3 | 2 | 70 |
| 136 | Galβ1-3(Neu5Acα2-6)Galβ1-4GlcNAcβ-Sp10 | 5 | 7 | 4 | 144 |
| 164 | Galβ1-4GlcNAcβ1-6(Galβ1-3)GalNAcα-Sp8 | 5 | 3 | 1 | 55 |
| 396 | GlcNAcβ1-2Manα1-3(Galβ1-4GlcNAcβ1-2Manα1-6)Manβ1-4GlcNAc-Sp12 | 5 | 7 | 4 | 144 |
| 453 | GalNAcα1-3Fucα1-2Galβ1-3GlcNAcβ1-3(GalNAcα1-3Fucα1-3(Galβ1-4GlcNAcβ1-6)GalNAc-Sp14 | 5 | 3 | 2 | 70 |
| 457 | Galα1-3(Fucα1-2)Galβ1-3GlcNAcβ1-2Manα1-6(Galα1-3(Fucα1-2)Galβ1-3GlcNAcβ1-2Manα1-3)Manβ1-4GlcNAcβ1-4(Fucα1-6)GlcNAcβ-Sp22 | 5 | 6 | 3 | 122 |
| 289 | Galβ1-4(Fucα1-3)[6OSO3]Glc-Sp0 | 5 | 3 | 1 | 58 |
| 152 | Galβ1-4(Fucα1-3)GlcNAcβ1-4Galβ1-4(Fucα1-3)GlcNAcβ-Sp0 | 5 | 5 | 3 | 112 |
| 123 | Galα1-6Glcβ-Sp8 | 5 | 4 | 2 | 92 |

Figure 3A Cont...

| | | | | | |
|---|---|---|---|---|---|
| 386 | Galβ1-4GlcNAcβ1-2(Galβ1-4GlcNAcβ1-4)Manα1-3(Galβ1-4GlcNAcβ1-2(Galβ1-4GlcNAcβ1-6)Manα1-6)Manβ1-4GlcNAcβ1-4GlcNAcβ-Sp21 | 5 | 5 | 3 | 110 |
| 121 | Galα1-4Galβ1-4Glcβ-Sp0 | 5 | 3 | 2 | 70 |
| 374 | Fucα1-2Galβ1-3(Fucα1-4)GlcNAcβ1-2Manα1-3(Fucα1-2Galβ1-3(Fucα1-4)GlcNAcβ1-2Manα1-6)Manβ1-4GlcNAcβ1-4GlcNAcβ-Sp19 | 5 | 3 | 2 | 74 |
| 56 | Neu5Acα2-6Galβ1-4GlcNAcβ1-2Manα1-3(Neu5Acα2-6Galβ1-4GlcNAcβ1-2Manα1-6)Manβ1-4GlcNAcβ1-4GlcNAcβ-Sp12 | 5 | 4 | 2 | 94 |
| 290 | Galβ1-4(Fucα1-3)GlcNAcβ1-3Galβ1-3(Fucα1-4)GlcNAcβ-Sp0 | 5 | 8 | 4 | 183 |
| 272 | Neu5Acα2-6Galβ-Sp8 | 5 | 9 | 5 | 204 |
| 87 | GalNAcα1-3(Fucα1-2)Galβ1-4Glcβ-Sp0 | 5 | 4 | 2 | 83 |
| 394 | Galα1-3Galβ1-3(Fucα1-4)GlcNAcβ1-2Manα1-3(Galα1-3Galβ1-3(Fucα1-4)GlcNAcβ1-2Manα1-6)Manβ1-4GlcNAcβ1-4GlcNAc-Sp19 | 5 | 4 | 2 | 86 |
| 429 | Galβ1-4GlcNAcβ1-3Galβ1-4(Fucα1-3)GlcNAcβ1-3GlcNAcβ1-6)Galβ1-4Glc-Sp21 | 5 | 7 | 4 | 164 |
| 456 | GalNAcα1-3(Fucα1-2)Galβ1-4GlcNAcβ1-2Manα1-6(GalNAcα1-3(Fucα1-2)Galβ1-4GlcNAcβ1-2Manα1-3)Manβ1-4GlcNAcβ1-4(Fucα1-6)GlcNAcβ-Sp22 | 5 | 8 | 4 | 167 |
| 196 | Glcβ1-4Glcβ-Sp8 | 4 | 5 | 3 | 116 |
| 193 | Glcα1-4Glcβ-Sp8 | 4 | 6 | 3 | 127 |
| 34 | [3OSO3]Galβ1-4[6OSO3]GlcNAcβ-Sp8 | 4 | 9 | 4 | 199 |
| 118 | Galα1-4(Fucα1-2)Galβ1-4GlcNAcβ-Sp8 | 4 | 4 | 2 | 99 |
| 369 | GalNAcα1-3(Fucα1-2)Galβ1-4GlcNAcβ1-2Manα1-3(GalNAcα1-3(Fucα1-2)Galβ1-4GlcNAcβ1-2Manα1-6)Manβ1-4GlcNAcβ1-4GlcNAcβ-Sp20 | 4 | 4 | 2 | 98 |
| 221 | Neu5Acα2-3Galβ1-3GalNAcα-Sp8 | 4 | 6 | 3 | 141 |
| 22 | [3OSO3][6OSO3]Galβ1-4GlcNAcβ-Sp0 | 4 | 8 | 4 | 190 |
| 43 | [6OSO3]Galβ1-4GlcNAcβ-Sp8 | 4 | 6 | 3 | 145 |
| 215 | Manβ1-4GlcNAcβ-Sp0 | 4 | 4 | 2 | 105 |
| 124 | Galβ1-2Galβ-Sp8 | 4 | 4 | 2 | 92 |
| 30 | [3OSO3]Galβ1-3GlcNAcβ-Sp8 | 4 | 5 | 3 | 133 |
| 294 | [3OSO3][4OSO3]Galβ1-4GlcNAcβ-Sp0 | 4 | 6 | 3 | 137 |
| 300 | Galβ1-4GlcNAcβ1-3(Galβ1-4GlcNAcβ1-6)Galβ1-4GlcNAc-Sp0 | 4 | 4 | 2 | 109 |
| 99 | GalNAcβ1-4GlcNAcβ-Sp8 | 4 | 4 | 2 | 109 |

Figure 3A Cont...

| | | | | | |
|---|---|---|---|---|---|
| 379 | Galβ1-3GalNAcα1-3(Fucα1-2)Galβ1-4Glc-Sp0 | 4 | 5 | 2 | 122 |
| 198 | G-ol-Sp8 | 4 | 5 | 3 | 135 |
| 42 | [6OSO3]Galβ1-4Glcβ-Sp8 | 4 | 4 | 2 | 100 |
| 328 | Neu5Acα2-6Galβ1-4GlcNAcβ1-3Galβ1-3GlcNAcβ-Sp0 | 4 | 2 | 1 | 52 |
| 218 | Fucα1-2[6OSO3]Galβ1-4GlcNAc-Sp0 | 4 | 5 | 2 | 129 |
| 159 | Galβ1-4GlcNAcβ1-3Galβ1-4(Fucα1-3)GlcNAcβ1-3Galβ1-4(Fucα1-3)GlcNAcβ-Sp0 | 4 | 10 | 5 | 281 |
| 120 | Galα1-4Galβ1-4GlcNAcβ-Sp8 | 4 | 5 | 3 | 147 |
| 239 | Neu5Acα2-3Galβ1-3(Neu5Acα2-3Galβ1-4)GlcNAcβ-Sp8 | 4 | 4 | 2 | 108 |
| 402 | Galα1-4Galβ1-4GlcNAcβ1-2Manα1-3(Galα1-4Galβ1-4GlcNAcβ1-2Manα1-6)Manβ1-4GlcNAcβ1-4GlcNAcβ-LVANKT | | 9 | 4 | 247 |
| 70 | Fucα1-2Galβ1-4(Fucα1-3)GlcNAcβ1-3Galβ1-4(Fucα1-3)GlcNAcβ-Sp0 | 4 | 7 | 3 | 182 |
| 296 | 6-H2PO3Glcβ-Sp10 | 4 | 3 | 2 | 85 |
| 80 | Fucα1-4GlcNAcβ-Sp8 | 4 | 3 | 2 | 87 |
| 205 | Manα1-2Manα1-2Manα1-3Manα-Sp9 | 3 | 6 | 3 | 176 |
| 242 | Neu5Acα2-3(Neu5Acα2-6)GalNAcα-Sp14 | 3 | 3 | 1 | 79 |
| 276 | Neu5Acβ2-6GalNAcα-Sp8 | 3 | 7 | 3 | 197 |
| 147 | Galβ1-3GlcNAcβ-Sp0 | 3 | 3 | 1 | 75 |
| 219 | Fucα1-2Galβ1-4[6OSO3]GlcNAc-Sp8 | 3 | 10 | 5 | 288 |
| 331 | Galα1-4GlcNAcβ1-3Galβ1-4Glcβ-Sp0 | 3 | 7 | 3 | 201 |
| 315 | Neu5Acα2-3Galβ1-3(Neu5Acα2-3Galβ1-4GlcNAcβ1-6)GalNAcα-Sp14 | 3 | 3 | 1 | 75 |
| 256 | Neu5Acα2-3Galβ1-3(Neu5Acα2-3Galβ1-4GlcNAcβ1-6)Galβ1-4GlcNAcβ-Sp0 | 3 | 5 | 3 | 163 |
| 355 | KDNα2-3Galβ1-4(Fucα1-3)GlcNAc-Sp0 | 3 | 5 | 2 | 144 |
| 162 | Galβ1-4GlcNAcα2-3Galβ1-4Glcβ-Sp0 | 3 | 5 | 2 | 137 |
| 230 | Neu5Acα2-3(GalNAcβ1-4)Galβ1-4GlcNAcβ-Sp8 | 3 | 7 | 3 | 211 |
| 243 | Neu5Acα2-3Galβ-Sp8 | 3 | 6 | 3 | 195 |
| 101 | Galα1-3(Fucα1-2)Galβ1-3GlcNAcβ-Sp0 | 3 | 6 | 3 | 201 |
| 177 | GlcNAcβ1-3GalNAcα-Sp14 | 3 | 2 | 1 | 72 |
| 98 | GalNAcβ1-4GlcNAcβ-Sp0 | 3 | 4 | 2 | 124 |

Figure 3A Cont...

| | | | | |
|---|---|---|---|---|
| 433 | GlcNAcβ1-4(GlcNAcβ1-2)Manα1-3(GlcNAcβ1-4)(GlcNAcβ1-6(GlcNAcβ1-2)Manα1-6)Manβ1-4GlcNAcβ1-4GlcNAc-Sp21 | 3 | 5 | 3 | 176 |
| 286 | Galβ1-3(Neu5Acα2-3Galβ1-4GlcNAcβ1-6)GalNAcα-Sp14 | 3 | 2 | 1 | 53 |
| 227 | Neu5Acα2-8Neu5Acα2-8Neu5Acα-Sp8 | 3 | 3 | 1 | 85 |
| 188 | GlcNAcβ1-4GlcNAcβ1-4GlcNAcβ1-4GlcNAcβ-Sp8 | 3 | 7 | 3 | 223 |
| 372 | GalNAcα1-3(Fucα1-2)Galβ1-3GlcNAcβ1-3(GalNAcα1-3(Fucα1-2)Galβ1-3GlcNAcβ1-2Manα1-6)Manβ1-4GlcNAcβ1-4GlcNAcβ-Sp20 | 3 | 8 | 4 | 264 |
| 327 | Neu5Ac(9Ac)α2-3Galβ1-3GlcNAcβ-Sp0 | 3 | 6 | 3 | 203 |
| 79 | Fucα1-3GlcNAcβ-Sp8 | 3 | 5 | 2 | 157 |
| 12 | Galβ-Sp8 | 3 | 5 | 2 | 160 |
| 13 | Glcβ-Sp8 | 3 | 4 | 2 | 128 |
| 181 | GlcNAcβ1-3Galβ1-4GlcNAcβ1-3Galβ1-4GlcNAcβ-Sp0 | 3 | 4 | 2 | 124 |
| 304 | GalNAcβ1-4GlcNAcβ-Sp8 | 3 | 6 | 3 | 211 |
| 61 | Fucα1-2Galβ1-3GalNAcα-Sp8 | 3 | 3 | 1 | 109 |
| 279 | Neu5Gcα2-3Galβ1-4GlcNAcβ-Sp0 | 3 | 5 | 3 | 192 |
| 211 | Manα1-3(Manα1-6)Manα-Sp9 | 3 | 4 | 2 | 147 |
| 29 | [3OSO3]Galβ1-3GlcNAcβ-Sp0 | 3 | 6 | 3 | 214 |
| 15 | GalNAcβ-Sp8 | 3 | 5 | 2 | 185 |
| 9 | Neu5Acα-Sp8 | 3 | 1 | 1 | 47 |
| 320 | Neu5Acα2-8Neu5Acα2-8Neu5Acβ-Sp8 | 3 | 3 | 1 | 114 |
| 133 | Galβ1-3(Neu5Acα2-6)GalNAcα-Sp8 | 3 | 3 | 2 | 123 |
| 312 | Manα1-6(Manα1-3)Manα1-6(Manα1-3)Manβ-Sp10 | 3 | 5 | 3 | 212 |
| 235 | Neu5Acα2-3GalNAcβ1-4GlcNAcβ-Sp0 | 3 | 1 | 1 | 41 |
| 31 | [3OSO3]Galβ1-4(Fucα1-3)GlcNAc-Sp0 | 3 | 9 | 5 | 371 |
| 106 | Galα1-3(Fucα1-2)Galβ1-4Glcβ-Sp0 | 3 | 4 | 2 | 171 |
| 389 | Fucα1-2Galβ1-3GalNAcα1-3(Fucα1-2)Galβ1-4GlcNAcβ1-4GlcNAcβ-Sp0 | 2 | 5 | 3 | 220 |
| 346 | Neu5Acα2-6Galβ1-4GlcNAcβ1-2Manα1-3Manβ1-4GlcNAcβ1-4GlcNAc-Sp12 | 2 | 3 | 2 | 130 |
| 347 | Galβ1-4GlcNAcβ1-2Manα1-3Manβ1-4GlcNAcβ1-4GlcNAc-Sp12 | 2 | 3 | 2 | 142 |

Figure 3A Cont...

| | | | | |
|---|---|---|---|---|
| 187 | GlcNAcβ1-4GlcNAcβ1-4GlcNAcβ1-4GlcNAcβ-Sp8 | | | 1 | 85 |
| 305 | GlcAβ1-3GlcNAcβ-Sp8 | 2 | 2 | 3 | 262 |
| 103 | Galα1-3(Fucα1-2)Galβ1-4(Fucα1-3)GlcNAcβ-Sp0 | 2 | 3 | 2 | 128 |
| 72 | Fucα1-2Galβ1-4(Fucα1-3)GlcNAcβ-Sp8 | 2 | 5 | 3 | 213 |
| 170 | Galβ1-4Glcβ-Sp8 | 2 | 7 | 3 | 277 |
| 6 | Fucα-Sp8 | 2 | 6 | 3 | 267 |
| 292 | Neu5Acα2-3Galβ1-3GlcNAcβ1-3Galβ1-3GlcNAcβ-Sp0 | 2 | 6 | 3 | 274 |
| 184 | GlcNAcβ1-4(GlcNAcβ1-6)GalNAcα-Sp8 | 2 | 5 | 2 | 209 |
| 416 | Galα1-3(Fucα1-2)Galβ1-4(Fucα1-3)GlcNAcβ1-3GalNAc-Sp14 | 2 | 3 | 1 | 130 |
| 257 | Neu5Acα2-3Galβ1-4GlcNAcβ-Sp0 | 2 | 2 | 1 | 107 |
| 169 | Galβ1-4Glcβ-Sp0 | 2 | 4 | 2 | 186 |
| 245 | Neu5Acα2-3Galβ1-3GlcNAcβ1-3Galβ1-4GlcNAcβ-Sp0 | 2 | 6 | 3 | 285 |
| 375 | Neu5Acα2-3Galβ1-4GlcNAcβ1-4GlcNAc-Sp14 | 2 | 4 | 2 | 181 |
| 52 | GlcNAcβ1-2Manα1-3(GlcNAcβ1-2Manα1-6)Manβ1-4GlcNAcβ1-4GlcNAcβ-Sp13 | 2 | 11 | 6 | 542 |
| 316 | Neu5Acα2-3Galβ1-4GlcNAcβ1-2Manα1-3(Neu5Acα2-6Galβ1-4GlcNAcβ1-2Manα1-6)Manβ1-4GlcNAcβ1-4GlcNAcβ-Sp12 | 2 | 6 | 3 | 304 |
| 404 | Galβ1-3GlcNAcβ1-6Galβ1-4GlcNAcβ-Sp0 | 2 | 7 | 4 | 347 |
| 210 | Manα1-2Manα1-2Manα1-3(Manα1-3(Manα1-2Manα1-6)Manα1-6)Manβ1-4GlcNAcβ1-4GlcNAcβ-Sp12 | 2 | 5 | 3 | 275 |
| 100 | Galα1-2Galβ-Sp8 | 2 | 6 | 3 | 298 |
| 74 | Fucα1-2Galβ1-4GlcNAcβ1-3Galβ1-4GlcNAcβ-Sp0 | 2 | 3 | 1 | 141 |
| 266 | Neu5Acα2-6Galβ1-4GlcNAcβ-Sp0 | 2 | 1 | 0 | 38 |
| 236 | Neu5Acα2-3Galβ1-3[6OSO3]GlcNAc-Sp8 | 2 | 7 | 4 | 393 |
| 414 | GalNAcα1-3GalNAcβ1-3Galα1-4Galβ1-4Glcβ-Sp0 | 2 | 5 | 2 | 266 |
| 430 | GlcNAcβ1-2Manα1-3(GlcNAcβ1-4)(GlcNAcβ1-2Manα1-6)Manβ1-4GlcNacβ1-4GlcNAc-Sp21 | 2 | 3 | 1 | 159 |
| 64 | Fucα1-2Galβ1-3GalNAcβ1-4(Neu5Acα2-3)Galβ1-4Glcβ-Sp9 | 2 | 3 | 2 | 182 |
| 17 | GlcNAcβ-Sp8 | 2 | 4 | 2 | 227 |
| 408 | Galα1-3(Fucα1-2)Galβ1-4(Fucα1-3)Glcβ-Sp21 | 2 | 2 | 1 | 112 |

Figure 3A Cont...

| | | | | |
|---|---|---|---|---|
| 48 | [9NAc]Neu5Acα2-6Galβ1-4GlcNAcβ-Sp8 | 2 | 8 | 4 | 511 |
| 189 | GlcNAcβ1-6(Galβ1-3)GalNAcα-Sp8 | 2 | 4 | 2 | 241 |
| 144 | Galβ1-3Galβ-Sp8 | 2 | 7 | 1 | 440 |
| 225 | Neu5Acα2-8Neu5Acα2-8Neu5Acα2-3Galβ1-4Glcβ-Sp0 | 2 | 1 | 1 | 90 |
| 154 | Galβ1-4[6OSO3]Glcβ-Sp8 | 2 | 2 | 1 | 113 |
| 126 | Galβ1-3(Fucα1-4)GlcNAcβ1-3Galβ1-4GlcNAcβ-Sp0 | 1 | 3 | 2 | 235 |
| 119 | Galα1-4Galβ1-4GlcNAcβ-Sp0 | 1 | 4 | 2 | 315 |
| 226 | Neu5Acα2-8Neu5Acα2-3(GalNAcβ1-4)Galβ1-4Glcβ-Sp0 | 1 | 8 | 4 | 545 |
| 182 | GlcNAcβ1-3Galβ1-4Glcβ-Sp0 | 1 | 4 | 2 | 259 |
| 21 | [3OSO3][6OSO3]Galβ1-4[6OSO3]GlcNAcβ-Sp0 | 1 | 8 | 4 | 557 |
| 403 | Galα1-3Galβ1-4GlcNAcβ1-3GalNAcα-Sp14 | 1 | 1 | 1 | 83 |
| 437 | Galβ1-4GlcNAcβ1-4(Galβ1-4GlcNAcβ1-2)Manα1-3(GlcNAcβ1-4)(Galβ1-4GlcNAcβ1-6(Galβ1-4-GlcNAcβ1-2)Manα1-6)Manβ1-4GlcNAcβ1-4GlcNAc-Sp21 | | 3 | 2 | 264 |
| 139 | Galβ1-3GalNAcα-Sp16 | 1 | 2 | 1 | 148 |
| 329 | Neu5Acα2-3Galβ1-3(Fucα1-4)GlcNAcβ1-3Galβ1-3(Fucα1-4)GlcNAcβ-Sp0 | 1 | 5 | 2 | 394 |
| 199 | GlcAα-Sp8 | 1 | 2 | 1 | 126 |
| 131 | Galβ1-3(GlcNAcβ1-6)GalNAcα-Sp8 | 1 | 4 | 2 | 309 |
| 145 | Galβ1-3GlcNAcβ1-3Galβ1-4GlcNAcβ-Sp0 | 1 | 1 | 1 | 125 |
| 142 | Galβ1-3GalNAcβ1-4(Neu5Acα2-3)Galβ1-4Glcβ-Sp0 | 1 | 8 | 4 | 693 |
| 380 | Galβ1-3GalNAcα1-3(Fucα1-2)Galβ1-4GlcNAc-Sp0 | 1 | 6 | 3 | 505 |
| 137 | Galβ1-3GalNAcα-Sp8 | 1 | 9 | 4 | 785 |
| 422 | Galα1-3(Fucα1-2)Galβ1-3GlcNAcβ1-3GalNAc-Sp14 | 1 | 3 | 1 | 271 |
| 41 | [6OSO3]Galβ1-4Glcβ-Sp0 | 1 | 6 | 3 | 534 |
| 332 | GalNAcβ1-3Galα1-4Galβ1-4GlcNAcβ1-3Galβ1-4Glcβ-Sp0 | 1 | 3 | 2 | 339 |
| 365 | Neu5Acα2-6GlcNAcβ1-4GlcNAc-Sp21 | 1 | 7 | 4 | 700 |
| 18 | GlcN(Gc)β-Sp8 | 1 | 8 | 4 | 767 |
| 461 | Galβ1-4GlcNAcβ-(OCH2CH2)6NH2 | 1 | 8 | 4 | 827 |
| 241 | Neu5Acα2-3Galβ1-3(Neu5Acα2-6)GalNAcα-Sp8 | 1 | 5 | 3 | 542 |

Figure 3A Cont...

| | | | | |
|---|---|---|---|---|
| 172 | GlcNAcα1-6Galβ1-4GlcNAcβ-Sp8 | 1 | 6 | 3 | 632 |
| 324 | Neu5Acα2-6Galβ1-4GlcNAcβ1-2Manα1-3(Neu5Acα2-3Galβ1-4GlcNAcβ1-2Manα1-6)Manβ1-4GlcNAcβ1-4GlcNAcβ-Sp12 | 1 | 3 | 2 | 369 |
| 277 | Neu5Acβ2-6Galβ1-4GlcNAcβ-Sp8 | 1 | 2 | 1 | 212 |
| 60 | Fucα1-2Galβ1-3(Fucα1-4)GlcNAcβ-Sp8 | 1 | 6 | 3 | 723 |
| 127 | Galβ1-3(Fucα1-4)GlcNAcβ-Sp0 | 1 | 12 | 6 | 1331 |
| 220 | Fucα1-2[6OSO3]Galβ1-4[6OSO3]Glc-Sp0 | 1 | 6 | 3 | 693 |
| 271 | Neu5Acα2-6Galβ1-4Glcβ-Sp8 | 1 | 5 | 2 | 579 |
| 232 | Neu5Acα2-3(Neu5Acα2-3Galβ1-3GalNAcβ1-4)Galβ1-4Glcβ-Sp0 | 1 | 4 | 2 | 461 |
| 313 | Manα1-2Manα1-3(Manα1-6(Manα1-3)Manα1-6)Manα-Sp9 | 1 | 5 | 3 | 704 |
| 33 | [3OSO3]Galβ1-4[6OSO3]GlcNAcβ-Sp0 | 1 | 1 | 0 | 97 |
| 206 | Manα1-2Manα1-3(Manα1-2Manα1-6)Manα-Sp9 | 1 | 7 | 3 | 1001 |
| 125 | Galβ1-3(Fucα1-4)GlcNAcβ1-3Galβ1-4(Fucα1-3)GlcNAcβ-Sp0 | 1 | 7 | 4 | 1094 |
| 281 | Neu5Gcα2-3Galβ1-4GlcNAcβ-Sp0 | 1 | 4 | 2 | 623 |
| 323 | Neu5Acα2-3Galβ1-4GlcNAcβ1-2Manα1-3(Neu5Acα2-3Galβ1-4GlcNAcβ1-2Manα1-6)Manβ1-4GlcNAcβ1-4GlcNAcβ-Sp12 | 1 | 2 | 1 | 334 |
| 308 | GlcNAcβ1-4GlcNAcβ-Sp10 | 1 | 6 | 3 | 1080 |
| 91 | GalNAcα1-3GalNAcβ-Sp8 | 1 | 8 | 4 | 1474 |
| 358 | KDNα2-3Galβ1-3GalNAcα-Sp14 | 0 | 3 | 2 | 618 |
| 148 | Galβ1-3GlcNAcβ-Sp8 | 1 | 2 | 1 | 349 |
| 213 | Manα1-6(Manα1-3)Manα1-6(Manα1-2Manα1-3)(GlcNAcβ1-4)(Galβ1-4GlcNAcβ1-2Manα1-3)Manβ1-4GlcNAcβ1-4GlcNAc-Sp12 | 0 | 5 | 3 | 1005 |
| 234 | Neu5Acα2-3GalNAcα-Sp8 | 0 | 4 | 2 | 729 |
| 434 | Galβ1-4GlcNAcβ1-2Manα1-3(GlcNAcβ1-4)(Galβ1-4GlcNAcβ1-2)Manα1-6)Manβ1-4GlcNAcβ1-4GlcNAc-Sp21 | 0 | 4 | 2 | 928 |
| 451 | Fucα1-2Galβ1-4GlcNAcβ1-3(Fucα1-2Galβ1-4GlcNAcβ1-6)GalNAcα-Sp14 | 0 | 6 | 3 | 1455 |
| 455 | GalNAcβ1-4Galβ1-4Glc-b-sp0 | 0 | 5 | 2 | 1586 |
| 191 | GlcNAcβ1-6GalNAcα-Sp14 | 0 | 6 | 3 | 2681 |
| 76 | Fucα1-2Galβ1-4GlcNAcβ-Sp8 | 0 | 3 | 2 | 2272 |
| 398 | Fucα1-2Galβ1-4GlcNAcβ1-3GalNAcα-Sp14 | 0 | 3 | 2 | -16541 |

Figure 3A Cont...

| | | | | |
|---|---|---|---|---|
| 314 | Manα1-2Manα1-2Manα1-3(Manα1-2Manα1-6(Manα1-2Manα1-3)Manα1-6)Manα-Sp9 | 0 | 2 | 1 | -1269 |
| 117 | Galα1-3Galβ-Sp8 | 0 | 3 | 2 | -1951 |
| 442 | GalNAcβ1-6GalNAcβ-Sp8 | 0 | 5 | 2 | -2797 |
| 278 | Neu5Gcα2-3Galβ1-3(Fucα1-4)GlcNAcβ-Sp0 | 0 | 1 | 1 | -736 |
| 291 | Galβ1-4GlcNAcβ1-3Galβ1-3GlcNAcβ-Sp0 | 0 | 4 | 2 | -1839 |
| 16 | GlcNAcβ-Sp0 | 0 | 2 | 1 | -875 |
| 387 | GlcNAcβ1-2(GlcNAcβ1-4)Manα1-3(GlcNAcβ1-2Manα1-6)Manβ1-4GlcNAc-Sp21 | 0 | 7 | 3 | -2359 |
| 132 | Galβ1-3(GlcNAcβ1-6)GalNAc-Sp14 | 0 | 4 | 2 | -1221 |
| 62 | Fucα1-2Galβ1-3GalNAcα-Sp14 | 0 | 2 | 1 | -555 |
| 38 | [4OSO3][6OSO3]Galβ1-4GlcNAcβ-Sp0 | 0 | 3 | 1 | -726 |
| 37 | [3OSO3]Galβ-Sp8 | 0 | 4 | 2 | -919 |
| 113 | Galα1-3Galβ1-4(Fucα1-3)GlcNAcβ-Sp8 | 0 | 1 | 1 | -234 |
| 108 | Galα1-3(Fucα1-2)Galβ-Sp18 | -1 | 3 | 1 | -473 |
| 412 | Galα1-3(Fucα1-2)Galβ1-4GlcNAcβ1-3GalNAcα-Sp14 | -1 | 5 | 3 | -1008 |
| 222 | Neu5Acα2-3Galβ1-3GalNAcα-Sp14 | -1 | 4 | 2 | -793 |
| 253 | Neu5Acα2-3Galβ1-4(Fucα1-3)GlcNAcβ-Sp8 | -1 | 2 | 1 | -273 |
| 228 | Neu5Acα2-3(6-O-Su)Galβ1-4(Fucα1-3)GlcNAcβ-Sp8 | -1 | 4 | 2 | -489 |
| 200 | GlcAβ-Sp8 | -1 | 5 | 2 | -595 |
| 247 | Neu5Acα2-3Galβ1-3GlcNAcβ-Sp0 | -1 | 4 | 2 | -512 |
| 141 | Galβ1-3GalNAcβ1-3Galα1-4Galβ1-4Glcβ-Sp0 | -1 | 6 | 3 | -701 |
| 439 | Galβ1-4Galβ-Sp10 | -1 | 3 | 1 | -282 |
| 431 | GlcNAcβ1-4(GlcNAcβ1-2)Manα1-3(GlcNAcβ1-4)(GlcNAcβ1-2Manα1-6)Manβ1-4GlcNAcβ1-4GlcNAc-Sp21 | -1 | 3 | 1 | -283 |
| 163 | Galβ1-3GlcNAcβ1-3Galβ1-4Glcβ-Sp8 | -1 | 4 | 2 | -353 |
| 114 | Galα1-3Galβ1-3GlcNAcβ-Sp0 | -1 | 2 | 1 | -149 |
| 35 | [3OSO3]Galβ1-4GlcNAcβ-Sp0 | -1 | 5 | 2 | -414 |
| 265 | Neu5Acα2-6Galβ1-4[6OSO3]GlcNAcβ-Sp8 | -1 | 4 | 2 | -298 |
| 156 | Galβ1-4GalNAcβ1-3(Fucα1-2)Galβ1-4GlcNAcβ-Sp8 | -1 | 3 | 1 | -199 |

Figure 3A Cont...

| 167 | Galβ1-4GlcNAcβ-Sp0 | -1 | 5 | 2 | -390 |
|---|---|---|---|---|---|
| 138 | Galβ1-3GalNAcα-Sp14 | -1 | 4 | 2 | -257 |
| 71 | Fucα1-2Galβ1-4(Fucα1-3)GlcNAcβ-Sp0 | -1 | 2 | 2 | -261 |
| 75 | Fucα1-2Galβ1-4GlcNAcβ-Sp0 | -2 | 2 | 1 | -144 |
| 157 | Galβ1-4GlcNAcβ1-3GalNAcα-Sp8 | -2 | 4 | 2 | -263 |
| 4 | GalNAcα-Sp8 | -2 | 6 | 3 | -339 |
| 366 | Neu5Acα2-6GlcNAcβ1-4GlcNAcβ1-4GlcNAc-Sp21 | -2 | 2 | 1 | -131 |
| 116 | Galα1-3Galβ1-4Glcβ-Sp0 | -2 | 5 | 3 | -301 |
| 174 | GlcNAcβ1-3(GlcNAcβ1-6)GalNAcα-Sp8 | -2 | 5 | 2 | -251 |
| 26 | [3OSO3]Galβ1-4[6OSO3]Glcβ-Sp8 | -2 | 3 | 2 | -173 |
| 115 | Galα1-3Galβ1-4GlcNAcβ-Sp8 | -2 | 6 | 3 | -268 |
| 197 | Glcβ1-6Glcβ-Sp8 | -2 | 1 | 1 | -66 |
| 180 | GlcNAcβ1-3Galβ1-4GlcNAcβ-Sp8 | -2 | 3 | 1 | -119 |
| 14 | Manβ-Sp8 | -2 | 3 | 1 | -127 |
| 24 | [3OSO3]Galβ1-4Glcβ-Sp8 | -3 | 2 | 1 | -60 |
| 201 | GlcAβ1-3Galβ-Sp8 | -3 | 3 | 1 | -110 |
| 440 | Galβ1-6Galβ-Sp10 | -3 | 3 | 1 | -104 |
| 203 | KDNα2-3Galβ1-3GlcNAcβ-Sp0 | -3 | 3 | 1 | -98 |
| 46 | [6OSO3]GlcNAcβ-Sp8 | -3 | 5 | 3 | -170 |
| 45 | Neu5Acα2-3[6OSO3]Galβ1-4GlcNAcβ-Sp8 | -3 | 4 | 2 | -129 |
| 150 | Galβ1-4(Fucα1-3)GlcNAcβ-Sp8 | -3 | 7 | 4 | -220 |
| 90 | GalNAcα1-3(Fucα1-2)Galβ-Sp18 | -3 | 8 | 4 | -253 |
| 462 | Galα1-3(Fucα1-2)Galβ1-3GalNAcα-Sp8 | -4 | 5 | 3 | -147 |
| 122 | Galα1-4GlcNAcβ-Sp8 | -4 | 4 | 2 | -113 |
| 287 | Galβ1-3GlcNAcβ1-3Galβ1-3GlcNAcβ-Sp0 | -4 | 5 | 3 | -117 |
| 311 | Manα1-6Manβ-Sp10 | -4 | 3 | 1 | -121 |
| 171 | GlcNAcα1-3Galβ1-4GlcNAcβ-Sp8 | -5 | 5 | 2 | -55 |
| 47 | [9NAc]Neu5Acα-Sp8 | -5 | 5 | 2 | -93 |

Figure 3A Cont...

| 11 | Neu5Acβ-Sp8 | -7 | 6 | 3 | -86 |
| --- | --- | --- | --- | --- | --- |
| 267 | Neu5Acα2-6Galβ1-4GlcNAcβ-Sp8 | -7 | 2 | 1 | -24 |

Figure 3A Cont...

| Chart Number | Glycan Structure | Average | StDEV | SEM | % CV |
|---|---|---|---|---|---|
| 66 | Fucα1-2Galβ1-3GlcNAcβ1-3Galβ1-4Glcβ-Sp10 | 758 | 92 | 46 | 12 |
| 68 | Fucα1-2Galβ1-3GlcNAcβ-Sp8 | 585 | 221 | 111 | 38 |
| 67 | Fucα1-2Galβ1-3GlcNAcβ-Sp0 | 482 | 64 | 32 | 13 |
| 421 | Fucα1-2Galβ1-3GlcNAcβ1-3GalNAc-Sp14 | 446 | 49 | 24 | 11 |
| 65 | Fucα1-2Galβ1-3GlcNAcβ1-3Galβ1-4Glcβ-Sp8 | 193 | 80 | 40 | 41 |
| 25 | [3OSO3]Galβ1-4[6OSO3]Glcβ-Sp0 | 129 | 32 | 16 | 25 |
| 341 | GlcNAcα1-4Galβ1-4GlcNAcβ1-3Galβ1-4GlcNAcβ-Sp0 | 43 | 27 | 13 | 62 |
| 353 | Galβ1-3(Fucα1-4)GlcNAcβ1-2Manα1-3(Galβ1-3(Fucα1-4)GlcNAcβ1-2Manα1-6)Manβ1-4GlcNAcβ1-4GlcNAcβ-Sp19 | 35 | 10 | 5 | 27 |
| 415 | Fucα1-2Galβ1-4(Fucα1-3)GlcNAcβ1-3GalNAcα-Sp14 | 29 | 21 | 11 | 72 |
| 54 | Neu5Acα2-6Galβ1-4GlcNAcβ1-2Manα1-3(Neu5Acα2-6Galβ1-4GlcNAcβ1-2Manα1-6)Manβ1-4GlcNAcβ-N(LT)AVL | 21 | 7 | 4 | 33 |
| 377 | Neu5Acα2-3Galβ1-4(Fucα1-3)GlcNAcβ1-3GalNAcα-Sp14 | 17 | 17 | 9 | 100 |
| 374 | Fucα1-2Galβ1-3(Fucα1-4)GlcNAcβ1-2Manα1-3(Fucα1-2Galβ1-3(Fucα1-4)GlcNAcβ1-2Manα1-6)Manβ1-4GlcNAcβ1-4GlcNAcβ-Sp19 | 16 | 8 | 4 | 48 |
| 358 | KDNα2-3Galβ1-3GalNAcα-Sp14 | 16 | 12 | 6 | 72 |
| 327 | Neu5Ac(9Ac)α2-3Galβ1-3GlcNAcβ-Sp0 | 15 | 13 | 7 | 86 |
| 417 | GalNAcα1-3(Fucα1-2)Galβ1-4(Fucα1-3)GlcNAcβ1-3GalNAc-Sp14 | 15 | 4 | 2 | 28 |
| 449 | Galβ1-4(Fucα1-3)GlcNAcβ1-6GalNAc-Sp14 | 14 | 12 | 6 | 84 |
| 139 | Galβ1-3GalNAcα-Sp16 | 14 | 7 | 3 | 49 |
| 47 | [9NAc]Neu5Acα-Sp8 | 14 | 11 | 5 | 76 |
| 319 | Neu5Acα2-8Neu5Acβ-Sp17 | 13 | 7 | 4 | 58 |
| 386 | Galβ1-4GlcNAcβ1-2(Galβ1-4GlcNAcβ1-4)Manα1-3(Galβ1-4GlcNAcβ1-2(Galβ1-4GlcNAcβ1-6)Manα1-6)Manβ1-4GlcNAcβ1-4GlcNAcβ-Sp21 | 13 | 11 | 6 | 89 |
| 297 | Galβ1-3(Neu5Acα2-3Galβ1-4(Fucα1-3)GlcNAcβ1-6)GalNAcα-Sp14 | 13 | 11 | 5 | 84 |
| 197 | Glcβ1-6Glcβ-Sp8 | 13 | 4 | 2 | 30 |
| 384 | Fucα1-2Galβ1-3(Fucα1-4)GlcNAcβ1-3(Galβ1-4(Fucα1-3)GlcNAcβ1-6)Galβ1-4Glc-Sp21 | 12 | 10 | 5 | 81 |
| 339 | GlcNAcα1-4Galβ1-4GlcNAcβ1-3Galβ1-3GlcNAcβ-Sp0 | 12 | 9 | 4 | 72 |

Figure 4a

| | | | | |
|---|---|---|---|---|
| 88 | GlcNAcβ1-3Galβ1-3GalNAcα-Sp8 | 12 | 10 | 5 | 84 |
| 10 | Neu5Acα-Sp11 | 12 | 11 | 6 | 94 |
| 83 | GalNAcα1-3(Fucα1-2)Galβ1-4(Fucα1-3)GlcNAcβ-Sp0 | 12 | 5 | 2 | 41 |
| 136 | Galβ1-3(Neu5Acα2-6)GlcNAcβ1-4Galβ1-4Glcβ-Sp10 | 12 | 9 | 4 | 76 |
| 401 | Galα1-4Galβ1-3GlcNAcβ1-2Manα1-3(Galα1-4Galβ1-3GlcNAcβ1-2Manα1-6)Manβ1-4GlcNAcβ1-4GlcNAcβ-Sp19 | 12 | 3 | 2 | 30 |
| 252 | Neu5Acα2-3Galβ1-4(Fucα1-3)GlcNAcβ-Sp0 | 11 | 4 | 2 | 31 |
| 344 | Neu5Acα2-6Galβ1-4GlcNAcβ1-2Manα1-3(Manα1-6)Manβ1-4GlcNAcβ1-4GlcNAc-Sp12 | 11 | 5 | 2 | 44 |
| 305 | GlcAβ1-3GlcNAcβ-Sp8 | 11 | 10 | 5 | 89 |
| 213 | Manα1-6(Manα1-3)Manα1-6(Manα1-2Manα1-3)Manβ1-4GlcNAcβ1-4GlcNAcβ-Sp12 | 11 | 13 | 6 | 117 |
| 362 | Galα1-3Galβ1-4GlcNAcβ1-2Manα1-3(Galα1-3Galβ1-4GlcNAcβ1-2Manα1-6)Manβ1-4GlcNAcβ1-4GlcNAcβ-Sp20 | 11 | 8 | 4 | 71 |
| 434 | Galβ1-4GlcNAcβ1-2Manα1-3(GlcNAcβ1-4)(Galβ1-4GlcNAcβ1-2)Manα1-6)Manβ1-4GlcNAcβ1-4GlcNAc-Sp21 | 11 | 5 | 3 | 51 |
| 338 | GlcNAcα1-4Galβ1-3GlcNAcβ-Sp0 | 11 | 5 | 3 | 47 |
| 289 | Galβ1-4(Fucα1-3)[6OSO3]Glc-Sp0 | 11 | 3 | 1 | 28 |
| 336 | GlcNAcα1-4Galβ1-4GlcNAcβ1-3Galβ1-4GlcNAcβ-Sp0 | 11 | 13 | 6 | 119 |
| 387 | GlcNAcβ1-2(GlcNAcβ1-4)Manα1-3(GlcNAcβ1-2Manα1-6)Manβ1-4GlcNAcβ1-4GlcNAc-Sp21 | 10 | 4 | 2 | 37 |
| 286 | Galβ1-3(Neu5Acα2-3Galβ1-4GlcNAcβ1-6)GalNAcα-Sp14 | 10 | 7 | 3 | 65 |
| 254 | Neu5Acα2-3Galβ1-4(Fucα1-3)GlcNAcβ1-3Galβ-Sp8 | 10 | 6 | 3 | 59 |
| 180 | GlcNAcβ1-3Galβ1-4GlcNAcβ-Sp8 | 10 | 19 | 10 | 189 |
| 394 | Galα1-3Galβ1-3(Fucα1-4)GlcNAcβ1-2Manα1-3(Galα1-3Galβ1-3(Fucα1-4)GlcNAcβ1-2Manα1-6)Manβ1-4GlcNAcβ1-4GlcNAc-Sp19 | 10 | 1 | 1 | 12 |
| 397 | Neu5Acα2-3Galβ1-3GlcNAcβ1-3GalNAcα-Sp14 | 10 | 6 | 3 | 62 |
| 84 | [3OSO3]Galβ1-4(Fucα1-3)Glc-Sp0 | 10 | 8 | 4 | 86 |
| 335 | Neu5Acα2-3Galβ1-3(Galβ1-4(Fucα1-3)GlcNAcβ1-6)GalNAc-Sp14 | 10 | 5 | 3 | 55 |
| 445 | Fucα1-2Galβ1-4GlcNAcβ1-2(Fucα1-2Galβ1-4GlcNAcβ1-4)Manα1-3(Fucα1-2Galβ1-4 GlcNAcβ1-2Manα1-6)Manβ1-4GlcNAcβ1-4GlcNAcβ-Sp12 | 10 | 8 | 4 | 79 |
| 418 | Galβ1-4(Fucα1-3)GlcNAcβ1-2Manα1-3(Galβ1-4(Fucα1-3)GlcNAcβ1-2Manα1-6)Manβ1-4GlcNAcβ1-4(Fucα1-6)GlcNAcβ-Sp22 | 9 | 8 | 4 | 91 |
| 281 | Neu5Gcα2-3Galβ1-4GlcNAcβ-Sp0 | 9 | 2 | 1 | 17 |

Figure 4a Cont...

| | | | | | |
|---|---|---|---|---|---|
| 20 | GlcNAcβ1-3(GlcNAcβ1-4)(GlcNAcβ1-6)GlcNAc-Sp8 | 9 | 5 | 3 | 56 |
| 371 | Galα1-3Galβ1-4(Fucα1-3)GlcNAcβ1-2Manα1-3(Galα1-3Galβ1-4(Fucα1-3)GlcNAcβ1-2Manα1-6)Manβ1-4GlcNAcβ1-4GlcNAcβ-Sp20 | 9 | 2 | 1 | 16 |
| 334 | GalNAcα1-3(Fucα1-2)Galβ1-4GlcNAcβ1-3Galβ1-4GlcNAcβ1-3Galβ1-4GlcNAcβ-Sp0 | 9 | 5 | 3 | 60 |
| 234 | Neu5Acα2-3GalNAcα-Sp8 | 9 | 4 | 2 | 46 |
| 455 | GalNAcβ1-4Galβ1-4Glc-b-sp0 | 9 | 7 | 4 | 78 |
| 64 | Fucα1-2Galβ1-3GalNAcβ1-4(Neu5Acα2-3)Galβ1-4Glcβ-Sp9 | 9 | 7 | 3 | 76 |
| 55 | Neu5Acα2-6Galβ1-4GlcNAcβ1-2Manα1-3(Neu5Acα2-6Galβ1-4GlcNAcβ1-2Manα1-6)Manβ1-4GlcNAcβ1-4GlcNAcβ-Sp8 | 9 | 6 | 3 | 63 |
| 378 | (GalNAcβ1-4GlcNAcβ1-2Manα1-6)GalNAcβ1-4GlcNAcβ1-2Manα1-3Manβ1-4GlcNAcβ1-4GlcNAc-Sp12 | 9 | 2 | 1 | 21 |
| 195 | Glcα1-6Glcα1-6Glcβ-Sp8 | 9 | 3 | 2 | 37 |
| 268 | Neu5Acα2-6Galβ1-4GlcNAcβ1-3Galβ1-4(Fucα1-3)GlcNAcβ1-3Galβ1-4(Fucα1-3)GlcNAcβ-Sp12 | 8 | 7 | 4 | 83 |
| 51 | GlcNAcβ1-2Manα1-3(GlcNAcβ1-2Manα1-6)Manβ1-4GlcNAcβ1-4GlcNAcβ-Sp0 | 8 | 5 | 3 | 65 |
| 258 | Neu5Acα2-3Galβ1-4GlcNAcβ-Sp8 | 8 | 8 | 4 | 98 |
| 422 | Galα1-3(Fucα1-2)Galβ1-3GlcNAcβ1-3GalNAc-Sp14 | 8 | 4 | 2 | 51 |
| 201 | GlcAβ1-3Galβ-Sp8 | 8 | 3 | 1 | 34 |
| 411 | Neu5Acα2-3Galβ1-3GalNAcβ1-4(Neu5Acα2-8Neu5Acα2-3)Galβ1-4Glcβ-Sp0 | 8 | 4 | 2 | 55 |
| 74 | Fucα1-2Galβ1-4GlcNAcβ1-3Galβ1-4GlcNAcβ1-3Galβ1-4GlcNAcβ-Sp0 | 8 | 10 | 5 | 126 |
| 255 | Neu5Acα2-3Galβ1-4(Fucα1-3)GlcNAcβ1-2Manα1-6)Manβ1-4GlcNAcβ-Sp8 | 8 | 4 | 2 | 55 |
| 283 | Neu5Gcα2-6GalNAcα-Sp0 | 8 | 6 | 3 | 80 |
| 14 | Manβ-Sp8 | 8 | 8 | 4 | 111 |
| 231 | Neu5Acα2-3(GalNAcβ1-4)Galβ1-4Glcβ-Sp0 | 8 | 8 | 4 | 105 |
| 381 | Galβ1-3GlcNAcβ1-3(Galβ1-3GlcNAcβ1-3Galβ1-4GlcNAcβ1-6)Galβ1-4Glcβ-Sp0 | 8 | 4 | 2 | 48 |
| 379 | Galβ1-3GalNAcα1-3(Fucα1-2)Galβ1-4Glc-Sp0 | 7 | 7 | 4 | 97 |
| 183 | GlcNAcβ1-4-MDPLys | 7 | 3 | 1 | 35 |
| 217 | [3OSO3]Galβ1-4(Fucα1-3)[6OSO3]GlcNAc-Sp8 | 7 | 5 | 2 | 66 |
| 238 | Neu5Acα2-3Galβ1-3(Fucα1-4)GlcNAcβ1-3Galβ1-4(Fucα1-3)GlcNAcβ-Sp0 | 7 | 4 | 2 | 51 |
| 237 | Neu5Acα2-3Galβ1-3(Fucα1-4)GlcNAcβ1-4)GlcNAcβ-Sp8 | 7 | 5 | 3 | 69 |

Figure 4a Cont...

| | | | | |
|---|---|---|---|---|
| 357 | KDNα2-3Galβ1-4Glc-Sp0 | 7 | 5 | 2 | 64 |
| 409 | Neu5Acα2-6Galβ1-3GlcNAcβ1-3(Galβ1-4GlcNAcβ1-6)Galβ1-4Glc-Sp21 | 7 | 2 | 1 | 32 |
| 222 | Neu5Acα2-3Galβ1-3GalNAcα-Sp14 | 7 | 4 | 2 | 59 |
| 348 | Galβ1-4GlcNAcβ1-2Manα1-6Manβ1-4GlcNAc-Sp12 | 7 | 11 | 5 | 149 |
| 100 | Galα1-2Galβ-Sp8 | 7 | 5 | 3 | 72 |
| 437 | Galβ1-4GlcNAcβ1-4(Galβ1-4GlcNAcβ1-2)Manα1-3(GlcNAcβ1-4)(Galβ1-4GlcNAcβ1-6(Galβ1-4-GlcNAcβ1-2)Manα1-6)Manβ1-4GlcNAcβ1-4GlcNAc-Sp21 | 7 | 4 | 2 | 60 |
| 30 | [3OSO3]Galβ1-3GlcNAcβ-Sp8 | 7 | 5 | 3 | 74 |
| 423 | GalNAcα1-3(Fucα1-2)Galβ1-3GlcNAcβ1-3GalNAc-Sp14 | 7 | 2 | 1 | 31 |
| 313 | Manα1-2Manα1-3(Manα1-2Manα1-6(Manα1-3)Manα1-6)Manα-Sp9 | 7 | 7 | 3 | 95 |
| 369 | GalNAcα1-3(Fucα1-2)Galβ1-4GlcNAcβ1-2Manα1-3(GalNAcα1-3(Fucα1-2)Galβ1-4GlcNAcβ1-2Manα1-6)Manβ1-4GlcNAcβ1-4GlcNAc-Sp20 | 7 | 3 | 2 | 48 |
| 39 | [4OSO3]Galβ1-4GlcNAcβ-Sp8 | 7 | 2 | 1 | 31 |
| 96 | GalNAcβ1-3Galα1-4Galβ1-4GlcNAcβ-Sp0 | 7 | 9 | 4 | 126 |
| 367 | Fucα1-2Galβ1-3GlcNAcβ1-3(Galβ1-4(Fucα1-3)GlcNAcβ1-6)Galβ1-4Glc-Sp21 | 7 | 6 | 3 | 85 |
| 444 | [6OSO3]Galβ1-3[6OSO3]GlcNAc-Sp0 | 7 | 5 | 2 | 74 |
| 128 | Galβ1-3(Fucα1-4)GlcNAcβ-Sp8 | 7 | 13 | 6 | 191 |
| 193 | Glcα1-4Glcβ-Sp8 | 7 | 13 | 6 | 191 |
| 314 | Manα1-2Manα1-2Manα1-3(Manα1-2Manα1-6(Manα1-3)Manα1-6)Manα-Sp9 | 7 | 7 | 4 | 107 |
| 229 | Neu5Acα2-3(GalNAcβ1-4)Galβ1-4GlcNAcβ-Sp0 | 7 | 4 | 2 | 58 |
| 156 | Galβ1-3GalNAcβ1-3(Fucα1-2)Galβ1-4GlcNAcβ-Sp8 | 7 | 5 | 3 | 77 |
| 291 | Galβ1-4GlcNAcβ1-3Galβ1-3GlcNAcβ-Sp0 | 7 | 3 | 2 | 49 |
| 86 | GalNAcα1-3(Fucα1-2)Galβ1-4GlcNAcβ-Sp8 | 7 | 1 | 0 | 15 |
| 158 | Galβ1-4GlcNAcβ1-3GalNAcα-Sp14 | 7 | 5 | 2 | 72 |
| 408 | Galα1-3(Fucα1-2)Galβ1-4(Fucα1-3)Glcβ-Sp21 | 7 | 5 | 2 | 70 |
| 157 | Galβ1-4GlcNAcβ1-3GalNAcα-Sp8 | 6 | 7 | 4 | 114 |
| 453 | GalNAcα1-3Fucα1-2Galβ1-4GlcNAcβ1-3(GalNAcα1-3Fucα1-2Galβ1-4GlcNAcβ1-6)GalNAc-Sp14 | 6 | 3 | 1 | 40 |
| 108 | Galα1-3(Fucα1-2)Galβ-Sp18 | 6 | 6 | 3 | 100 |

Figure 4a Cont...

| | | | | | |
|---|---|---|---|---|---|
| 270 | Neu5Acα2-6Galβ1-4Glcβ-Sp0 | 6 | 4 | 2 | 66 |
| 278 | Neu5Gcα2-3Galβ1-3(Fucα1-4)GlcNAcβ-Sp0 | 6 | 4 | 2 | 65 |
| 458 | Neu5Acα2-6GlcNAcβ1-4GlcNAcβ1-6(Fucα1-2Galβ1-3)GlcNAcβ1-3)Galβ-4Glc-Sp21 | 6 | 5 | 2 | 80 |
| 166 | Galβ1-3(GlcNAcβ1-6)GalNAc-Sp14 | 6 | 5 | 3 | 88 |
| 363 | Manα1-3(Galβ1-4GlcNAcβ1-2Manα1-6)Manβ1-4GlcNAcβ1-4GlcNAc-Sp12 | 6 | 4 | 2 | 61 |
| 115 | Galα1-3Galβ1-4GlcNAcβ-Sp0 | 6 | 6 | 3 | 96 |
| 245 | Neu5Acα2-3Galβ1-3GlcNAcβ1-3Galβ1-4GlcNAcβ-Sp0 | 6 | 7 | 4 | 121 |
| 219 | Fucα1-2Galβ1-4[6OSO3]GlcNAc-Sp8 | 6 | 15 | 8 | 255 |
| 112 | Galα1-3GalNAcβ-Sp8 | 6 | 4 | 2 | 59 |
| 93 | GalNAcα1-4(Fucα1-2)Galβ1-4GlcNAcβ-Sp8 | 6 | 2 | 1 | 37 |
| 429 | Galβ1-4GlcNAcβ1-3Galβ1-4(Fucα1-3)GlcNAcβ1-6)Galβ1-4Glc-Sp21 | 6 | 10 | 5 | 165 |
| 290 | Galβ1-4(Fucα1-3)GlcNAcβ1-3Galβ1-3(Fucα1-4)GlcNAcβ-Sp0 | 6 | 2 | 1 | 31 |
| 134 | Galβ1-3(Neu5Acα2-6)GalNAcα-Sp14 | 6 | 6 | 3 | 101 |
| 4 | GalNAcα-Sp8 | 6 | 4 | 2 | 59 |
| 226 | Neu5Acα2-8Neu5Acα2-3(GalNAcβ1-4)Galβ1-4Glcβ-Sp0 | 6 | 8 | 4 | 135 |
| 146 | Galβ1-3GlcNAcβ1-3Galβ1-4Glcβ-Sp10 | 6 | 2 | 1 | 41 |
| 91 | GalNAcα1-3GalNAcβ-Sp8 | 6 | 4 | 2 | 68 |
| 138 | Galβ1-3GalNAcα-Sp14 | 6 | 8 | 4 | 138 |
| 103 | Galα1-3(Fucα1-2)Galβ1-4(Fucα1-3)GlcNAcβ-Sp0 | 6 | 1 | 1 | 24 |
| 405 | Galβ1-3GlcNAcα1-6Galβ1-4GlcNAcβ-Sp0 | 6 | 6 | 3 | 102 |
| 31 | [3OSO3]Galβ1-4(Fucα1-3)GlcNAc-Sp0 | 6 | 2 | 1 | 43 |
| 57 | Neu5Acα2-6Galβ1-4GlcNAcβ1-2Manα1-3(Neu5Acα2-6Galβ1-4GlcNAcβ1-2Manα1-6)Manβ1-4GlcNAcβ1-4GlcNAcβ-Sp13 | 6 | 5 | 2 | 82 |
| 174 | GlcNAcβ1-3(GlcNAcβ1-6)GalNAcα-Sp8 | 6 | 4 | 2 | 75 |
| 299 | Galβ1-4GlcNAcβ1-2Manα1-3(Neu5Acα2-6Galβ1-4GlcNAcβ1-2Manα1-6)Manβ1-4GlcNAcβ1-4GlcNAcβ-Sp12 | 6 | 6 | 3 | 112 |
| 310 | HOOC(CH3)CH-3-O-GlcNAcβ1-4GlcNAc-Sp10 | 6 | 6 | 3 | 99 |
| 463 | Galα1-3(Fucα1-2)Galβ1-3GalNAcb-Sp8 | 6 | 7 | 4 | 131 |

Figure 4a Cont...

| | | | | | |
|---|---|---|---|---|---|
| 241 | Neu5Acα2-3Galβ1-3(Neu5Acα2-6)GalNAcα-Sp8 | 6 | 5 | 3 | 92 |
| 82 | GalNAcα1-3(Fucα1-2)Galβ1-3GlcNAcβ-Sp0 | 6 | 4 | 2 | 69 |
| 149 | Galβ1-4(Fucα1-3)GlcNAcβ-Sp0 | 6 | 4 | 2 | 68 |
| 337 | GlcNAcα1-4Galβ1-4GlcNAcβ-Sp0 | 6 | 3 | 2 | 63 |
| 282 | Neu5Gcα2-3Galβ1-4Glcβ-Sp0 | 6 | 7 | 3 | 123 |
| 8 | Rhaα-Sp8 | 5 | 5 | 2 | 90 |
| 459 | GalNAcα1-3(Fucα1-2)Galβ1-3GlcNAcβ1-2Manα1-6(GalNAcα1-3(Fucα1-2)Galβ1-3GlcNAcβ1-2Manα1-3)Manβ1-4GlcNAcβ1-4(Fucα1-6)GlcNAcβ-Sp22 | 5 | 6 | 3 | 101 |
| 432 | GlcNAcβ1-2Manα1-3(GlcNAcβ1-4)(GlcNAcβ1-6(GlcNAcβ1-2)Manα1-6)Manβ1-4GlcNAcβ1-4GlcNAc-Sp21 | 5 | 4 | 2 | 68 |
| 420 | GlcNAcβ1-2Manα1-3(GlcNAcβ1-2(GlcNAcβ1-6)Manα1-6)Manβ1-4GlcNAcβ1-4GlcNAcβ-Sp19 | 5 | 4 | 2 | 64 |
| 446 | Fucα1-2Galβ1-4(Fucα1-3)GlcNAcβ1-2(Fucα1-2Galβ1-4(Fucα1-3)GlcNAcβ1-4)Manα1-3(Fucα1-2Galβ1-4(Fucα1-3)GlcNAcβ1-2Manα1-6)Manβ1-4GlcNAcβ1-4GlcNAcβ-Sp12 | 5 | 2 | 1 | 44 |
| 428 | Fucα1-2Galβ1-3GlcNAcβ1-2Manα1-6(Galβ1-3(Fucα1-4)GlcNAcβ1-6)Galβ1-4Glc-Sp21 | 5 | 2 | 1 | 44 |
| 412 | Galα1-3(Fucα1-2)Galβ1-4GlcNAcβ1-3GalNAcα-Sp14 | 5 | 6 | 3 | 116 |
| 390 | Galβ1-3GlcNAcβ1-3Galα1-6Galβ1-4Glcβ-Sp8 | 5 | 4 | 2 | 74 |
| 406 | GalNAcβ1-3Galα1-6GlcNAcβ1-4GlcNAcβ-Sp8 | 5 | 7 | 3 | 129 |
| 366 | Neu5Acα2-6GlcNAcβ1-4GlcNAcβ1-4GlcNAc-Sp21 | 5 | 6 | 3 | 113 |
| 38 | [4OSO3][6OSO3]Galβ1-4GlcNAcβ-Sp0 | 5 | 6 | 3 | 111 |
| 361 | Fucα1-2Galβ1-4(Fucα1-3)GlcNAcβ1-2Manα1-3(Fucα1-2Galβ1-4(Fucα1-3)GlcNAcβ1-2Manα1-6)Manβ1-4GlcNAcβ1-4GlcNAβ-Sp20 | 5 | 5 | 2 | 88 |
| 132 | Galβ1-3(GlcNAcβ1-6)GalNAcα-Sp14 | 5 | 6 | 3 | 104 |
| 346 | Neu5Acα2-6Galβ1-4Manα1-3Manβ1-4GlcNAcβ1-4GlcNAc-Sp12 | 5 | 6 | 3 | 110 |
| 451 | Fucα1-2Galβ1-4GlcNAcβ1-3(Fucα1-2Galβ1-4GlcNAcβ1-6)GalNAcα-Sp14 | 5 | 5 | 3 | 97 |
| 16 | GlcNAcβ-Sp0 | 5 | 5 | 3 | 104 |
| 165 | Galβ1-3(Galβ1-4GlcNAcβ1-6)GalNAcα-Sp8 | 5 | 7 | 4 | 141 |
| 302 | Galβ1-4GlcNAcα1-6Galβ1-4GlcNAcβ-Sp0 | 5 | 7 | 3 | 134 |
| 76 | Fucα1-2Galβ1-4(Fucα1-6)GlcNAcβ-Sp8 | 5 | 13 | 7 | 256 |
| 456 | GalNAcα1-3(Fucα1-2)Galβ1-4GlcNAcβ1-2Manα1-6(GalNAcα1-3(Fucα1-2)Galβ1-4GlcNAcβ1-2Manα1-3)Manβ1-4GlcNAcβ1-4(Fucα1-6)GlcNAcβ-Sp22 | 5 | 3 | 2 | 67 |

Figure 4a Cont...

| | | | | | |
|---|---|---|---|---|---|
| 116 | Galα1-3Galβ1-4Glcβ-Sp0 | 5 | 3 | 6 | 239 |
| 232 | Neu5Acα2-3(Neu5Acα2-3Galβ1-3GalNAcβ1-4)Galβ1-4Glcβ-Sp0 | 5 | 3 | 2 | 65 |
| 121 | Galα1-4Galβ1-4Glcβ-Sp0 | 5 | 7 | 3 | 133 |
| 240 | Neu5Acα2-3Galβ1-3[6OSO3]GalNAcα-Sp8 | 5 | 4 | 2 | 83 |
| 443 | [6OSO3]Galβ1-3GlcNAcβ-Sp0 | 5 | 3 | 1 | 58 |
| 312 | Manα1-6(Manα1-3)Manα1-6(Manα1-3)Manβ-Sp10 | 5 | 3 | 1 | 55 |
| 430 | GlcNAcβ1-2Manα1-3(GlcNAcβ1-4)(GlcNAcβ1-2Manα1-6)Manβ1-4GlcNAc-Sp21 | 5 | 3 | 2 | 61 |
| 436 | Galβ1-4GlcNAcβ1-2Manα1-3(GlcNAcβ1-4)(Galβ1-4GlcNAcβ1-2Manα1-6)Manβ1-4GlcNAcβ1-4GlcNAc-Sp21 | 5 | 6 | 3 | 117 |
| 191 | GlcNAcβ1-6GalNAcα-Sp14 | 5 | 6 | 3 | 115 |
| 389 | Fucα1-2Galβ1-3GalNAcα1-3(Fucα1-2)Galβ1-4GlcNAcβ-Sp0 | 5 | 5 | 2 | 92 |
| 199 | GlcAα-Sp8 | 5 | 6 | 3 | 120 |
| 372 | GalNAcα1-3(Fucα1-2)Galβ1-3GlcNAcβ1-2Manα1-3(Fucα1-2)Galβ1-3GlcNAcβ1-2Manα1-6)GlcNAcβ1-4GlcNAcβ-Sp20 | 5 | 5 | 3 | 108 |
| 242 | Neu5Acα2-3Galβ1-3(Neu5Acα2-6)GalNAcα-Sp14 | 5 | 9 | 5 | 193 |
| 21 | [3OSO3][6OSO3]Galβ1-4[6OSO3]GlcNAcβ-Sp0 | 5 | 7 | 4 | 144 |
| 419 | Fucα1-2Galβ1-4GlcNAcβ1-2Manα1-3(Fucα1-2Galβ1-4GlcNAcβ1-2Manα1-6)Manβ1-4GlcNAcβ1-4(Fucα1-6)GlcNAcβ-Sp22 | 5 | 4 | 2 | 74 |
| 388 | Fucα1-2Galβ1-3GalNAcα1-3(Fucα1-2)Galβ1-4Glcβ-Sp0 | 5 | 3 | 2 | 71 |
| 164 | Galβ1-4GlcNAcβ1-6(Galβ1-3)GalNAcα-Sp8 | 5 | 7 | 3 | 146 |
| 129 | Galβ1-3(Fucα1-4)GlcNAc-Sp8 | 5 | 1 | 1 | 24 |
| 285 | Neu5Gcα-Sp8 | 5 | 2 | 1 | 45 |
| 178 | GlcNAcβ1-3Galβ-Sp8 | 5 | 7 | 3 | 143 |
| 321 | Neu5Gcβ2-6Galβ1-4GlcNAc-Sp8 | 5 | 5 | 2 | 104 |
| 280 | Neu5Gcα2-3Galβ1-4(Fucα1-3)GlcNAcβ-Sp0 | 5 | 10 | 5 | 213 |
| 332 | GalNAcβ1-3Galα1-4Galβ1-4GlcNAcβ1-3Galβ1-4Glcβ-Sp0 | 5 | 7 | 4 | 152 |
| 404 | Galβ1-3GlcNAcβ1-6GalNAcβ1-4GlcNAcβ-Sp0 | 5 | 5 | 2 | 106 |
| 182 | GlcNAcβ1-3Galβ1-4Glcβ-Sp0 | 5 | 3 | 1 | 54 |
| 92 | GalNAcα1-3Galβ-Sp8 | 5 | 10 | 5 | 214 |

Figure 4a Cont...

| | | | | |
|---|---|---|---|---|
| 60 | Fucα1-2Galβ1-3(Fucα1-4)GlcNAcβ-Sp8 | | | 85 |
| 27 | [3OSO3]Galβ1-3(Fucα1-4)GlcNAcβ-Sp8 | 5 | 5 | 108 |
| 73 | Fucα1-2Galβ1-4GlcNAcβ1-3Galβ1-4GlcNAcβ-Sp0 | 5 | 4 | 77 |
| 155 | Galβ1-4GalNAcα1-3(Fucα1-2)Galβ1-4GlcNAcβ-Sp8 | 5 | 3 | 56 |
| 160 | Galβ1-4GlcNAcβ1-3Galβ1-4GlcNAcβ1-3Galβ1-4GlcNAcβ-Sp0 | 4 | 4 | 90 |
| 176 | GlcNAcβ1-3GalNAcα-Sp8 | 4 | 3 | 75 |
| 133 | Galβ1-3(Neu5Acα2-6)GalNAcα-Sp8 | 4 | 4 | 93 |
| 107 | Galα1-3(Fucα1-2)Galβ-Sp8 | 4 | 3 | 59 |
| 249 | Neu5Acα2-3Galβ1-4[6OSO3]GlcNAcβ-Sp8 | 4 | 5 | 111 |
| 288 | Galβ1-4(Fucα1-3)[6OSO3]GlcNAc-Sp0 | 4 | 3 | 76 |
| 43 | [6OSO3]Galβ1-4GlcNAcβ-Sp8 | 4 | 6 | 149 |
| 391 | Neu5Acα2-3(GalNAcβ1-4)Galβ1-4GlcNAcβ1-3GalNAcα-Sp14 | 4 | 11 | 246 |
| 207 | Manα1-2Manα1-3Manα-Sp9 | 4 | 8 | 174 |
| 80 | Fucα1-4GlcNAcβ-Sp8 | 4 | 7 | 172 |
| 114 | Galα1-3Galβ1-3GlcNAcβ-Sp0 | 4 | 4 | 102 |
| 26 | [3OSO3]Galβ1-4[6OSO3]Glcβ-Sp8 | 4 | 1 | 27 |
| 130 | Galβ1-4GlcNAcβ1-6GalNAcα-Sp8 | 4 | 2 | 37 |
| 306 | GlcNAcβ1-2Manα1-3(Neu5Acα2-6Galβ1-4GlcNAcβ1-2Manα1-6)Manβ1-4GlcNAcβ1-4GlcNAcβ-Sp12 | 4 | 4 | 99 |
| 131 | Galβ1-3(GlcNAcβ1-6)GalNAcα-Sp8 | 4 | 3 | 71 |
| 179 | GlcNAcβ1-3Galβ1-4GlcNAcβ-Sp0 | 4 | 4 | 88 |
| 63 | Fucα1-2Galβ1-3GalNAcβ1-4(Neu5Acα2-3)Galβ1-4Glcβ-Sp0 | 4 | 3 | 67 |
| 97 | GalNAcβ1-4(Fucα1-3)GlcNAcβ-Sp0 | 4 | 7 | 184 |
| 208 | Manα1-6(Manα1-2Manα1-3)Manα1-6(Manα1-2Manα1-3)Manβ1-4GlcNAcβ1-4GlcNAcβ-Sp12 | 4 | 2 | 49 |
| 244 | Neu5Acα2-3Galβ1-3GalNAcβ1-3Galα1-4Galβ1-4Glcβ-Sp0 | 4 | 4 | 101 |
| 151 | Galβ1-4(Fucα1-3)GlcNAcβ1-4(Fucα1-3)GlcNAcβ-Sp0 | 4 | 7 | 185 |
| 3 | Manα-Sp8 | 4 | 8 | 201 |
| 309 | GlcNAcβ1-4GlcNAcβ-Sp12 | 4 | 1 | 26 |
| 323 | Neu5Acα2-3Galβ1-4GlcNAcβ1-2Manα1-3(Neu5Acα2-3Galβ1-4GlcNAcβ1-2Manα1-6)Manβ1-4GlcNAcβ1- | 4 | 10 | 274 |

Figure 4a Cont...

| | | | | |
|---|---|---|---|---|
| 425 | 4GlcNAcβ-Sp12<br>Fucα1-2Galβ1-3GlcNAcβ1-3(Fucα1-2Galβ1-3GlcNAcβ1-2Manα1-3(Fucα1-2Galβ1-3GlcNAcβ1-2Manα1-6)Manβ1-4GlcNAcβ1-4(Fucα1-6)GlcNAcβ-Sp22 | 4 | 4 | 2 | 92 |
| 236 | Neu5Acα2-3Galβ1-3[6OSO3]GlcNAc-Sp8 | 4 | 3 | 1 | 67 |
| 5 | GalNAcα-Sp15 | 4 | 5 | 2 | 128 |
| 393 | Galα1-3Galβ1-3GlcNAcβ1-2Manα1-3(Galα1-3Galβ1-3GlcNAcβ1-2Manα1-6)Manβ1-4GlcNAcβ1-4GlcNAc-Sp19 | 4 | 3 | 1 | 76 |
| 296 | 6-H2PO3Glcβ-Sp10 | 4 | 2 | 1 | 52 |
| 343 | Manα1-3(Neu5Acα2-6Galβ1-4GlcNAcβ1-2Manα1-6)Manβ1-4GlcNAc-Sp12 | 4 | 4 | 2 | 98 |
| 403 | Galα1-3Galβ1-4GlcNAcβ1-3GalNAcα-Sp14 | 4 | 5 | 3 | 142 |
| 340 | GlcNAcα1-4Galβ1-4GlcNAcβ1-3Galβ1-4(Fucα1-3)GlcNAcβ-Sp0 | 4 | 3 | 1 | 83 |
| 205 | Manα1-2Manα1-2Manα1-3Manα-Sp9 | 4 | 3 | 2 | 82 |
| 198 | G-ol-Sp8 | 4 | 5 | 2 | 134 |
| 53 | Galβ1-4GlcNAcβ1-2Manα1-3(Galβ1-4GlcNAcβ1-2Manα1-6)Manβ1-4GlcNAcβ1-4GlcNAcβ-Sp12 | 4 | 8 | 4 | 232 |
| 105 | Galα1-3(Fucα1-2)Galβ1-4GlcNAcβ-Sp0 | 4 | 3 | 1 | 73 |
| 235 | Neu5Acα2-3GalNAcβ1-4GlcNAcβ-Sp0 | 3 | 6 | 3 | 182 |
| 35 | [3OSO3]Galβ1-4GlcNAcβ-Sp8 | 3 | 8 | 4 | 225 |
| 117 | Galα1-3Galβ-Sp8 | 3 | 6 | 3 | 166 |
| 37 | [3OSO3]Galβ-Sp8 | 3 | 6 | 3 | 168 |
| 40 | 6-H2PO3Manα-Sp8 | 3 | 4 | 2 | 125 |
| 318 | Neu5Acα2-6Galβ1-4GlcNAcβ1-2Manα1-3(GlcNAcβ1-2Manα1-6)Manβ1-4GlcNAcβ1-4GlcNAcβ-Sp12 | 3 | 2 | 1 | 72 |
| 45 | Neu5Acα2-3[6OSO3]Galβ1-4GlcNAcβ-Sp8 | 3 | 4 | 2 | 109 |
| 256 | Neu5Acα2-3Galβ1-4GlcNAcβ1-3Galβ1-4GlcNAcβ-Sp0 | 3 | 4 | 2 | 120 |
| 410 | Galβ1-3GalNAcβ1-4(Neu5Acα2-8Neu5Acα2-3)Galβ1-4Glcβ-Sp0 | 3 | 4 | 2 | 127 |
| 77 | Fucα1-2Galβ1-4Glcβ-Sp0 | 3 | 3 | 1 | 84 |
| 188 | GlcNAcβ1-4GlcNAcβ1-4GlcNAcβ-Sp8 | 3 | 10 | 5 | 305 |
| 230 | Neu5Acα2-3(GalNAcβ1-4)Galβ1-4GlcNAcβ-Sp8 | 3 | 4 | 2 | 118 |
| 276 | Neu5Acβ2-6GalNAcα-Sp8 | 3 | 6 | 3 | 181 |

Figure 4a Cont...

| | | | | |
|---|---|---|---|---|
| 102 | Galα1-3(Fucα1-2)Galβ1-3GlcNAcβ-Sp8 | 3 | 6 | 3 | 184 |
| 150 | Galβ1-4(Fucα1-3)GlcNAcβ-Sp8 | 3 | 8 | 4 | 255 |
| 349 | Galβ1-4GlcNAcβ1-2Manα1-3(Manα1-6)Manβ1-4GlcNAcβ1-4GlcNAcβ-Sp12 | 3 | 7 | 3 | 205 |
| 246 | Fucα1-2[6OSO3]Galβ1-4Glc-Sp0 | 3 | 4 | 2 | 132 |
| 203 | KDNα2-3Galβ1-3GlcNAcβ-Sp0 | 3 | 3 | 1 | 93 |
| 69 | Fucα1-2Galβ1-4(Fucα1-3)GlcNAcβ1-3Galβ1-4(Fucα1-3)GlcNAcβ-Sp0 | 3 | 3 | 1 | 80 |
| 324 | Neu5Acα2-6Galβ1-4GlcNAcβ1-2Manα1-3(Neu5Acα2-3Galβ1-4GlcNAcβ1-2Manα1-6)Manβ1-4GlcNAcβ1-4GlcNAcβ-Sp12 | 3 | 4 | 2 | 136 |
| 431 | GlcNAcβ1-4(GlcNAcβ1-2)Manα1-3(GlcNAcβ1-4)(GlcNAcβ1-2Manα1-6)Manβ1-4GlcNAcβ1-4GlcNAc-Sp21 | 3 | 3 | 1 | 83 |
| 464 | Glcα1-6Glcα1-6Glcβ1-Sp10 | 3 | 5 | 2 | 147 |
| 311 | Manα1-6Manβ-Sp10 | 3 | 10 | 5 | 311 |
| 7 | Fucα-Sp9 | 3 | 4 | 2 | 114 |
| 49 | Manα1-3(Manα1-6)Manβ1-4GlcNAcβ1-4GlcNAcβ-Sp12 | 3 | 5 | 2 | 156 |
| 118 | Galα1-4(Fucα1-2)Galβ1-4GlcNAcβ-Sp8 | 3 | 3 | 1 | 91 |
| 247 | Neu5Acα2-3Galβ1-3GlcNAcβ-Sp0 | 3 | 1 | 1 | 40 |
| 365 | Neu5Acα2-6GlcNAcβ1-4GlcNAc-Sp21 | 3 | 4 | 2 | 135 |
| 342 | GlcNAcα1-4Galβ1-3GalNAc-Sp14 | 3 | 2 | 1 | 77 |
| 330 | Neu5Acα2-6Galβ1-4GlcNAcβ1-3Galβ1-4GlcNAcβ-Sp0 | 3 | 6 | 3 | 196 |
| 56 | Neu5Acα2-6Galβ1-4GlcNAcβ1-2Manα1-3(Neu5Acα2-6Galβ1-4GlcNAcβ1-2Manα1-6)Manβ1-4GlcNAcβ1-4GlcNAcβ-Sp12 | 3 | 5 | 3 | 172 |
| 359 | Fucα1-2Galβ1-3GlcNAcβ1-3Galβ1-4(Fucα1-3)GlcNAcβ-Sp20 | 3 | 5 | 2 | 151 |
| 113 | Galα1-3Galβ1-4(Fucα1-3)GlcNAcβ-Sp8 | 3 | 7 | 3 | 221 |
| 448 | Galβ1-4GlcNAcβ1-6GalNAc-Sp14 | 3 | 2 | 1 | 65 |
| 32 | [3OSO3]Galβ1-4(Fucα1-3)GlcNAcβ-Sp8 | 3 | 4 | 2 | 121 |
| 360 | Fucα1-2Galβ1-4GlcNAcβ1-2Manα1-3(Fucα1-2Galβ1-4GlcNAcβ1-2Manα1-6)Manβ1-4GlcNAcβ1-4GlcNAcβ-Sp20 | 3 | 5 | 2 | 167 |
| 266 | Neu5Acα2-6Galβ1-4GlcNAcβ-Sp0 | 3 | 1 | 1 | 47 |
| 239 | Neu5Acα2-3Galβ1-3(Neu5Acα2-3Galβ1-4)GlcNAcβ-Sp8 | 3 | 4 | 2 | 153 |

Figure 4a Cont...

| | | | | | |
|---|---|---|---|---|---|
| 398 | Fucα1-2Galβ1-4GlcNAcβ1-3GalNAcα-Sp14 | 3 | 5 | 2 | 173 |
| 373 | Galα1-3(Fucα1-2)Galβ1-3GlcNAcβ1-2Manα1-3(Galα1-3(Fucα1-2)Galβ1-3GlcNAcβ1-2Manα1-6)Manβ1-4GlcNAcβ1-4GlcNAcβ-Sp20 | 3 | 8 | 4 | 281 |
| 48 | [9NAc]Neu5Acα2-6Galβ1-4GlcNAcβ-Sp8 | 3 | 7 | 3 | 239 |
| 303 | Galβ1-4GlcNAcβ1-6Galβ1-4GlcNAcβ-Sp0 | 3 | 6 | 3 | 211 |
| 72 | Fucα1-2Galβ1-4(Fucα1-3)GlcNAcβ-Sp8 | 3 | 6 | 3 | 211 |
| 454 | Neu5Acα2-8Neu5Acα2-3Galb1-3GalNAcb1-4(Neu5Acα2-8Neu5Acα2-3)Galb1-4Glcb-sp0 | 3 | 2 | 1 | 67 |
| 212 | Manα1-3(Manα1-2Manα1-2Manα1-6)Manα-Sp9 | 3 | 5 | 2 | 168 |
| 106 | Galα1-3(Fucα1-2)Galβ1-4Glcβ-Sp0 | 3 | 6 | 3 | 225 |
| 214 | Manα1-6(Manα1-3)Manα1-6(Manα1-3)Manβ1-4GlcNAcβ1-4GlcNAcβ-Sp12 | 3 | 4 | 2 | 141 |
| 204 | KDNα2-3Galβ1-4GlcNAcβ-Sp0 | 3 | 6 | 3 | 223 |
| 382 | Galβ1-3GlcNAcβ1-3(Galβ1-4(Fucα1-3)GlcNAcβ1-6)Galβ1-4Glc-Sp21 | 3 | 6 | 3 | 228 |
| 135 | Galβ1-3(Neu5Acβ2-6)GalNAcα-Sp8 | 3 | 2 | 1 | 90 |
| 375 | Neu5Acα2-3Galβ1-4GlcNAcβ1-3GalNAcα-Sp14 | 3 | 4 | 2 | 173 |
| 261 | Neu5Acα2-3Galβ1-4Glcβ-Sp0 | 3 | 5 | 3 | 198 |
| 34 | [3OSO3]Galβ1-4[6OSO3]GlcNAcβ-Sp8 | 3 | 7 | 3 | 260 |
| 427 | Galβ1-3GlcNAcβ1-2Manα1-3(Galβ1-3GlcNAcβ1-2(Galβ1-3GlcNAcβ1-6)Manα1-6)Manβ1-4GlcNAcβ1-4GlcNAcβ-Sp19 | 3 | 4 | 2 | 170 |
| 94 | GalNAcβ1-3GalNAcα-Sp8 | 2 | 7 | 3 | 279 |
| 23 | [3OSO3]Galβ1-4(Fucα1-3)[6OSO3]Glc-Sp0 | 2 | 4 | 2 | 153 |
| 124 | Galβ1-2Galβ-Sp8 | 2 | 7 | 3 | 283 |
| 269 | Neu5Acα2-6Galβ1-4GlcNAcβ1-3Galβ1-4GlcNAcβ-Sp8 | 2 | 4 | 2 | 162 |
| 175 | GlcNAcβ1-3(GlcNAcβ1-6)Galβ1-4GlcNAcβ-Sp8 | 2 | 8 | 4 | 319 |
| 89 | GalNAcα1-3(Fucα1-2)Galβ-Sp8 | 2 | 4 | 2 | 185 |
| 413 | GalNAcα1-3(Fucα1-2)Galβ1-4GlcNAcβ1-3GalNAcα-Sp14 | 2 | 2 | 1 | 65 |
| 262 | Neu5Acα2-3Galβ1-4Glcβ-Sp8 | 2 | 5 | 3 | 227 |
| 400 | GalNAcα1-3GalNAcβ1-3Galα1-4Galβ1-4GlcNAcβ-Sp0 | 2 | 4 | 2 | 152 |
| 42 | [6OSO3]Galβ1-4Glcβ-Sp8 | 2 | 4 | 2 | 169 |

Figure 4a Cont...

| | | | | |
|---|---|---|---|---|
| 228 | Neu5Acα2-3(6-O-Su)Galβ1-4(Fucα1-3)GlcNAcβ-Sp8 | 2 | 4 | 2 | 197 |
| 209 | Manα1-2Manα1-6(Manα1-3)Manβ1-6(Manα1-2Manα1-3)Manβ1-4GlcNAcβ1-4GlcNAcβ-Sp12 | 2 | 3 | 1 | 132 |
| 298 | Galβ1-3Galβ1-4GlcNAcβ-Sp8 | 2 | 2 | 1 | 105 |
| 2 | Glcα-Sp8 | 2 | 2 | 1 | 109 |
| 168 | Galβ1-4GlcNAcβ-Sp8 | 2 | 6 | 3 | 265 |
| 153 | Galβ1-4[6OSO3]Glcβ-Sp0 | 2 | 1 | 0 | 34 |
| 154 | Galβ1-4[6OSO3]Glcβ-Sp8 | 2 | 4 | 2 | 198 |
| 186 | GlcNAcβ1-4GlcNAcβ1-4GlcNAcβ1-4GlcNAcβ1-4GlcNAcβ1-4β-Sp8 | 2 | 3 | 1 | 129 |
| 452 | Galα1-3Fucα1-2Galβ1-4GlcNAcβ1-3(Galα1-3Fucα1-2Galβ1-4GlcNAcβ1-6)GalNAc-Sp14 | 2 | 6 | 3 | 296 |
| 211 | Manα1-3(Manα1-6)Manα-Sp9 | 2 | 4 | 2 | 190 |
| 442 | GalNAcβ1-6GalNAcβ-Sp8 | 2 | 3 | 2 | 157 |
| 221 | Neu5Acα2-3Galβ1-3GalNAcα-Sp8 | 2 | 3 | 2 | 160 |
| 50 | Manα1-3(Manα1-6)Manβ1-4GlcNAcβ1-4GlcNAcβ-Sp13 | 2 | 3 | 1 | 141 |
| 402 | Galα1-4Galβ1-4GlcNAcβ1-2Manα1-3(Galα1-4Galβ1-4GlcNAcβ1-2Manα1-6)Manβ1-4GlcNAcβ1-4GlcNAcβ-LVANKT | | 4 | 2 | 202 |
| 322 | Galβ1-3GlcNAcβ1-2Manα1-3(Galβ1-3GlcNAcβ1-2Manα1-6)Manβ1-4GlcNAcβ1-4GlcNAcβ-Sp19 | 2 | 3 | 2 | 173 |
| 465 | Glcα1-4Glcα1-4Glcα1-4Glcβ-Sp10 | 2 | 3 | 1 | 139 |
| 104 | Galα1-3(Fucα1-2)Galβ1-4(Fucα1-3)GlcNAcβ-Sp8 | 2 | 6 | 3 | 323 |
| 70 | Fucα1-2Galβ1-4(Fucα1-3)GlcNAcβ1-3Galβ1-4(Fucα1-3)GlcNAcβ-Sp0 | 2 | 4 | 2 | 227 |
| 320 | Neu5Acα2-8Neu5Acα2-8Neu5Acβ-Sp8 | 2 | 4 | 2 | 236 |
| 46 | [6OSO3]GlcNAcβ-Sp8 | 2 | 2 | 1 | 111 |
| 457 | Galα1-3(Fucα1-2)Galβ1-3GlcNAcβ1-2Manα1-6(Galα1-3(Fucα1-2)Galβ1-3GlcNAcβ1-2Manα1-3)Manβ1-4GlcNAcβ1-4(Fucα1-6)GlcNAcβ-Sp22 | 2 | 2 | 1 | 88 |
| 127 | Galβ1-3(Fucα1-4)GlcNAcβ-Sp0 | 2 | 5 | 3 | 279 |
| 233 | Neu5Acα2-3(Neu5Acα2-6)GalNAcα-Sp8 | 2 | 1 | 1 | 67 |
| 161 | Galβ1-4GlcNAcβ1-3Galβ1-4GlcNAcβ-Sp0 | 2 | 4 | 2 | 245 |
| 17 | GlcNAcβ-Sp8 | 2 | 3 | 1 | 146 |
| 120 | Galα1-4Galβ1-4GlcNAcβ-Sp8 | 2 | 6 | 3 | 311 |

Figure 4a Cont...

| | | | | | |
|---|---|---|---|---|---|
| 144 | Galβ1-3Galβ-Sp8 | 2 | 2 | 1 | 113 |
| 142 | Galβ1-3GalNAcβ1-4(Neu5Acα2-3)Galβ1-4Glcβ-Sp0 | 2 | 5 | 3 | 307 |
| 220 | Fucα1-2[6OSO3]Galβ1-4[6OSO3]Glc-Sp0 | 2 | 2 | 1 | 93 |
| 62 | Fucα1-2Galβ1-3GalNAcα-Sp14 | 2 | 3 | 1 | 178 |
| 440 | Galβ1-6Galβ-Sp10 | 2 | 2 | 1 | 107 |
| 78 | Fucα1-2Galβ-Sp8 | 2 | 3 | 2 | 216 |
| 460 | Galβ1-4GlcNAcβ1-6(Galβ1-4GlcNAcβ1-2)Manα1-6(Galβ1-4GlcNAcβ1-2Manα1-3)Manβ1-4GlcNAcβ1-4GlcNAcβ-Sp19 | 2 | 4 | 2 | 229 |
| 145 | Galβ1-3GlcNAcβ1-3Galβ1-4GlcNAcβ-Sp0 | 2 | 3 | 2 | 193 |
| 426 | Galα1-3(Fucα1-2)Galβ1-4GlcNAcβ1-2Manα1-3(Galα1-3(Fucα1-2)Galβ1-4GlcNAcβ1-2Manα1-6)Manβ1-4GlcNAcβ1-4(Fucα1-6)GlcNAcβ-Sp22 | 2 | 3 | 2 | 211 |
| 11 | Neu5Acβ-Sp8 | 2 | 6 | 3 | 369 |
| 216 | Neu5Acα2-3Galβ1-4GlcNAcβ1-3Galβ1-4(Fucα1-3)GlcNAc-Sp0 | 2 | 2 | 1 | 159 |
| 163 | Galβ1-4GlcNAcβ1-3Galβ1-4Glcβ-Sp8 | 1 | 2 | 1 | 141 |
| 28 | [3OSO3]Galβ1-3GalNAcα-Sp8 | 1 | 3 | 2 | 236 |
| 24 | [3OSO3]Galβ1-4Glcβ-Sp8 | 1 | 1 | 1 | 104 |
| 206 | Manα1-2Manα1-3(Manα1-2Manα1-6)Manα-Sp9 | 1 | 4 | 2 | 314 |
| 218 | Fucα1-2[6OSO3]Galβ1-4GlcNAc-Sp0 | 1 | 2 | 1 | 128 |
| 196 | Glcβ1-4Glcβ-Sp8 | 1 | 1 | 0 | 65 |
| 36 | [3OSO3]Galβ1-4GlcNAcβ-Sp8 | 1 | 2 | 1 | 174 |
| 110 | Galα1-3GalNAcα-Sp8 | 1 | 4 | 2 | 278 |
| 141 | Galβ1-3GalNAcβ1-3Galα1-4Galβ1-4Glcβ-Sp0 | 1 | 3 | 1 | 195 |
| 265 | Neu5Acα2-6Galβ1-4[6OSO3]GlcNAcβ-Sp8 | 1 | 6 | 3 | 473 |
| 396 | GlcNAcβ1-2Manα1-3(Galβ1-4GlcNAcβ1-2Manα1-6)Manβ1-4GlcNAc-Sp12 | 1 | 2 | 1 | 140 |
| 1 | Galα-Sp8 | 1 | 1 | 1 | 86 |
| 368 | Galβ1-4GlcNAcβ1-2(Galβ1-4GlcNAcβ1-4)Manα1-3(Galβ1-4GlcNAcβ1-2Manα1-6)Manβ1-4GlcNAc-Sp21 | 1 | 2 | 1 | 185 |
| 354 | [6OSO3]GlcNAcβ1-3Galβ1-4GlcNAc-β-Sp0 | 1 | 2 | 1 | 163 |
| 162 | Galβ1-4GlcNAcβ1-3Galβ1-4Glcβ-Sp0 | 1 | 2 | 1 | 190 |

Figure 4a Cont...

| | | | | | |
|---|---|---|---|---|---|
| 170 | Galβ1-4Glcβ-Sp8 | | | | 277 |
| 52 | GlcNAcβ1-2Manα1-3(GlcNAcβ1-2Manα1-6)Manβ1-4GlcNAcβ1-4GlcNAcβ-Sp13 | 1 | 3 | 2 | 513 |
| 223 | Neu5Acα2-8Neu5Acα2-8Neu5Acα2-3(GalNAcβ1-4)Galβ1-4Glcβ-Sp0 | 1 | 6 | 3 | 325 |
| 194 | Glcα1-4Glcα-Sp8 | 1 | 4 | 2 | 385 |
| 181 | GlcNAcβ1-3Galβ1-4GlcNAcβ1-3Galβ1-4Glcβ-Sp0 | 1 | 4 | 2 | 305 |
| 438 | Galα1-3Galβ1-4Glc-Sp10 | 1 | 4 | 2 | 121 |
| 95 | GalNAcβ1-3(Fucα1-2)Galβ-Sp8 | 1 | 1 | 1 | 185 |
| 123 | Galα1-6Glcβ-Sp8 | 1 | 2 | 4 | 711 |
| 345 | Neu5Acα2-6Galβ1-4GlcNAcβ1-2Manα1-6Manβ1-4GlcNAcβ1-4GlcNAc-Sp12 | 1 | 8 | 1 | 230 |
| 414 | GalNAcα1-3GalNAcβ1-3Galα1-4Galβ1-4Glcβ-Sp0 | 1 | 2 | 1 | 227 |
| 395 | Galβ1-4GlcNAcβ1-2Manα1-3(GlcNAcβ1-2Manα1-6)Manβ1-4GlcNAcβ1-4GlcNAc-Sp12 | 1 | 2 | 3 | 570 |
| 58 | Fucα1-2Galβ1-3GalNAcβ1-3Galα-Sp9 | 1 | 6 | 2 | 474 |
| 172 | GlcNAcα1-6Galβ1-4GlcNAcβ1-4GlcNAcβ-Sp8 | 1 | 5 | 1 | 108 |
| 416 | Galα1-3(Fucα1-2)Galβ1-4(Fucα1-3)GlcNAcβ1-3)GalNAc-Sp14 | 1 | 1 | 1 | 280 |
| 294 | [3OSO3][4OSO3]Galβ1-4GlcNAcβ-Sp0 | 1 | 3 | 1 | 201 |
| 148 | Galβ1-3GlcNAcβ-Sp8 | 1 | 2 | 1 | 645 |
| 284 | Neu5Gcα2-6Galβ1-4GlcNAcβ-Sp8 | 1 | 6 | 3 | 185 |
| 364 | Galβ1-3(Fucα1-4)GlcNAcβ1-2Manα1-3(Galβ1-3(Fucα1-4)GlcNAcβ1-2Manα1-6)Manβ1-4GlcNAcβ1-4(Fucα1-6)GlcNAcβ-Sp22 | | 2 | 1 | 395 |
| 407 | GlcNAcβ1-6(GlcNAcβ1-3)GalNAcα-Sp14 | 1 | 4 | 2 | 754 |
| 267 | Neu5Acα2-6Galβ1-4GlcNAcβ-Sp8 | 1 | 7 | 3 | 453 |
| 424 | Galα1-3GalNAcβ1-3GlcNAcβ1-3GalNAc-Sp14 | 1 | 4 | 2 | 583 |
| 279 | Neu5Gcα2-3Galβ1-3GlcNAcβ-Sp0 | 1 | 5 | 2 | 344 |
| 271 | Neu5Acα2-6Galβ1-4Glcβ-Sp8 | 1 | 3 | 1 | 814 |
| 75 | Fucα1-2Galβ1-4GlcNAcβ-Sp0 | 1 | 7 | 3 | 337 |
| 333 | GalNAcα1-3(Fucα1-2)Galβ1-4GlcNAcβ1-3Galβ1-4GlcNAcβ-Sp0 | 1 | 3 | 1 | 372 |
| 292 | Neu5Acα2-3Galβ1-3GlcNAcβ1-3Galβ1-3GlcNAcβ-Sp0 | 1 | 1 | 1 | 152 |
| 326 | Neu5Ac(9Ac)α2-3Galβ1-4GlcNAcβ-Sp0 | 1 | 4 | 2 | 556 |

Figure 4a Cont...

| | | | 10 | 5 | |
|---|---|---|---|---|---|
| 111 | Galα1-3GalNAcα-Sp16 | 1 | 5 | 2 | 1654 |
| 441 | Neu5Acα2-3Galβ1-4GlcNAcβ1-3Galβ-Sp8 | 1 | 5 | 2 | 799 |
| 433 | GlcNAcβ1-4(GlcNAcβ1-2)Manα1-3(GlcNAcβ1-4)(GlcNAcβ1-6(GlcNAcβ1-2)Manα1-6)Manβ1-4GlcNAcβ1-4GlcNAc-Sp21 | 1 | 2 | 1 | 428 |
| 71 | Fucα1-2Galβ1-4(Fucα1-3)GlcNAcβ-Sp0 | 1 | 2 | 1 | 370 |
| 33 | [3OSO3]Galβ1-4[6OSO3]GlcNAcβ-Sp0 | 1 | 8 | 4 | 1366 |
| 79 | Fucα1-3GlcNAcβ-Sp8 | 0 | 5 | 2 | 909 |
| 122 | Galα1-4GlcNAcβ-Sp8 | 0 | 5 | 3 | 1065 |
| 171 | GlcNAcα1-3Galβ1-4GlcNAcβ-Sp8 | 0 | 4 | 2 | 782 |
| 200 | GlcAβ-Sp8 | 0 | 5 | 3 | 1121 |
| 461 | Galβ1-4GlcNAcβ-(OCH2CH2)6NH2 | 0 | 3 | 1 | 667 |
| 399 | Galβ1-4(Fucα1-3)GlcNAcβ1-3GalNAcα-Sp14 | 0 | 5 | 3 | 1204 |
| 202 | GlcAβ1-6Galβ-Sp8 | 0 | 3 | 1 | 744 |
| 44 | [6OSO3]Galβ1-4[6OSO3]Glcβ-Sp8 | 0 | 2 | 1 | 480 |
| 325 | Fucα1-3(Galβ1-4)GlcNAcβ1-2Manα1-3(Fucα1-3(Galβ1-4)GlcNAcβ1-2Manα1-6)Manβ1-4GlcNAcβ-Sp20 | 0 | 5 | 3 | 1717 |
| 243 | Neu5Acα2-3Galβ-Sp8 | 0 | 2 | 1 | 739 |
| 295 | [6OSO3]Galβ1-4[6OSO3]GlcNAcβ-Sp0 | 0 | 4 | 2 | 1675 |
| 119 | Galα1-4Galβ1-4GlcNAcβ-Sp0 | 0 | 1 | 0 | 399 |
| 385 | Galβ1-3GlcNAcβ1-3(Galβ1-3GlcNAcβ1-4(Fucα1-3)GlcNAcβ1-6)Galβ1-4Glc-Sp21 | 0 | 8 | 4 | 3806 |
| 12 | Galβ-Sp8 | 0 | 4 | 2 | 1840 |
| 225 | Neu5Acα2-8Neu5Acα2-3Galβ1-4Glcβ-Sp0 | 0 | 2 | 1 | 997 |
| 447 | Galβ1-4GlcNAcβ1-3(Galβ1-4GlcNAcβ1-6)GalNAcα-Sp14 | 0 | 9 | 5 | 4305 |
| 351 | Galβ1-4GlcNAcβ1-2Manα1-3(Galβ1-4GlcNAcβ1-2Manα1-6)Manβ1-4GlcNAcβ1-4(Fucα1-6)GlcNAcβ-Sp22 | 0 | 2 | 1 | 1164 |
| 315 | Neu5Acα2-3Galβ1-3(Neu5Acα2-3Galβ1-4GlcNAcβ1-6)GalNAcα-Sp14 | 0 | 5 | 2 | 2496 |
| 81 | Fucβ1-3GlcNAcβ-Sp8 | 0 | 2 | 1 | 2130 |
| 192 | GlcNAcβ1-6Galβ1-4GlcNAcβ-Sp8 | 0 | 1 | 1 | 1088 |
| 317 | Neu5Acα2-6Galβ1-4GlcNAcβ1-2Manα1-3(Galβ1-4GlcNAcβ1-2Manα1-6)Manβ1-4GlcNAcβ1-4GlcNAcβ-Sp12 | 0 | 3 | 1 | -8349 |

Figure 4a Cont...

| | | | | |
|---|---|---|---|---|
| 355 | KDNα2-3Galβ1-4(Fucα1-3)GlcNAc-Sp0 | 0 | 4 | 2 | -10277 |
| 376 | Neu5Acα2-6Galβ1-4GlcNAcβ1-3GalNAc-Sp14 | 0 | 5 | 2 | -8083 |
| 300 | Galβ1-4GlcNAcβ1-3(Galβ1-4GlcNAcβ1-6)Galβ1-4GlcNAc-Sp0 | 0 | 6 | 3 | -9369 |
| 307 | GlcNAcβ1-3Man-Sp10 | 0 | 1 | 1 | -1653 |
| 301 | Galβ1-4GlcNAcβ1-3(GlcNAcβ1-6)Galβ1-4GlcNAc-Sp0 | 0 | 2 | 1 | -2459 |
| 439 | Galβ1-4Galβ-Sp10 | 0 | 4 | 2 | -2717 |
| 316 | Neu5Acα2-3Galβ1-4GlcNAcβ1-2Manα1-3(Neu5Acα2-6Galβ1-4GlcNAcβ1-2Manα1-6)Manβ1-4GlcNAcβ1-4GlcNAcβ-Sp12 | 0 | 4 | 2 | -3188 |
| 126 | Galβ1-3(Fucα1-4)GlcNAcβ1-3Galβ1-4GlcNAcβ-Sp0 | 0 | 2 | 1 | -1422 |
| 159 | Galβ1-4GlcNAcβ1-3Galβ1-4(Fucα1-3)GlcNAcβ1-3Galβ1-4(Fucα1-3)GlcNAcβ-Sp0 | 0 | 3 | 2 | -1277 |
| 101 | Galα1-3(Fucα1-2)Galβ1-3GlcNAcβ-Sp0 | 0 | 7 | 3 | -2492 |
| 140 | Galβ1-3GalNAcβ-Sp8 | 0 | 4 | 2 | -1225 |
| 462 | Galα1-3(Fucα1-2)Galβ1-3GalNAcα-Sp8 | 0 | 4 | 2 | -1343 |
| 227 | Neu5Acα2-8Neu5Acα2-8Neu5Acα-Sp8 | 0 | 4 | 2 | -1247 |
| 190 | GlcNAcβ1-6GalNAcα-Sp8 | 0 | 2 | 1 | -594 |
| 275 | Galβ1-3(Fucα1-4)GlcNAcβ1-3Galβ1-3(Fucα1-4)GlcNAcβ-Sp0 | 0 | 2 | 1 | -483 |
| 277 | Neu5Acβ2-6Galβ1-4GlcNAcβ-Sp8 | 0 | 2 | 1 | -430 |
| 137 | Galβ1-3GalNAcα-Sp8 | 0 | 11 | 5 | -2173 |
| 331 | Galα1-4Galβ1-4GlcNAcβ1-3Galβ1-4Glcβ-Sp0 | -1 | 6 | 3 | -1243 |
| 380 | Galβ1-3GalNAcα1-3(Fucα1-2)Galβ1-4GlcNAc-Sp0 | -1 | 1 | 0 | -186 |
| 329 | Neu5Acα2-3Galβ1-3(Fucα1-4)GlcNAcβ1-3Galβ1-4Glcβ-Sp0 | -1 | 7 | 3 | -1171 |
| 143 | Galβ1-3GalNAcα1-4Galβ1-4GlcNAcβ-Sp8 | -1 | 4 | 2 | -626 |
| 185 | GlcNAcβ1-4Galβ1-4GlcNAcβ-Sp8 | -1 | 2 | 1 | -381 |
| 167 | Galβ1-4GlcNAcβ-Sp0 | -1 | 3 | 1 | -444 |
| 274 | Neu5Acα2-8Neu5Acα2-3Galβ1-4Glcβ-Sp0 | -1 | 6 | 3 | -888 |
| 251 | Neu5Acα2-3Galβ1-4(Fucα1-3)GlcNAcβ1-3Galβ1-4(Fucα1-3)GlcNAcβ-Sp0 | -1 | 3 | 1 | -326 |
| 109 | Galα1-3(Galα1-4)Galβ1-4GlcNAcβ-Sp8 | -1 | 6 | 3 | -641 |
| 260 | Fucα1-2Galβ1-4[6OSO3]Glc-Sp0 | -1 | 1 | 0 | -113 |

Figure 4a Cont...

| | | | | |
|---|---|---|---|---|
| 173 | GlcNAcβ1-2Galβ1-3GalNAcα-Sp8 | | 2 | 1 | -204 |
| 6 | Fucα-Sp8 | -1 | 6 | 3 | -621 |
| 263 | Neu5Acα2-6GalNAcα-Sp8 | -1 | 6 | 3 | -620 |
| 99 | GalNAcβ1-4GlcNAcβ-Sp8 | -1 | 1 | 1 | -115 |
| 41 | [6OSO3]Galβ1-4Glcβ-Sp0 | -1 | 3 | 1 | -262 |
| 370 | Galα1-3(Fucα1-2)Galβ1-4GlcNAcβ1-2Manα1-3(Galα1-3(Fucα1-2)Galβ1-4GlcNAcβ1-2Manα1-6)Manβ1-4GlcNAcβ1-4GlcNAcβ-Sp20 | -1 | 4 | 2 | -345 |
| 90 | GalNAcα1-3(Fucα1-2)Galβ-Sp18 | -1 | 5 | 3 | -496 |
| 264 | Neu5Acα2-6GalNAcβ1-4GlcNAcβ-Sp0 | -1 | 4 | 2 | -349 |
| 19 | Galβ1-4GlcNAcβ1-3(Galβ1-4GlcNAcβ1-6)GalNAcα-Sp8 | -1 | 4 | 2 | -356 |
| 383 | Fucα1-2Galβ1-3(Fucα1-4)GlcNAcβ1-3(Galβ1-4GlcNAcβ1-6)Galβ1-4Glc-Sp21 | -1 | 5 | 2 | -399 |
| 257 | Neu5Acα2-3Galβ1-4GlcNAcβ-Sp0 | -1 | 4 | 2 | -328 |
| 215 | Manβ1-4GlcNAcβ-Sp0 | -1 | 2 | 1 | -147 |
| 293 | Neu5Acα2-3Galβ1-4GlcNAcβ1-3GlcNAcβ-Sp8 | -1 | 3 | 1 | -208 |
| 184 | GlcNAcβ1-4(GlcNAcβ1-6)GalNAcα-Sp8 | -1 | 1 | 0 | -66 |
| 248 | Neu5Acα2-3Galβ1-3GlcNAcβ-Sp8 | -1 | 3 | 2 | -212 |
| 273 | Neu5Acα2-8Neu5Acα-Sp8 | -1 | 3 | 2 | -209 |
| 152 | Galβ1-4(Fucα1-3)GlcNAcβ1-4Galβ1-4(Fucα1-3)GlcNAcβ-Sp0 | -2 | 4 | 2 | -280 |
| 272 | Neu5Acα2-6Galβ-Sp8 | -2 | 3 | 2 | -215 |
| 328 | Neu5Acα2-6Galβ1-4GlcNAcβ1-3Galβ1-4GlcNAcβ-Sp0 | -2 | 3 | 1 | -168 |
| 253 | Neu5Acα2-3Galβ1-4(Fucα1-3)GlcNAcβ-Sp8 | -2 | 4 | 2 | -201 |
| 210 | Manα1-2Manα1-2Manα1-3(Manα1-2Manα1-6)Manα1-6)Manβ1-4GlcNAcβ1-4GlcNAcβ-Sp12 | -2 | 5 | 2 | -263 |
| 259 | Neu5Acα2-3Galβ1-4GlcNAcβ1-3Galβ1-4GlcNAcβ-Sp0 | -2 | 1 | 1 | -76 |
| 15 | GalNAcβ-Sp8 | -2 | 6 | 3 | -336 |
| 304 | GalNAcβ1-3Galβ-Sp8 | -2 | 3 | 1 | -140 |
| 169 | Galβ1-4Glcβ-Sp0 | -2 | 2 | 1 | -104 |
| 87 | GalNAcα1-3(Fucα1-2)Galβ1-4Glcβ-Sp0 | -2 | 2 | 1 | -117 |

Figure 4a Cont...

| | | | | |
|---|---|---|---|---|
| 352 | Galβ1-3GlcNAcβ1-2Manα1-3(Galβ1-3GlcNAcβ1-2Manα1-6)Manβ1-4GlcNAcβ1-4(Fucα1-6)GlcNAcβ-Sp22 | -2 | 5 | 3 | -239 |
| 350 | GlcNAcβ1-2Manα1-3(GlcNAcβ1-2Manα1-6)Manβ1-4GlcNAcβ1-4(Fucα1-6)GlcNAcβ-Sp22 | -2 | 2 | 1 | -96 |
| 98 | GalNAcβ1-4GlcNAcβ-Sp0 | -2 | 2 | 1 | -91 |
| 147 | Galβ1-3GlcNAcβ-Sp0 | -2 | 0 | 0 | -21 |
| 224 | Neu5Acα2-8Neu5Acα2-3(GalNAcβ1-4)Galβ1-4Glcβ-Sp0 | -2 | 3 | 1 | -115 |
| 347 | Galβ1-4GlcNAcβ1-2Manα1-3Manβ1-4GlcNAcβ1-4GlcNAc-Sp12 | -3 | 5 | 3 | -198 |
| 13 | Glcβ-Sp8 | -3 | 3 | 1 | -96 |
| 61 | Fucα1-2Galβ1-3GalNAcα-Sp8 | -3 | 2 | 1 | -83 |
| 187 | GlcNAcβ1-4GlcNAcβ1-4GlcNAcβ1-4GlcNAcβ-Sp8 | -3 | 4 | 2 | -128 |
| 29 | [3OSO3]Galβ1-3GlcNAcβ-Sp0 | -3 | 4 | 2 | -142 |
| 189 | GlcNAcβ1-6(Galβ1-3)GalNAcα-Sp8 | -3 | 7 | 4 | -221 |
| 450 | Galβ1-4GlcNAcβ1-2Manα-Sp0 | -3 | 6 | 3 | -169 |
| 308 | GlcNAcβ1-4GlcNAcα-Sp10 | -3 | 2 | 1 | -53 |
| 177 | GlcNAcβ1-3GalNAcα-Sp14 | -4 | 1 | 0 | -14 |
| 356 | KDNα2-6Galβ1-4GlcNAcβ-Sp0 | -4 | 4 | 2 | -107 |
| 85 | GalNAcα1-3(Fucα1-2)Galβ1-4GlcNAcβ-Sp0 | -4 | 7 | 3 | -176 |
| 392 | GalNAcα1-3(Fucα1-2)Galβ1-3GalNAcα1-3(Fucα1-2)Galβ1-4GlcNAcβ-Sp0 | -4 | 0 | 0 | -7 |
| 22 | [3OSO3][6OSO3]Galβ1-4GlcNAcβ-Sp0 | -5 | 6 | 3 | -135 |
| 59 | Fucα1-2Galβ1-3GalNAcβ1-3Galα1-4Galβ1-4Glcβ-Sp9 | -5 | 4 | 2 | -81 |
| 18 | GlcN(Gc)β-Sp8 | -5 | 2 | 1 | -36 |
| 435 | Galβ1-4GlcNAcβ1-4(Galβ1-4GlcNAcβ1-2Manα1-3(GlcNAcβ1-4)(Galβ1-4GlcNAcβ1-2Manα1-6)Manβ1-4GlcNAcβ1-4GlcNAc-Sp21 | -5 | 9 | 4 | -175 |
| 125 | Galβ1-3(Fucα1-4)GlcNAcβ1-3Galβ1-4(Fucα1-3)GlcNAcβ-Sp0 | -5 | 2 | 1 | -37 |
| 250 | Neu5Acα2-3Galβ1-4(Fucα1-3)[6OSO3]GlcNAcβ-Sp8 | -6 | 2 | 1 | -43 |
| 287 | Galβ1-3GlcNAcβ1-3Galβ1-3GlcNAcβ-Sp0 | -6 | 4 | 2 | -58 |
| 9 | Neu5Acα-Sp8 | -7 | 2 | 1 | -32 |

Figure 4a Cont...

| Glycan number on array | Glycan Structure | Average binding mAb84 | Average binding mAb85 | Relative binding |
|---|---|---|---|---|
| 65 | Fucα1-2Galβ1-3GlcNAcβ1-3Galβ1-4Glcβ-Sp8 | 28216 | 758 | 37.22 |
| 458 | Neu5Acα2-6Galβ1-4GlcNAcβ1-6(Fucα1-2Galβ1-3GlcNAcβ1-3)Galβ-4Glc-Sp21 | 27746 | 585 | 47.42 |
| 67 | Fucα1-2Galβ1-3GlcNAcβ-Sp0 | 26640 | 482 | 55.26 |
| 66 | Fucα1-2Galβ1-3GlcNAcβ1-3Galβ1-4Glcβ-Sp10 | 25696 | 446 | 57.61 |
| 421 | Fucα1-2Galβ1-3GlcNAcβ1-3GalNAc-Sp14 | 25670 | 193 | 133.00 |
| 428 | Fucα1-2Galβ1-3GlcNAcβ1-3(Galβ1-4GlcNAcβ1-6)Galβ1-4Glc-Sp21 | 24411 | 129 | 189.23 |
| 367 | Fucα1-2Galβ1-3GlcNAcβ1-3(Galβ1-4(Fucα1-3)GlcNAcβ1-6)Galβ1-4Glc-Sp21 | 22081 | 43 | 513.51 |
| 68 | Fucα1-2Galβ1-3GlcNAcβ-Sp8 | 21144 | 35 | 604.11 |
| 359 | Fucα1-2Galβ1-3GlcNAcβ1-2Manα1-3(Fucα1-2Galβ1-3GlcNAcβ1-2Manα1-6)Manβ1-4GlcNAcβ1-4GlcNAcβ-Sp20 | 18744 | 29 | 646.34 |

Figure 5

```
  1  MRCALALSAL  LLLLSTPPLL  PSSPSPSPSP  SPSQNATQTT  TDSSNKTAPT
 51  PASSVTIMAT  DTAQQSTVPT  SKANEILASV  KATLGVSSD   SPGTTTLAQQ
101  VSGPVNTTVA  RGGGSGNPTT  TIESPKSTKS  ADTTTVATST  ATAKPNTTSS
151  QNGAEDTTNS  GGKSSHSVTT  DLTSTKAEHL  TTPHPTSPLS  PRQPTLTHPV
201  ATPTSSGHDH  LMKISSSSST  VAIPGYTFTS  PGMTTTLPSS  VISQRTQQTS
251  SQMPASSTAP  SSQETVQPTS  PATALRTPTL  PETMSSSPTA  ASTTHRYPKT
301  PSPTVAHESN  WAKCEDLETQ  TQSEKQLVLN  LTGNTLCAGG  ASDEKLISLI
351  CRAVKATFNP  AQDKCGIRLA  SVPGSQTVVV  KEITIHTKLP  AKDVYERLKD
401  KWDELKEAGV  SDMKLGDQGP  PEEAEDRFSM  PLIITIVCMA  SFLLVAALY
451  GCCHQRLSQR  KDQQRLTEEL  QTVENGYHDN  PTLEVMETSS  EMQEKKVVSL
501  NGELGDSWIV  PLDNLTKDDL  DEEEDTHL
```

SEQ ID NO: 1

Figure 6

```
  1  MRCALALSAL LLLLSTPPLL PSSPSPSPSP SQNATQTTTD SSNKTAPTPA SSVTIMATDT
 61  AQQSTVPTSK ANEILASVKA TTLGVSSDSP GTTTLAQQVS GPVNTTVARG GGSGNPTTTI
121  ESPKSTKSAD TTTVATSTAT ADNTTSSQN GAEDTTNSGG KSSHSVTTDL TSTKAEHLTT
181  PHPTSPLSPR QPTSTHPVAT       SGHDHLM KISSSSSTVA IPGYTFTSPG MTTTLLETVF
241  HHVSQAGLEL LTSGDLPTLA       AGITASS VISQRTQQTS SQMPASSTAP SSQETVQPTS
301  PATALRTPTL PETMSSSPTA...... THRYPKT PSPTVAHESN WAKCEDLETQ TQSEKQLVLN
361  LTGNTLCAGG ASDEKLISLI CRAVKATFNP AQDKCGIRLA SVPGSQTVVV KEITIHTKLP
421  AKDVYERLKD KWDELKEAGV SDMKLGDQGP PEEAEDRFSM PLIITVCMA SFLLLVAALY
481  GCCHQRLSQR KDQQRLTEEL QTVENGYHDN PTLEVMETSS EMQEKKVVSL NGELGDSWIV
541  PLDNLTKDDL DEEEDTHL
     [O00592.2  GI:229462740; SEQ ID NO:2]
```

Figure 7

```
  1  MRCALALSAL LLLLSTPPLL PSSPSPSPSP SPSQNATQTT TDSSNKTAPT PASSVTIMAT
 61  DTAQQSTVPT SKANEILASV KATTLGVSSD SPGTTTLAQQ VSGPVNTTVA RGGSSGNPTT
121  TIESPKSTKS ADTTTVATST ATAKPNTTSS QNGAEDTTNS GGKSSHSVTT DLTSTKAEHL
181  TTPHPTSPLS PRQPTLTHPV ATPTSSGHDH LMKISSSSST VAIPGYTFTS PGMTTTLLET
241  VFHHVSQAGL ELLTSGDLPT LASQSAGITA SSVISQRTQQ TSSQMPASST APSSQETVQP
301  TSPATALRTP TLPETMSSSP TAASTTHRYP KTPSPTVAHE SNWAKCEDLE TQTQSEKQLV
361  LNLTGNTLCA GGASDEKLIS LICRAVKATF NPAQDKCGIR LASVPGSQTV VVKEITIHTK
421  LPAKDVYERL KDKWDELKEA GVSDMKLGDQ GPPEEAEDRF SMPLIITIVC MASFLLLVAA
481  LYGCCHQRLS QRKDQQRLTE ELQTVENGYH DNPTLEVMET SSEMQEKKVV SLNGELGDSW
541  IVPLDNLTKD DLDEEEDTHL
     [AAI43319.1  GI:219520307; SEQ ID NO: 3]
```

Figure 8 mAb 84 VL
The amino acids not underlined correspond to framework regions and
underlined corresponds to CDRs.

```
1     ACGCCAGCTATTTAGGTGACACTATAGAATACTCAAGCTATGCATCCAACGCGTTGGGAG

61    CTCTCCCATATGGTCGACCTGCAGGCGGCCGCACTAGTGATTGACATTGAGCTCACCCAG
1                                                  D  I  E  L  T  Q

121   TCTCCAGCAATCATGTCTGCATCTCCAGGGGAGAAGGTCACCATGACCTGCAGTGCCAGC
7      S  P  A  I  M  S  A  S  P  G  E  K  V  T  M  T  C  S  A  S

181   TCAAGTGTAAATTACATGTACTGGTACCAGCAGAAGCCAGGATCCTCCCCCAGACTCCTG
27     S  S  V  N  Y  M  Y  W  Y  Q  Q  K  P  G  S  S  P  R  L  L

241   ATTTATGACACATCCAACCTGGCTTCTGGAGTCCCTGTTCGCTTCAGTGGCAGTGGGTCT
47     I  Y  D  T  S  N  L  A  S  G  V  P  V  R  F  S  G  S  G  S

301   GGGACCTCTTACTCTCTCACAATCAGCCGAATGGAGGCTGAAGATGCTGCCACTTATTAC
67     G  T  S  Y  S  L  T  I  S  R  M  E  A  E  D  A  A  T  Y  Y

361   TGCCAGCAGTGGAGTAGTTACCCGTACACGTTCGGAGGGGGGACCAAGCTGGAAATAAAA
87     C  Q  Q  W  S  S  Y  P  Y  T  F  G  G  G  T  K  L  E  I  K

421   CGGAATCCCGCGGCCATGGCGGCCGGGAGCATGCGACGTCGGGCCCAATTCGCCCTATAG
107    R

481   TGAGTCGTATTACAATTCACTGGCCGTCGTTTTACAACGTCGTGACTGGGAAAACCCTGG
541   CGTTACCCAACTTAATCGCCTTGCAGCACATCCCCCTTTCGCCAGCTGGCGTAATAGCGA
601   AGAGGCGCGCACCGATCGCCCTTCTCAACAGTTGCGCAGCCTGAATAGCGAATAGACGCG
661   CCCTGTAGCGGCGCATTATGCGCGGCGGGGTGTGGTGGTTACGCGCAGCGTGACCGCTAC
721   ACTTGTCAGCGCCCTAGCGCCGCTCCTTTCGCTTTCTTCCCTTCCTTTCTCGCCACGTTC
781   GCCGGCTTGCTCGTCAGG
```

Based on V Base and Kabat Numbering
NOT UNDERLINED: Framework
underlined: CDR

Figure 11 mAb 84 VH

The amino acids not underlined correspond to framework regions and underlined corresponds to CDRs.

```
1      AGACGGCCAGTGATTGTATACGACTCACTATAGGGCGAATTGGGCCCGACGTCGCATGCT

61     CCCGGCCGCCATGGCCGCGGGATTCAGGTGCAGCTGCAGCAGTCAGGAGGAGGCTTGGTG
1                        Q  V  Q  L  Q  Q  S  G  G  G  L  V

121    CAACCTGGAGGATCCATGAAACTCTCCTGTGTTGCCTCTGGATTCACTTTCAGTAACTAC
13      Q  P  G  G  S  M  K  L  S  C  V  A  S  G  F  T  F  S  N  Y

181    TGGATGAACTGGGTCCGCCAGTCTCCAGAGAAGGGGCTTGAGTGGGTTGCTGAAATTAGA
33      W  M  N  W  V  R  Q  S  P  E  K  G  L  E  W  V  A  E  I  R

241    TTGAAATCTAATAATTATGCAACACATTATGCGGAGTCTGTGAAAGGGAGGTTCACCATC
53      L  K  S  N  N  Y  A  T  H  Y  A  E  S  V  K  G  R  F  T  I

301    TCAAGAGATGATTCCAAAAGTAGTGTCTACCTGCAAATGAACAACTTAAGAGCTGAAGAC
73      S  R  D  D  S  K  S  S  V  Y  L  Q  M  N  N  L  R  A  E  D

361    ACTGGCATTTATTACTGTACGGGGGAGAGGGCCTGGGGCCAAGGGACCACGGTCACCGTC
93      T  G  I  Y  Y  C  T  G  E  R  A  W  G  Q  G  T  T  V  T  V

421    TCCTCAAATCACTAGTGCGGCCGCCTGCAGGTCGACCATATGGGAGAGCTCCCAACGCGT
113     S  S

481    TGGATGCATAGCTTGAGTATTCTATAGTGTCACCTAAATAGCTTGGCGTAATCATGGTCA
541    TAGCTGTTTCCTGTGTGAAATTGTTATCCGCTCACAATTCCACACAACATACGAGCCGGA
601    AGCATAAAGTGTAAAGCCTGGGGTGCCTAATGAGTGAGCTAACTCACATTAATTGCGTTG
661    CGCTCACTGCCCGCTTTCCAGTCGGGAAACCTGTCGTGCCAGCTGCATTAATGAATCGGC
721    CAACGCGCGGGGAGAGGCGGTTTGCGTATTGGGCGCTCTTCGCTTCT
```

Based on V Base and Kabat Numbering
Not Underlined: Framework
Underlined: CDR

Figure 12

```
                        SEQUENCE LISTING

<160> NUMBER OF SEQ ID NOS: 10

<210> SEQ ID NO 1
<211> LENGTH: 528
<212> TYPE: PRT
<213> ORGANISM: Homo sapiens

<400> SEQUENCE: 1

Met Arg Cys Ala Leu Ala Leu Ser Ala Leu Leu Leu Leu Leu Ser Thr
1               5                   10                  15

Pro Pro Leu Leu Pro Ser Ser Pro Ser Pro Ser Pro Ser Pro Ser Pro
                20                  25                  30

Ser Gln Asn Ala Thr Gln Thr Thr Asp Ser Ser Asn Lys Thr Ala
            35                  40                  45

Pro Thr Pro Ala Ser Ser Val Thr Ile Met Ala Thr Asp Thr Ala Gln
    50                  55                  60

Gln Ser Thr Val Pro Thr Ser Lys Ala Asn Glu Ile Leu Ala Ser Val
65                  70                  75                  80

Lys Ala Thr Thr Leu Gly Val Ser Ser Asp Ser Pro Gly Thr Thr Thr
                85                  90                  95

Leu Ala Gln Gln Val Ser Gly Pro Val Asn Thr Thr Val Ala Arg Gly
            100                 105                 110

Gly Gly Ser Gly Asn Pro Thr Thr Thr Ile Glu Ser Pro Lys Ser Thr
        115                 120                 125

Lys Ser Ala Asp Thr Thr Thr Val Ala Thr Ser Thr Ala Thr Ala Lys
    130                 135                 140

Pro Asn Thr Thr Ser Ser Gln Asn Gly Ala Glu Asp Thr Thr Asn Ser
145                 150                 155                 160

Gly Gly Lys Ser Ser His Ser Val Thr Thr Asp Leu Thr Ser Thr Lys
                165                 170                 175

Ala Glu His Leu Thr Thr Pro His Pro Thr Ser Pro Leu Ser Pro Arg
            180                 185                 190

Gln Pro Thr Leu Thr His Pro Val Ala Thr Pro Thr Ser Ser Gly His
        195                 200                 205

Asp His Leu Met Lys Ile Ser Ser Ser Ser Thr Val Ala Ile Pro
    210                 215                 220

Gly Tyr Thr Phe Thr Ser Pro Gly Met Thr Thr Thr Leu Pro Ser Ser
225                 230                 235                 240
```

```
Val Ile Ser Gln Arg Thr Gln Gln Thr Ser Ser Gln Met Pro Ala Ser
                245                 250                 255

Ser Thr Ala Pro Ser Ser Gln Glu Thr Val Gln Pro Thr Ser Pro Ala
        260                 265                 270

Thr Ala Leu Arg Thr Pro Thr Leu Pro Glu Thr Met Ser Ser Ser Pro
        275                 280                 285

Thr Ala Ala Ser Thr Thr His Arg Tyr Pro Lys Thr Pro Ser Pro Thr
        290                 295                 300

Val Ala His Glu Ser Asn Trp Ala Lys Cys Glu Asp Leu Glu Thr Gln
305                 310                 315                 320

Thr Gln Ser Glu Lys Gln Leu Val Leu Asn Leu Thr Gly Asn Thr Leu
                325                 330                 335

Cys Ala Gly Gly Ala Ser Asp Glu Lys Leu Ile Ser Leu Ile Cys Arg
        340                 345                 350

Ala Val Lys Ala Thr Phe Asn Pro Ala Gln Asp Lys Cys Gly Ile Arg
        355                 360                 365

Leu Ala Ser Val Pro Gly Ser Gln Thr Val Val Lys Glu Ile Thr
        370                 375                 380

Ile His Thr Lys Leu Pro Ala Lys Asp Val Tyr Glu Arg Leu Lys Asp
385                 390                 395                 400

Lys Trp Asp Glu Leu Lys Glu Ala Gly Val Ser Asp Met Lys Leu Gly
                405                 410                 415

Asp Gln Gly Pro Pro Glu Glu Ala Glu Asp Arg Phe Ser Met Pro Leu
        420                 425                 430

Ile Ile Thr Ile Val Cys Met Ala Ser Phe Leu Leu Leu Val Ala Ala
        435                 440                 445

Leu Tyr Gly Cys Cys His Gln Arg Leu Ser Gln Arg Lys Asp Gln Gln
        450                 455                 460

Arg Leu Thr Glu Glu Leu Gln Thr Val Glu Asn Gly Tyr His Asp Asn
465                 470                 475                 480

Pro Thr Leu Glu Val Met Glu Thr Ser Ser Glu Met Gln Glu Lys Lys
                485                 490                 495

Val Val Ser Leu Asn Gly Glu Leu Gly Asp Ser Trp Ile Val Pro Leu
        500                 505                 510

Asp Asn Leu Thr Lys Asp Asp Leu Asp Glu Glu Glu Asp Thr His Leu
        515                 520                 525

<210> SEQ ID NO 2
<211> LENGTH: 558
<212> TYPE: PRT
<213> ORGANISM: Homo sapiens

<400> SEQUENCE: 2

Met Arg Cys Ala Leu Ala Leu Ser Ala Leu Leu Leu Leu Leu Ser Thr
1               5                   10                  15

Pro Pro Leu Leu Pro Ser Ser Pro Ser Pro Ser Pro Ser Pro Ser Gln
                20                  25                  30

Asn Ala Thr Gln Thr Thr Thr Asp Ser Ser Asn Lys Thr Ala Pro Thr
                35                  40                  45

Pro Ala Ser Ser Val Thr Ile Met Ala Thr Asp Thr Ala Gln Gln Ser
        50                  55                  60

Thr Val Pro Thr Ser Lys Ala Asn Glu Ile Leu Ala Ser Val Lys Ala
65                  70                  75                  80

Thr Thr Leu Gly Val Ser Ser Asp Ser Pro Gly Thr Thr Thr Leu Ala
                85                  90                  95
```

```
Gln Gln Val Ser Gly Pro Val Asn Thr Thr Val Ala Arg Gly Gly
            100                 105                 110

Ser Gly Asn Pro Thr Thr Thr Ile Glu Ser Pro Lys Ser Thr Lys Ser
            115                 120                 125

Ala Asp Thr Thr Thr Val Ala Thr Ser Thr Ala Thr Ala Lys Pro Asn
            130                 135                 140

Thr Thr Ser Ser Gln Asn Gly Ala Glu Asp Thr Thr Asn Ser Gly Gly
145                 150                 155                 160

Lys Ser Ser His Ser Val Thr Thr Asp Leu Thr Ser Thr Lys Ala Glu
                165                 170                 175

His Leu Thr Thr Pro His Pro Thr Ser Pro Leu Ser Pro Arg Gln Pro
            180                 185                 190

Thr Ser Thr His Pro Val Ala Thr Pro Thr Ser Ser Gly His Asp His
            195                 200                 205

Leu Met Lys Ile Ser Ser Ser Ser Thr Val Ala Ile Pro Gly Tyr
    210                 215                 220

Thr Phe Thr Ser Pro Gly Met Thr Thr Thr Leu Leu Glu Thr Val Phe
225                 230                 235                 240

His His Val Ser Gln Ala Gly Leu Glu Leu Leu Thr Ser Gly Asp Leu
            245                 250                 255

Pro Thr Leu Ala Ser Gln Ser Ala Gly Ile Thr Ala Ser Ser Val Ile
            260                 265                 270

Ser Gln Arg Thr Gln Gln Thr Ser Ser Gln Met Pro Ala Ser Ser Thr
        275                 280                 285

Ala Pro Ser Ser Gln Glu Thr Val Gln Pro Thr Ser Pro Ala Thr Ala
        290                 295                 300

Leu Arg Thr Pro Thr Leu Pro Glu Thr Met Ser Ser Ser Pro Thr Ala
305                 310                 315                 320

Ala Ser Thr Thr His Arg Tyr Pro Lys Thr Pro Ser Pro Thr Val Ala
                325                 330                 335

His Glu Ser Asn Trp Ala Lys Cys Glu Asp Leu Glu Thr Gln Thr Gln
            340                 345                 350

Ser Glu Lys Gln Leu Val Leu Asn Leu Thr Gly Asn Thr Leu Cys Ala
        355                 360                 365

Gly Gly Ala Ser Asp Glu Lys Leu Ile Ser Leu Ile Cys Arg Ala Val
    370                 375                 380

Lys Ala Thr Phe Asn Pro Ala Gln Asp Lys Cys Gly Ile Arg Leu Ala
385                 390                 395                 400

Ser Val Pro Gly Ser Gln Thr Val Val Lys Glu Ile Thr Ile His
            405                 410                 415

Thr Lys Leu Pro Ala Lys Asp Val Tyr Glu Arg Leu Lys Asp Lys Trp
            420                 425                 430

Asp Glu Leu Lys Glu Ala Gly Val Ser Asp Met Lys Leu Gly Asp Gln
        435                 440                 445

Gly Pro Pro Glu Glu Ala Glu Asp Arg Phe Ser Met Pro Leu Ile Ile
        450                 455                 460

Thr Ile Val Cys Met Ala Ser Phe Leu Leu Leu Val Ala Ala Leu Tyr
465                 470                 475                 480

Gly Cys Cys His Gln Arg Leu Ser Gln Arg Lys Asp Gln Gln Arg Leu
                485                 490                 495

Thr Glu Glu Leu Gln Thr Val Glu Asn Gly Tyr His Asp Asn Pro Thr
            500                 505                 510
```

| | | | | | | | | | | | |
|---|---|---|---|---|---|---|---|---|---|---|---|
|Leu|Glu|Val|Met|Glu|Thr|Ser|Ser|Glu|Met|Gln|Glu|Lys|Val|Val|
| | | |515| | |520| | | |525| | | | |

Ser Leu Asn Gly Glu Leu Gly Asp Ser Trp Ile Val Pro Leu Asp Asn
530                     535                     540

Leu Thr Lys Asp Asp Leu Asp Glu Glu Asp Thr His Leu
545                 550                 555

<210> SEQ ID NO 3
<211> LENGTH: 560
<212> TYPE: PRT
<213> ORGANISM: Homo sapiens

<400> SEQUENCE: 3

Met Arg Cys Ala Leu Ala Leu Ser Ala Leu Leu Leu Leu Ser Thr
1               5                   10                  15

Pro Pro Leu Leu Pro Ser Ser Pro Ser Pro Ser Pro Ser Pro
            20                  25                  30

Ser Gln Asn Ala Thr Gln Thr Thr Asp Ser Ser Asn Lys Thr Ala
                35                  40                  45

Pro Thr Pro Ala Ser Ser Val Thr Ile Met Ala Thr Asp Thr Ala Gln
50                  55                  60

Gln Ser Thr Val Pro Thr Ser Lys Ala Asn Glu Ile Leu Ala Ser Val
65                  70                  75                  80

Lys Ala Thr Thr Leu Gly Val Ser Asp Ser Pro Gly Thr Thr Thr
                85                  90                  95

Leu Ala Gln Gln Val Ser Gly Pro Val Asn Thr Thr Val Ala Arg Gly
                100                 105                 110

Gly Ser Ser Gly Asn Pro Thr Thr Ile Glu Ser Pro Lys Ser Thr
                115                 120                 125

Lys Ser Ala Asp Thr Thr Thr Val Ala Thr Ser Thr Ala Thr Ala Lys
                130                 135                 140

Pro Asn Thr Thr Ser Ser Gln Asn Gly Ala Glu Asp Thr Thr Asn Ser
145                 150                 155                 160

Gly Gly Lys Ser Ser His Ser Val Thr Thr Asp Leu Thr Ser Thr Lys
                165                 170                 175

Ala Glu His Leu Thr Thr Pro His Pro Thr Ser Pro Leu Ser Pro Arg
                180                 185                 190

Gln Pro Thr Leu Thr His Pro Val Ala Thr Pro Thr Ser Ser Gly His
                195                 200                 205

Asp His Leu Met Lys Ile Ser Ser Ser Ser Thr Val Ala Ile Pro
210                 215                 220

Gly Tyr Thr Phe Thr Ser Pro Gly Met Thr Thr Thr Leu Leu Glu Thr
225                 230                 235                 240

Val Phe His His Val Ser Gln Ala Gly Leu Glu Leu Leu Thr Ser Gly
                245                 250                 255

Asp Leu Pro Thr Leu Ala Ser Gln Ser Ala Gly Ile Thr Ala Ser Ser
                260                 265                 270

Val Ile Ser Gln Arg Thr Gln Gln Thr Ser Ser Gln Met Pro Ala Ser
                275                 280                 285

Ser Thr Ala Pro Ser Ser Gln Glu Thr Val Gln Pro Thr Ser Pro Ala
                290                 295                 300

Thr Ala Leu Arg Thr Pro Thr Leu Pro Glu Thr Met Ser Ser Ser Pro
305                 310                 315                 320

Thr Ala Ala Ser Thr Thr His Arg Tyr Pro Lys Thr Pro Ser Pro Thr
                325                 330                 335

```
Val Ala His Glu Ser Asn Trp Ala Lys Cys Glu Asp Leu Glu Thr Gln
            340                 345                 350

Thr Gln Ser Glu Lys Gln Leu Val Leu Asn Leu Thr Gly Asn Thr Leu
        355                 360                 365

Cys Ala Gly Gly Ala Ser Asp Glu Lys Leu Ile Ser Leu Ile Cys Arg
    370                 375                 380

Ala Val Lys Ala Thr Phe Asn Pro Ala Gln Asp Lys Cys Gly Ile Arg
385                 390                 395                 400

Leu Ala Ser Val Pro Gly Ser Gln Thr Val Val Lys Glu Ile Thr
                405                 410                 415

Ile His Thr Lys Leu Pro Ala Lys Asp Val Tyr Glu Arg Leu Lys Asp
                420                 425                 430

Lys Trp Asp Glu Leu Lys Glu Ala Gly Val Ser Asp Met Lys Leu Gly
                435                 440                 445

Asp Gln Gly Pro Pro Glu Glu Ala Glu Asp Arg Phe Ser Met Pro Leu
    450                 455                 460

Ile Ile Thr Ile Val Cys Met Ala Ser Phe Leu Leu Leu Val Ala Ala
465                 470                 475                 480

Leu Tyr Gly Cys Cys His Gln Arg Leu Ser Gln Arg Lys Asp Gln Gln
                485                 490                 495

Arg Leu Thr Glu Glu Leu Gln Thr Val Glu Asn Gly Tyr His Asp Asn
            500                 505                 510

Pro Thr Leu Glu Val Met Glu Thr Ser Ser Glu Met Gln Glu Lys Lys
        515                 520                 525

Val Val Ser Leu Asn Gly Glu Leu Gly Asp Ser Trp Ile Val Pro Leu
    530                 535                 540

Asp Asn Leu Thr Lys Asp Asp Leu Asp Glu Glu Asp Thr His Leu
545                 550                 555                 560

<210> SEQ ID NO 4
<211> LENGTH: 107
<212> TYPE: PRT
<213> ORGANISM: Artificial Sequence
<220> FEATURE:
<223> OTHER INFORMATION: Synthetic sequence: VL chain of mAb 84

<400> SEQUENCE: 4

Asp Ile Glu Leu Thr Gln Ser Pro Ala Ile Met Ser Ala Ser Pro Gly
1               5                  10                  15

Glu Lys Val Thr Met Thr Cys Ser Ala Ser Ser Ser Val Asn Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser Tyr Pro Tyr Thr
                85                  90                  95

Phe Gly Gly Gly Thr Lys Leu Glu Ile Lys Arg
            100                 105

<210> SEQ ID NO 5
<211> LENGTH: 798
<212> TYPE: DNA
<213> ORGANISM: Artificial Sequence
```

<220> FEATURE:
<223> OTHER INFORMATION: Synthetic sequence: Encoding polynucleotide
      sequence of the VL chain of mAb 84
<220> FEATURE:
<221> NAME/KEY: CDS
<222> LOCATION: (103)..(423)

<400> SEQUENCE: 5

```
acgccagcta tttaggtgac actatagaat actcaagcta tgcatccaac gcgttgggag      60
ctctcccata tggtcgacct gcaggcggcc gcactagtga tt gac att gag ctc        114
                                              Asp Ile Glu Leu
                                                1 acc cag tct cca gca atc atg tct gca tct cca ggg gag aag gtc acc       162
Thr Gln Ser Pro Ala Ile Met Ser Ala Ser Pro Gly Glu Lys Val Thr
  5                  10                  15                  20 atg acc tgc agt gcc agc tca agt gta aat tac atg tac tgg tac cag       210
Met Thr Cys Ser Ala Ser Ser Ser Val Asn Tyr Met Tyr Trp Tyr Gln
                 25                  30                  35 cag aag cca gga tcc tcc ccc aga ctc ctg att tat gac aca tcc aac       258
Gln Lys Pro Gly Ser Ser Pro Arg Leu Leu Ile Tyr Asp Thr Ser Asn
             40                  45                  50 ctg gct tct gga gtc cct gtt cgc ttc agt ggc agt ggg tct ggg acc       306
Leu Ala Ser Gly Val Pro Val Arg Phe Ser Gly Ser Gly Ser Gly Thr
         55                  60                  65 tct tac tct ctc aca atc agc cga atg gag gct gaa gat gct gcc act       354
Ser Tyr Ser Leu Thr Ile Ser Arg Met Glu Ala Glu Asp Ala Ala Thr
 70                  75                  80 tat tac tgc cag cag tgg agt agt tac ccg tac acg ttc gga ggg ggg       402
Tyr Tyr Cys Gln Gln Trp Ser Ser Tyr Pro Tyr Thr Phe Gly Gly Gly
 85                  90                  95                 100 acc aag ctg gaa ata aaa cgg aatcccgcgg ccatgcggc cgggagcatg           453
Thr Lys Leu Glu Ile Lys Arg
                 105 cgacgtcggg cccaattcgc cctatagtga gtcgtattac aattcactgg ccgtcgtttt     513 acaacgtcgt gactgggaaa accctggcgt tacccaactt aatcgccttg cagcacatcc     573 ccctttcgcc agctggcgta atagcgaaga ggcgcgcacc gatcgccctt ctcaacagtt     633 gcgcagcctg aatagcgaat agacgcgccc tgtagcggcg cattatgcgc ggcggggtgt     693 ggtggttacg cgcagcgtga ccgctacact tgtcagcgcc ctagcgccgc tcctttcgct     753 ttcttccctt cctttctcgc cacgttcgcc ggcttgctcg tcagg                     798
```

<210> SEQ ID NO 6
<211> LENGTH: 114
<212> TYPE: PRT
<213> ORGANISM: Artificial Sequence
<220> FEATURE:
<223> OTHER INFORMATION: Synthetic sequence:VH chain of mAb 84

<400> SEQUENCE: 6

```
Gln Val Gln Leu Gln Gln Ser Gly Gly Gly Leu Val Gln Pro Gly Gly
  1               5                  10                  15

Ser Met Lys Leu Ser Cys Val Ala Ser Gly Phe Thr Phe Ser Asn Tyr
                 20                  25                  30

Trp Met Asn Trp Val Arg Gln Ser Pro Glu Lys Gly Leu Glu Trp Val
             35                  40                  45

Ala Glu Ile Arg Leu Lys Ser Asn Asn Tyr Ala Thr His Tyr Ala Glu
         50                  55                  60

Ser Val Lys Gly Arg Phe Thr Ile Ser Arg Asp Asp Ser Lys Ser Ser
 65                  70                  75                  80
```

```
Val Tyr Leu Gln Met Asn Asn Leu Arg Ala Glu Asp Thr Gly Ile Tyr
                85                  90                  95

Tyr Cys Thr Gly Glu Arg Ala Trp Gly Gln Gly Thr Thr Val Thr Val
            100                 105                 110

Ser Ser

<210> SEQ ID NO 7
<211> LENGTH: 767
<212> TYPE: DNA
<213> ORGANISM: Artificial Sequence
<220> FEATURE:
<223> OTHER INFORMATION: Synthetic sequence: Encoding polynucleotide
      sequence of the VH chain of mAb 84
<220> FEATURE:
<221> NAME/KEY: CDS
<222> LOCATION: (85)..(426)

<400> SEQUENCE: 7
agacggccag tgattgtata cgactcacta tagggcgaat tgggcccgac gtcgcatgct    60
cccggccgcc atggccgcgg gatt cag gtg cag ctg cag cag tca gga gga     111
                          Gln Val Gln Leu Gln Gln Ser Gly Gly
                            1               5 ggc ttg gtg caa cct gga gga tcc atg aaa ctc tcc tgt gtt gcc tct    159
Gly Leu Val Gln Pro Gly Gly Ser Met Lys Leu Ser Cys Val Ala Ser
 10              15                  20                  25 gga ttc act ttc agt aac tac tgg atg aac tgg gtc cgc cag tct cca    207
Gly Phe Thr Phe Ser Asn Tyr Trp Met Asn Trp Val Arg Gln Ser Pro
                 30                  35                  40 gag aag ggg ctt gag tgg gtt gct gaa att aga ttg aaa tct aat aat    255
Glu Lys Gly Leu Glu Trp Val Ala Glu Ile Arg Leu Lys Ser Asn Asn
             45                  50                  55 tat gca aca cat tat gcg gag tct gtg aaa ggg agg ttc acc atc tca    303
Tyr Ala Thr His Tyr Ala Glu Ser Val Lys Gly Arg Phe Thr Ile Ser
         60                  65                  70 aga gat gat tcc aaa agt agt gtc tac ctg caa atg aac aac tta aga    351
Arg Asp Asp Ser Lys Ser Ser Val Tyr Leu Gln Met Asn Asn Leu Arg
 75                  80                  85 gct gaa gac act ggc att tat tac tgt acg ggg gag agg gcc tgg ggc    399
Ala Glu Asp Thr Gly Ile Tyr Tyr Cys Thr Gly Glu Arg Ala Trp Gly
 90                  95                 100                 105 caa ggg acc acg gtc acc gtc tcc tca aatcactagt gcggccgcct           446
Gln Gly Thr Thr Val Thr Val Ser Ser
                 110 gcaggtcgac catatgggag agctcccaac gcgttggatg catagcttga gtattctata   506 gtgtcaccta atagcttgg cgtaatcatg gtcatagctg tttcctgtgt gaaattgtta    566 tccgctcaca attccacaca acatacgagc cggaagcata aagtgtaaag cctggggtgc   626 ctaatgagtg agctaactca cattaattgc gttgcgctca ctgcccgctt tccagtcggg   686 aaacctgtcg tgccagctgc attaatgaat cggccaacgc gcgggagag gcggtttgcg    746 tattgggcgc tcttcgcttc t                                            767

<210> SEQ ID NO 8
<211> LENGTH: 558
<212> TYPE: PRT
<213> ORGANISM: Homo sapiens

<400> SEQUENCE: 8

Met Arg Cys Ala Leu Ala Leu Ser Ala Leu Leu Leu Leu Leu Ser Thr
 1               5                  10                  15
```

```
Pro Pro Leu Leu Pro Ser Ser Pro Ser Pro Ser Pro Ser Gln
            20              25              30

Asn Ala Thr Gln Thr Thr Thr Asp Ser Ser Asn Lys Thr Ala Pro Thr
        35              40              45

Pro Ala Ser Ser Val Thr Ile Met Ala Thr Asp Thr Ala Gln Gln Ser
50              55              60

Thr Val Pro Thr Ser Lys Ala Asn Glu Ile Leu Ala Ser Val Lys Ala
65              70              75              80

Thr Thr Leu Gly Val Ser Ser Asp Ser Pro Gly Thr Thr Leu Ala
                85              90              95

Gln Gln Val Ser Gly Pro Val Asn Thr Thr Val Ala Arg Gly Gly Gly
            100             105             110

Ser Gly Asn Pro Thr Thr Thr Ile Glu Ser Pro Lys Ser Thr Lys Ser
            115             120             125

Ala Asp Thr Thr Thr Val Ala Thr Ser Thr Ala Thr Ala Lys Pro Asn
130             135             140

Thr Thr Ser Ser Gln Asn Gly Ala Glu Asp Thr Thr Asn Ser Gly Gly
145             150             155             160

Lys Ser Ser His Ser Val Thr Thr Asp Leu Thr Ser Thr Lys Ala Glu
                165             170             175

His Leu Thr Thr Pro His Pro Thr Ser Pro Leu Ser Pro Arg Gln Pro
            180             185             190

Thr Ser Thr His Pro Val Ala Thr Pro Thr Ser Ser Gly His Asp His
            195             200             205

Leu Met Lys Ile Ser Ser Ser Ser Thr Val Ala Ile Pro Gly Tyr
    210             215             220

Thr Phe Thr Ser Pro Gly Met Thr Thr Thr Leu Leu Glu Thr Val Phe
225             230             235             240

His His Val Ser Gln Ala Gly Leu Glu Leu Leu Thr Ser Gly Asp Leu
            245             250             255

Pro Thr Leu Ala Ser Gln Ser Ala Gly Ile Thr Ala Ser Ser Val Ile
            260             265             270

Ser Gln Arg Thr Gln Gln Thr Ser Ser Gln Met Pro Ala Ser Ser Thr
    275             280             285

Ala Pro Ser Ser Gln Glu Thr Val Gln Pro Thr Ser Pro Ala Thr Ala
    290             295             300

Leu Arg Thr Pro Thr Leu Pro Glu Thr Met Ser Ser Ser Pro Thr Ala
305             310             315             320

Ala Ser Thr Thr His Arg Tyr Pro Lys Thr Pro Ser Pro Thr Val Ala
            325             330             335

His Glu Ser Asn Trp Ala Lys Cys Glu Asp Leu Glu Thr Gln Thr Gln
            340             345             350

Ser Glu Lys Gln Leu Val Leu Asn Leu Thr Gly Asn Thr Leu Cys Ala
            355             360             365

Gly Gly Ala Ser Asp Glu Lys Leu Ile Ser Leu Ile Cys Arg Ala Val
            370             375             380

Lys Ala Thr Phe Asn Pro Ala Gln Asp Lys Cys Gly Ile Arg Leu Ala
385             390             395             400

Ser Val Pro Gly Ser Gln Thr Val Val Lys Glu Ile Thr Ile His
            405             410             415

Thr Lys Leu Pro Ala Lys Asp Val Tyr Glu Arg Leu Lys Asp Lys Trp
            420             425             430
```

```
Asp Glu Leu Lys Glu Ala Gly Val Ser Asp Met Lys Leu Gly Asp Gln
            435                 440                 445
Gly Pro Pro Glu Glu Ala Glu Asp Arg Phe Ser Met Pro Leu Ile Ile
450                 455                 460
Thr Ile Val Cys Met Ala Ser Phe Leu Leu Val Ala Ala Leu Tyr
465                 470                 475                 480
Gly Cys Cys His Gln Arg Leu Ser Gln Arg Lys Asp Gln Gln Arg Leu
                485                 490                 495
Thr Glu Glu Leu Gln Thr Val Glu Asn Gly Tyr His Asp Asn Pro Thr
            500                 505                 510
Leu Glu Val Met Glu Thr Ser Ser Glu Met Gln Glu Lys Lys Val Val
            515                 520                 525
Ser Leu Asn Gly Glu Leu Gly Asp Ser Trp Ile Val Pro Leu Asp Asn
        530                 535                 540
Leu Thr Lys Asp Asp Leu Asp Glu Glu Glu Asp Thr His Leu
545                 550                 555

<210> SEQ ID NO 9
<211> LENGTH: 526
<212> TYPE: PRT
<213> ORGANISM: Homo sapiens

<400> SEQUENCE: 9

Met Arg Cys Ala Leu Ala Leu Ser Ala Leu Leu Leu Leu Leu Ser Thr
1               5                   10                  15
Pro Pro Leu Leu Pro Ser Ser Pro Ser Pro Ser Pro Ser Pro Ser Gln
            20                  25                  30
Asn Ala Thr Gln Thr Thr Thr Asp Ser Ser Asn Lys Thr Ala Pro Thr
            35                  40                  45
Pro Ala Ser Ser Val Thr Ile Met Ala Thr Asp Thr Ala Gln Gln Ser
50                  55                  60
Thr Val Pro Thr Ser Lys Ala Asn Glu Ile Leu Ala Ser Val Lys Ala
65                  70                  75                  80
Thr Thr Leu Gly Val Ser Ser Asp Ser Pro Gly Thr Thr Thr Leu Ala
                85                  90                  95
Gln Gln Val Ser Gly Pro Val Asn Thr Thr Val Ala Arg Gly Gly Gly
            100                 105                 110
Ser Gly Asn Pro Thr Thr Thr Ile Glu Ser Pro Lys Ser Thr Lys Ser
            115                 120                 125
Ala Asp Thr Thr Thr Val Ala Thr Ser Thr Ala Thr Ala Lys Pro Asn
130                 135                 140
Thr Thr Ser Ser Gln Asn Gly Ala Glu Asp Thr Thr Asn Ser Gly Gly
145                 150                 155                 160
Lys Ser Ser His Ser Val Thr Thr Asp Leu Thr Ser Thr Lys Ala Glu
                165                 170                 175
His Leu Thr Thr Pro His Pro Thr Ser Pro Leu Ser Pro Arg Gln Pro
            180                 185                 190
Thr Ser Thr His Pro Val Ala Thr Pro Thr Ser Ser Gly His Asp His
            195                 200                 205
Leu Met Lys Ile Ser Ser Ser Ser Thr Val Ala Ile Pro Gly Tyr
210                 215                 220
Thr Phe Thr Ser Pro Gly Met Thr Thr Thr Leu Pro Ser Ser Val Ile
225                 230                 235                 240
Ser Gln Arg Thr Gln Gln Thr Ser Ser Gln Met Pro Ala Ser Ser Thr
                245                 250                 255
```

```
Ala Pro Ser Ser Gln Glu Thr Val Gln Pro Thr Ser Pro Ala Thr Ala
            260                 265                 270

Leu Arg Thr Pro Thr Leu Pro Glu Thr Met Ser Ser Ser Pro Thr Ala
            275                 280                 285

Ala Ser Thr Thr His Arg Tyr Pro Lys Thr Pro Ser Pro Thr Val Ala
            290                 295                 300

His Glu Ser Asn Trp Ala Lys Cys Glu Asp Leu Glu Thr Gln Thr Gln
305                 310                 315                 320

Ser Glu Lys Gln Leu Val Leu Asn Leu Thr Gly Asn Thr Leu Cys Ala
            325                 330                 335

Gly Gly Ala Ser Asp Glu Lys Leu Ile Ser Leu Ile Cys Arg Ala Val
            340                 345                 350

Lys Ala Thr Phe Asn Pro Ala Gln Asp Lys Cys Gly Ile Arg Leu Ala
            355                 360                 365

Ser Val Pro Gly Ser Gln Thr Val Val Lys Glu Ile Thr Ile His
            370                 375                 380

Thr Lys Leu Pro Ala Lys Asp Val Tyr Glu Arg Leu Lys Asp Lys Trp
385                 390                 395                 400

Asp Glu Leu Lys Glu Ala Gly Val Ser Asp Met Lys Leu Gly Asp Gln
            405                 410                 415

Gly Pro Pro Glu Glu Ala Glu Asp Arg Phe Ser Met Pro Leu Ile Ile
            420                 425                 430

Thr Ile Val Cys Met Ala Ser Phe Leu Leu Leu Val Ala Ala Leu Tyr
            435                 440                 445

Gly Cys Cys His Gln Arg Leu Ser Gln Arg Lys Asp Gln Gln Arg Leu
            450                 455                 460

Thr Glu Glu Leu Gln Thr Val Glu Asn Gly Tyr His Asp Asn Pro Thr
465                 470                 475                 480

Leu Glu Val Met Glu Thr Ser Ser Glu Met Gln Glu Lys Lys Val Val
            485                 490                 495

Ser Leu Asn Gly Glu Leu Gly Asp Ser Trp Ile Val Pro Leu Asp Asn
            500                 505                 510

Leu Thr Lys Asp Asp Leu Asp Glu Glu Asp Thr His Leu
            515                 520                 525

<210> SEQ ID NO 10
<211> LENGTH: 4
<212> TYPE: PRT
<213> ORGANISM: Artificial sequence
<220> FEATURE:
<223> OTHER INFORMATION: Synthetic sequence: Spacer molecule

<400> SEQUENCE: 10

Gly Glu Asn Arg
1
```

METHODS FOR IDENTIFYING CANDIDATE CYTOTOXIC ANTIBODY MOLECULES

PRIORITY CLAIM

This application is a national phase application under 35 USC §371 of PCT International Application No. PCT/SG2011/000262 (published PCT Application No. WO/2012/011876 A 1), filed Jul. 21, 2011, which claims priority from U.S. Provisional Application No. 61/366,193 filed Jul. 21, 2010.

SEQUENCE LISTING

In accordance with 37 CFR 1.52(e)(5), a Sequence Listing in the form of an ASCII text filed (entitled "YF8540. txt," created on Jan. 18, 2013, and 31 kilobyte) is incorporated herein by reference in its entirety.

FIELD OF THE INVENTION

The present invention relates to methods for screening candidate antibody molecules which bind to podocalyxin-like protein (PODXL) and/or to undifferentiated pluripotent stem cells and particularly, although not exclusively, to methods for identifying candidate cytotoxic antibody molecules.

BACKGROUND TO THE INVENTION

Embryonic and other pluripotent stem cells have great potential in therapy. Such cells can be directed to differentiate into specific cell types and offer the possibility of a renewable source of replacement cells and tissues, for example, for use in regenerative medicine to repair tissues which have been damaged by disease or injury.

However, the use of embryonic stem cells in medicine is limited due to the significant ethical concerns associated with the use of embryos. The Yamanaka Lab[2] and Thomson Lab[3] demonstrated that human fibroblasts can be reprogrammed by the transient overexpression of a small number of genes into induced pluripotent stem cells (IPSCs) which functionally and phenotypically resemble embryonic stem cells (ESCs). Thus, pluripotent stem cells can be obtained without the need for the destruction of embryos.

Some IPSCs, like hESC, express Oct-4 and other cell surface markers, such as Tra-1-60/81 and SSEA-3/4. However, IPSCs are not identical to ESCs, as shown by a slower doubling time[11], differences in the global gene-expression patterns[2,3] and DNA methylation status[2]. It remains unknown whether nuclear reprogramming is complete[10] and thus whether IPSCs follow a similar pathway to hESCs during differentiation.

This important breakthrough raises the possibility that cellular therapies using patient-specific input cells may be a reality in the future. Unlike hESC where there are ethical concerns and possible issues of immune rejection, IPSCs can be generated from a donor, reprogrammed, differentiated to the appropriate cell type and transplanted back into the donor.

Prior to the publication of reports that IPSCs had been successfully generated from human cells, we described the generation of a panel of monoclonal antibodies (mAbs) against surface antigens on undifferentiated hESCs[1] in WO 2007/102787, the contents of which is hereby incorporated in this application by reference. These mAbs showed strong reactivity against undifferentiated, but not differentiated (embryoid bodies), hESC lines.

The mAbs did not cross react with mouse fibroblasts, and showed weak to no reactivity against human embryonal carcinoma cells. Thus these mAbs exhibited very high specificity binding to hESCs, and this binding was lost as the hESCs differentiated. The monoclonal antibody, mAb 84, is an IgM which specifically binds and kills undifferentiated human embryonic stem cells (hESC) (Tan, 2009[29]). mAb 84 induced cell death of undifferentiated, but not differentiated hESC within 30 min of incubation, and immunoprecipitation of the mAb-antigen complex revealed that the antigen is podocalyxin-like protein-1 (PODXL). Importantly, the absence of tumour formation is observed when hESC were treated with mAb 84 prior to transplantation into SCID mice. This earlier data indicates that mAb84 may be useful in eliminating residual undifferentiated hESC from differentiated cell populations for clinical applications.

In addition to generating antibodies which were cytotoxic against undifferentiated hESCs, such as mAb84, in WO 2007/102787 we also produced mAbs which were non-cytotoxic against undifferentiated hESCs. One notable non-cytotoxic antibody was mAb 85.

Furthermore, in WO/2010/033084, the contents of which are hereby incorporated by reference, we reported the discovery of mAbs that bind to and characterize IPSCs. We reported that mAb 84 was cytotoxic against IPSCs, and mAb85 was non-cytotoxic against IPSCs.

Although undifferentiated stem cells may be used in cell therapy, it is considered to be beneficial to use cells which have started to differentiate, or are differentiated. Methods of encouraging stem cells to differentiate into particular cell lineages are well known in the art. Once the differentiation process has started or proceeded, it is beneficial to remove or destroy undifferentiated hESCs in a sample which may otherwise form undesirable teratomas. Teratomas typically contain a mixture of differentiated or partly differentiated cell types. Despite the potential of IPSC therapy, the problem of teratoma formation by residual IPSC after differentiation remains and needs to be addressed.

Thus, mAb 84 can potentially be used for separation and removal of residual undifferentiated hESC or undifferentiated IPSC from differentiated cell populations.

Thus, it can be seen that it is useful to identify, isolate or separate undifferentiated pluripotent stem cells (since they can be used themselves in therapy or can be encouraged to differentiate into a particular cell lineage which can be used in therapy). It is also useful to remove or destroy undifferentiated pluripotent stem cells from a mixture of cells where some of the cells have started to differentiate, or are differentiated, since these differentiated cells are useful in therapy.

It can also be seen that there is a need to identify further antibodies, in addition to mAb84, which are specifically cytotoxic against both hESCs and IPSCs. Such antibodies could then be useful in methods for separation and removal of residual undifferentiated hESC or undifferentiated IPSC from differentiated cell populations, as described above.

The present invention arose as a result of ongoing studies by the present inventors into the areas described above. The inventors were in possession of cytotoxic and non-cytotoxic antibody molecules which were known to bind PODXL. They also knew that PODXL was a glycosylated protein. The inventors went on to investigate the importance of glycosylation for the binding of antibody molecules to PODXL. The inventors approached this by testing cytotoxic and non-cytotoxic antibody molecules in a glycan array against a range of different glycans. The inventors found that cytotoxic and non-cytotoxic antibody molecules bound to a common sequence of saccharide residues within glycans. Surprisingly, the inventors also found that there was a significant difference in the binding of cytotoxic and non-cytotoxic antibody molecules to this common sequence. Hence the inventors found that candidate cytotoxic antibody molecules can be selected based on their ability to bind glycans containing the common sequence.

SUMMARY OF THE INVENTION

The present inventors have discovered that candidate cytotoxic antibodies can be identified by their ability to bind glycans comprising Fucα1-2Galβ1-3GlcNAcβ1. In particular, the present inventors have discovered antibody molecules can be selected as candidates for having cytotoxic activity against a cell which expresses podocalyxin-like protein (PODXL), and/or against an undifferentiated pluripotent stem cell, based on their ability to bind glycans comprising Fucα1-2Galβ1-3GlcNAβ1. Methods for selecting candidate cytotoxic antibodies, based on their ability to bind glycans comprising Fucα1-2Galβ1-3GlcNAcβ1, uses of such glycans to select antibody molecules as candidates for having cytotoxic activity against a cell which expresses PODXL, and/or an undifferentiated pluripotent stem cell, and methods of destroying a cell which expresses PODXL, and/or an undifferentiated pluripotent stem cell, are provided.

In one aspect of the present invention there is provided a method of selecting an antibody molecule as a candidate for having cytotoxic activity against a cell which expresses podocalyxin-like protein (PODXL), wherein the antibody molecule binds PODXL, the method comprising the steps of:
 (i) comparing the binding of a PODXL-binding antibody molecule to a glycan comprising Fucα1-2Galβ1-3GlcNAc with the binding of a non-cytotoxic PODXL-binding antibody molecule to a glycan comprising Fucα1-2Galβ1-3GlcNAc; and
 (ii) selecting as a candidate cytotoxic antibody molecule a said PODXL-binding antibody molecule that has a relative binding to said glycan of 30 or more times greater than said non-cytotoxic PODXL-binding antibody molecule.

In another aspect of the present invention there is provided a method of selecting an antibody molecule as a candidate for having cytotoxic activity against an undifferentiated pluripotent stem cell, wherein the antibody molecule binds PODXL, the method comprising the steps of:
 (i) comparing the binding of a PODXL-binding antibody molecule to a glycan comprising Fucα1-2Galβ1-3GlcNAc with the binding of a non-cytotoxic PODXL-binding antibody molecule to a glycan comprising Fucα1-2Galβ1-3GlcNAc; and
 (ii) selecting as a candidate cytotoxic antibody molecule a said PODXL-binding antibody molecule that has a relative binding to said glycan of 30 or more times greater than said non-cytotoxic PODXL-binding antibody molecule.

In another aspect of the present invention there is provided a method of selecting an antibody molecule as a candidate for having cytotoxic activity against an undifferentiated pluripotent stem cell, the method comprising the steps of:
 (i) comparing the binding of a PODXL-binding antibody molecule to a glycan comprising Fucα1-2Galβ1-3GlcNAc with the binding of a non-cytotoxic PODXL-binding antibody molecule to a glycan comprising Fucα1-2Galβ1-3GlcNAc; and
 (ii) selecting as a candidate cytotoxic antibody molecule a said PODXL-binding antibody molecule that has a relative binding to said glycan of 30 or more times greater than said non-cytotoxic PODXL-binding antibody molecule.

In another aspect of the present invention there is provided a method of selecting an antibody molecule as a candidate for binding PODXL and having cytotoxic activity against a cell which expresses PODXL, the method comprising:
 (i) comparing the binding of an antibody molecule to a glycan comprising Fucα1-2Galβ1-3GlcNAc with the binding of a non-cytotoxic PODXL-binding antibody molecule to a glycan comprising Fucα1-2Galβ1-3GlcNAc; and
 (ii) selecting as a candidate for binding PODXL and having cytotoxic activity against a cell which expresses PODXL an antibody molecule that has a relative binding to said glycan of 30 or more times greater than said non-cytotoxic PODXL-binding antibody molecule.

In another aspect of the present invention there is provided a method of selecting an antibody molecule, from a sample containing such molecules, as a candidate for having cytotoxic activity against an undifferentiated pluripotent stem cell, wherein the antibody molecule binds PODXL, the method comprising the steps of:
 i) contacting the sample of antibody molecules with a plurality of glycans comprising Fucα1-2Galβ1-3GlcNAc;
 ii) selecting an antibody molecule having an absolute binding to at least one said glycan in the top 10% as a candidate cytotoxic antibody molecule.

In another aspect of the present invention there is provided a method of selecting an antibody molecule as a candidate for having cytotoxic activity against an undifferentiated pluripotent stem cell, wherein the antibody molecule binds PODXL, the method comprising the steps of:
 (i) measuring the binding of a PODXL-binding antibody molecule to a glycan comprising Fucα1-2Galβ1-3GlcNAc; and
 (ii) selecting as a candidate cytotoxic antibody molecule a said PODXL-binding antibody molecule that has a binding to said glycan greater than that of a non-cytotoxic PODXL-binding antibody molecule.

In another aspect of the present invention there is provided a method of selecting an antibody molecule as a candidate for having cytotoxic activity against a cell which expresses podocalyxin-like protein (PODXL), wherein the antibody molecule binds PODXL, the method comprising the steps of:
 (i) measuring the binding of a PODXL-binding antibody molecule to a glycan comprising Fucα1-2Galβ1-3GlcNAc; and
 (ii) selecting as a candidate cytotoxic antibody molecule a said PODXL-binding antibody molecule that has a binding to said glycan greater than that of a non-cytotoxic PODXL-binding antibody molecule.

In another aspect of the present invention there is provided a method of selecting an antibody molecule as a candidate for having cytotoxic activity against a cell which expresses podocalyxin-like protein (PODXL), wherein the antibody molecule binds PODXL, the method comprising the steps of:
 (i) comparing the binding of a PODXL-binding antibody molecule to a glycan comprising Fucα1-2Galβ1-3GlcNAc with the binding of a cytotoxic PODXL-binding antibody molecule to a glycan comprising Fucα1-2Galβ1-3GlcNAc; and
 (ii) selecting as a candidate cytotoxic antibody molecule a said PODXL-binding antibody molecule that has a binding to said glycan greater than that of the said cytotoxic PODXL-binding antibody molecule.

In another aspect of the present invention there is provided a method of selecting an antibody molecule as a candidate for having cytotoxic activity against an undifferentiated pluripotent stem cell, the method comprising the steps of:
  (i) comparing the binding of a PODXL-binding antibody molecule to a glycan comprising Fucα1-2Galβ1-3GlcNAc with the binding of a cytotoxic PODXL-binding antibody molecule to a glycan comprising Fucα1-2Galβ1-3GlcNAc; and
  (ii) selecting as a candidate cytotoxic antibody molecule a said PODXL-binding antibody molecule that has a binding to said glycan greater than that of the said cytotoxic PODXL-binding antibody molecule.

In another aspect of the present invention there is provided a method of selecting an antibody molecule as a candidate for having cytotoxic activity against an undifferentiated pluripotent stem cell, wherein the antibody molecule binds PODXL, the method comprising the steps of:
  (i) comparing the binding of a PODXL-binding antibody molecule to a glycan comprising Fucα1-2Galβ1-3GlcNAc with the binding of a cytotoxic PODXL-binding antibody molecule to a glycan comprising Fucα1-2Galβ1-3GlcNAc; and
  (ii) selecting as a candidate cytotoxic antibody molecule a said PODXL-binding antibody molecule that has a binding to said glycan greater than that of the said cytotoxic PODXL-binding antibody molecule.

In another aspect of the present invention there is provided a method of selecting an antibody molecule as a candidate for having cytotoxic activity against a cell which expresses PODXL, wherein the antibody molecule binds PODXL, the method comprising the steps of:
  i) contacting the antibody molecule with a glycan comprising Fucα1-2Galβ1-3GlcNAc;
  ii) comparing the relative binding of the glycan and the antibody molecule in (i) to the binding of the said glycan and a non-cytotoxic PODXL-binding antibody molecule;
  iii) selecting an antibody molecule having a relative binding of 30 or more times that of the said non-cytotoxic PODXL-binding antibody molecule as a candidate cytotoxic antibody molecule.

In another aspect of the present invention there is provided a method of selecting an antibody molecule as a candidate for having cytotoxic activity against an undifferentiated pluripotent stem cell, wherein the antibody molecule binds PODXL, the method comprising the steps of:
  i) contacting the antibody molecule with a glycan comprising Fucα1-2Galβ1-3GlcNAc;
  ii) comparing the relative binding of the glycan and the antibody molecule in (i) to the binding of the said glycan and a non-cytotoxic PODXL-binding antibody molecule;
  iii) selecting an antibody molecule having a relative binding of 30 or more times that of the said non-cytotoxic PODXL-binding antibody molecule as a candidate cytotoxic antibody molecule.

In another aspect of the present invention there is provided a method of selecting an antibody molecule as a candidate for having cytotoxic activity against an undifferentiated pluripotent stem cell, the method comprising the steps of:
  i) contacting a candidate antibody molecule with a glycan comprising Fucα1-2Galβ1-3GlcNAc;
  ii) comparing the relative binding of the glycan and the antibody molecule in (i) to the binding of the said glycan and a non-cytotoxic PODXL-binding antibody molecule;
  iii) selecting an antibody molecule having a relative binding of 30 or more times that of the said non-cytotoxic PODXL-binding antibody molecule as a candidate cytotoxic antibody molecule.

In another aspect of the present invention there is provided a method of selecting an antibody molecule as a candidate for having cytotoxic activity against a cell which expresses PODXL, wherein the antibody molecule binds PODXL, the method comprising the steps of:
  i) contacting the antibody molecule with a glycan comprising Fucα1-2Galβ1-3GlcNAc;
  ii) comparing the binding of the glycan and the antibody molecule in (i) to the binding of the said glycan and a cytotoxic PODXL-binding antibody molecule;
  (iii) selecting an antibody molecule having a binding equal to or greater than that of the said cytotoxic PODXL-binding antibody molecule as a candidate cytotoxic antibody molecule.

In another aspect of the present invention there is provided a method of selecting an antibody molecule as a candidate for having cytotoxic activity against an undifferentiated pluripotent stem cell, wherein the antibody molecule binds PODXL, the method comprising the steps of:
  i) contacting the antibody molecule with a glycan comprising Fucα1-2Galβ1-3GlcNAc;
  ii) comparing the binding of the glycan and the antibody molecule in (i) to the binding of the said glycan and a cytotoxic PODXL-binding antibody molecule;
  iii) selecting an antibody molecule having a binding equal to or greater than that of the said cytotoxic PODXL-binding antibody molecule as a candidate cytotoxic antibody molecule.

In another aspect of the present invention there is provided a method of selecting an antibody molecule as a candidate for having cytotoxic activity against an undifferentiated pluripotent stem cell, the method comprising the steps of:
  i) contacting a candidate antibody molecule with a glycan comprising Fucα1-2Galβ1-3GlcNAc;
  ii) comparing the binding of the glycan and the antibody molecule in (i) to the binding of the said glycan and a cytotoxic PODXL-binding antibody molecule;
  iii) selecting an antibody molecule having a binding equal to or greater than that of the said cytotoxic PODXL-binding antibody molecule as a candidate cytotoxic antibody molecule.

In some aspects the present invention comprises a method of selecting an antibody molecule from a sample containing such molecules, as a candidate for having cytotoxic activity against an undifferentiated pluripotent stem cell, wherein the antibody molecule binds PODXL, the method comprising the steps of:
  i) contacting the sample of antibody molecules with an array of glycans comprising Fucα1-2Galβ1-3GlcNAc;
  ii) selecting an antibody molecule having a direct binding in the top 10% as a candidate cytotoxic antibody molecule; and, optionally;
  iii) testing the candidate antibody for cytotoxic activity against a cell which expresses PODXL Methods of the present invention may also comprise one or more of the following steps;
  (a) determining binding between the candidate antibody molecule and the glycan comprising Fucα1-2Galβ1-3GlcNAc; and/or
  (b) contacting a non-cytotoxic PODXL-binding molecule with a glycan comprising Fucα1-2Galβ1-3GlcNAc; and/or (c) determining binding between a non-cytotoxic PODXL-binding molecule and the glycan comprising Fucα1-2Galβ1-3GlcNAc; and/or
(d) contacting a cytotoxic PODXL-binding molecule with a glycan comprising Fucα1-2Galβ1-3GlcNAc; and/or
(e) determining binding between a cytotoxic PODXL-binding molecule and the glycan comprising Fucα1-2Galβ1-3GlcNAc; and/or
(f) contacting the sample of antibody molecules with a plurality of glycans comprising Fucα1-2Galβ1-3GlcNAc and/or
(g) selecting an antibody molecule having an absolute binding to a said glycan in the top 10% as a candidate cytotoxic antibody molecule.

Methods of the present invention may also comprise the step of testing the candidate antibody for cytotoxic activity against a cell which expresses PODXL and/or against an undifferentiated pluripotent stem cell.

Methods of the present invention may also comprise the step of testing the candidate antibody for PODXL binding.

Methods of the present invention may comprise any combination of the steps described herein.

In preferred aspects the glycan comprises or consists of a glycan selected from the group:
Fucα1-2Galβ1-3GlcNAcβ1-3Galβ1-4Glcβ;
Neu5Acα2-6Galβ1-4GlcNAcβ1-6(Fucα1-2Galβ1-3GlcNAcβ1-3)Galβ-4Glc;
Fucα1-2Galβ1-3GlcNAcβ;
Fucα1-2Galβ1-3GlcNAβ1-3Galβ1-4Glcβ;
Fucα1-2Galβ1-3GlcNAcβ1-3GalNAc;
Fucα1-2Galβ1-3GlcNAcβ1-3(Galβ1-4GlcNAcβ1-6)Galβ1-4Glc;
Fucα1-2Galβ1-3GlcNAcβ1-3(Galβ1-4(Fucα1-3)GlcNAcβ1-6)Galβ1-4Glc;
Fucα1-2Galβ1-3GlcNAcβ; or
Fucα1-2Galβ1-3GlcNAβ1-2Manα1-3(Fucα1-2Galβ1-3GlcNAcβ1-2Manα1-6)Manβ1-4GlcNAcβ1-4GlcNAcβ;

In some aspects the glycan is selected from the group consisting of:
Fucα1-2Galβ1-3GlcNAcβ1-3Galβ1-4Glcβ-Sp8;
Neu5Acα2-6Galβ1-4GlcNAcβ1-6(Fucα1-2Galβ1-3GlcNAcβ1-3)Galβ-4Glc-Sp21;
Fucα1-2Galβ1-3GlcNAcβ-Sp0;
Fucα1-2Galβ1-3GlcNAcβ1-3Galβ1-4Glcβ-Sp10;
Fucα1-2Galβ1-3GlcNAcβ1-3GalNAc-Sp14;
Fucα1-2Galβ1-3GlcNAcβ1-3(Galβ1-4GlcNAcβ1-6)Galβ1-4Glc-Sp21;
Fucα1-2Galβ1-3GlcNAcβ1-3(Galβ1-4(Fucα1-3)GlcNAcβ1-6)Galβ1-4Glc-Sp21;
Fucα1-2Galβ1-3GlcNAcβ-Sp8; or
Fucα1-2Galβ1-3GlcNAcβ1-2Manα1-3(Fucα1-2Galβ1-3GlcNAcβ1-2Manα1-6)Manβ1-4GlcNAcβ1-4GlcNAcβ-Sp20;

In some aspects the glycans used in methods of the present invention are part of an array of glycans. In some aspects the glycans are immobilised on a solid support.

In some aspects the present invention comprises a PODXL-binding antibody molecule with candidate cytotoxic activity against an undifferentiated pluripotent stem cell and/or cytotoxic activity against a cell that expresses PODXL, obtained, identified, selected or produced by any of the methods described herein.

In another aspect the present invention comprises an antibody molecule with cytotoxic activity against an undifferentiated pluripotent stem cell obtained, identified, selected or produced by any of the methods described herein.

In some aspects the present invention comprises a method of destroying undifferentiated pluripotent stem cell(s) in a sample containing such cell(s), the method comprising contacting the cell or cells in the sample that express PODXL on their surface with a cytotoxic antibody. In preferred embodiments such cytotoxic antibodies are obtained, identified, selected or produced by any of the methods described herein.

In some aspects the present invention comprises a method of selecting an antibody molecule as a candidate for binding PODXL, the method comprising selecting an antibody molecule which binds a glycan comprising Fucα1-2Galβ1-3GlcNAc.

In another aspect, the present invention comprises a method of selecting an antibody molecule as a candidate for having cytotoxic activity against a cell which expresses PODXL and/or against an undifferentiated stem cell, the method comprising selecting an antibody molecule which binds a glycan comprising Fucα1-2Galβ1-3GlcNAc.

In some aspects the present invention comprises a kit of parts comprising a glycan comprising Fucα1-2Galβ1-3GlcNAc; a non-cytotoxic control molecule which preferably binds the glycan with a known binding intensity. The kit of parts may further comprise a cytotoxic control molecule which binds the glycan with a known binding intensity. The kit of parts may further comprises an agent that detects binding between the glycan and an antibody molecule. The cytotoxic control molecule may be mAb84 or an antibody having substantially equivalent binding affinity to PODXL and/or to a glycan comprising Fucα1-2Galβ1-3GlcNAc and/or substantially equivalent cytotoxic activity to cells expressing PODXL and/or to undifferentiated pluripotent stem cells. The non-cytotoxic control molecule may be mAb85 or an antibody having substantially equivalent binding affinity to PODXL and/or to a glycan comprising Fucα1-2Galβ1-3GlcNAc and/or substantially equivalent non-cytotoxic activity to cells expressing PODXL and/or to undifferentiated pluripotent stem cells.

In some aspects the present invention comprises the use of a glycan as described herein to select in vitro an antibody molecule that binds PODXL and/or is cytotoxic. In related aspects the present invention comprises the use of a glycan as described herein to determine in vitro whether an antibody molecule that is known to bind PODXL is cytotoxic. The determination may be whether the antibody molecule is cytotoxic to a cell which expresses PODXL and/or to an undifferentiated stem cell.

DESCRIPTION OF PREFERRED EMBODIMENTS

The present invention is concerned with methods for selecting an antibody molecule as a candidate for having cytotoxic activity against a cell that expresses podocalyxin-like protein (PODXL). The antibody molecule may be a candidate for having cytotoxic activity against an undifferentiated pluripotent stem cell.

The details of one or more embodiments of the invention are set forth in the accompanying description below including specific details of the best mode contemplated by the inventors for carrying out the invention, by way of example. It will be apparent to one skilled in the art that the present invention may be practiced without limitation to these specific details.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

Podocalyxin-Like Protein (PODXL)

The amino acid sequence of Podocalyxin-like protein 1 precursor herein referred to as Podocalyxin-like protein (PODXL) is given in FIG. 6 (SEQ ID NO: 1) and is also found in Accession No. O00592 of the NCBI protein sequence database accessible through EntrezPubMed (see also Kershaw et al (1997) J. Biol. Chem. 272, 15708-15714). It is also called PCLPI and PODXL. For convenience, it will be called PODXL hereafter. PODXL may have the precise sequence given in Accession No. O00592, or it may be a naturally occurring variant thereof. For example, according to O00592, R is a variant for the T at residue 62, and S is a variant of the L at residue 196.

Mature PODXL is a 528 residue glycosylated cell surface polypeptide, of which residues 1-22 are a signal peptide, and residues 23-528 represent the mature protein. Residues 23-431 are believed to be the extracellular portion of the protein and residues 432-452 are the transmembrane region. Residues 23-304 represent a Ser/Thr rich region. It is preferred if the antibody molecule which binds to PODXL binds to the extracellular region of PODXL, for example within the Ser/Thr rich region, or outside of this region.

Podocalyxin-like protein is a member of the sialomucin protein family. PODXL was originally identified as an important component of glomerular podocytes. Podocytes are highly differentiated epithelial cells with interdigitating foot processes covering the outer aspect of the glomerular basement membrane. Other biological activities of PODXL include binding in a membrane protein complex with Na+/H+ exchanger regulatory factor to intracellular cytoskeletal elements, playing a role in hematopoetic cell differentiation, and being expressed in vascular endothelium cells and binding to L-selectin.

PODXL is a heavily glycosylated type-I transmembrane protein belonging to the CD34 family of sialomucins. PODXL was originally described as the major sialoprotein on podocytes of the kidney glomerulus, but was later found to be expressed on vascular endothelial cells and early hematopoietic progenitors. More recently, PODXL has been implicated as an indicator of tumor aggressiveness in breast, liver, and prostate cancers. Human PODXL is located on chromosome 7q32-q33 and encodes for a protein of 528 amino acids. However, because the extracellular domain of PODXL is extensively glycosylated with sialylated O-linked carbohydrates and five potential sites for N-linked glycosylation, the approximate molecular weight of PODXL is 160-165 kDa. PODXL has both putative N-linked and O-linked glycan sites on its sequence.

Functionally, PODXL has been reported to have quite diverse roles depending on the cell type. In podocytes, PODXL acts as an anti-adhesion molecule that maintains the filtration slits open between podocyte foot processes by charge repulsion. However in high endothelial venules, PODXL acts as an adhesion molecule binding to L-selectin and mediating the tethering and rolling of lymphocytes.

In hESC, PODXL was identified transcriptionally to be highly expressed in undifferentiated hESC[5, 6]. By expressed sequence tag frequency analysis, the level of PODXL expression was down-regulated by almost 2.5-fold in 7-8 day embyroid bodies and approximately 7 and 12 fold in neuroectoderm-like cells and hepatocyte-like cells respectively[5]. This result was supported by immunohistochemistry of hESC and 8-day EB where staining was significantly reduced in the latter[7]. In a separate study by Wei et al. comparing the transcriptome profile of hESC and mESC, they observed that the expression of PODXL was not detected by MPSS in mESC line E-14 compared to hESC[8]. At the protein level, Schopperle and DeWolf[9] reported that PODXL underwent post-translational glycosylation changes after the exposure of 2 embryonal carcinoma lines to retinoic acid (reduction in MW from 200 kDa to 170 kDa). The failure of anti-TRA-1-60/81 antibodies to bind to the modified PODXL prompted them to suggest the presence of a Stem Cell PODXL (SC-PODXL) on embryonic stem cells. In ESC, our observations have shown that mAb 84 binding reactivity was reduced in day 8 embyroid bodies compared to undifferentiated hESC. Concomitantly, the decrease or loss in mAb 84-mediated killing on FGF2-starved hESC and day 22 EB respectively can be attributed to the down-regulation of PODXL expression upon differentiation. Furthermore, the simultaneous decrease in mAb 84 and TRA-1-60 binding to hESC during embryoid body formation may implicate the loss of SC-PODXL during differentiation.

In preferred methods of the invention, the PODXL is human PODXL. Human PODXL may have the amino acid sequence of SEQ ID NO: 1 (FIG. 6), or the amino acid sequence of GenBank accession number O00592.2 GI:229462740 (SEQ ID NO: 2; FIG. 7) or of GenBank accession number AAI43319.1 GI:219520307 (SEQ ID NO: 3; FIG. 8). Some embodiments concern PODXL variants such as those disclosed in FIG. 9 (SEQ ID NOs: 8 & 9).

In some embodiments, the PODXL protein comprises one of 60%, 70%, 80%, 85%, 90%, 95%, 96%, 97%, 98%, 99% or 100% sequence identity to the amino acid sequence of SEQ ID NO: 1, SEQ ID NO: 2, SEQ ID NO: 3, SEQ ID NO: 8 or SEQ ID NO: 9. In some embodiments, the PODXL protein comprises one of 60%, 70%, 80%, 85%, 90%, 95%, 96%, 97%, 98%, 99% or 100% sequence identity to the amino acid sequence of SEQ ID NO: 1, SEQ ID NO: 2, SEQ ID NO: 3, SEQ ID NO: 8 or SEQ ID NO: 9, excluding amino acids 1-22.

Preferred PODXL proteins are those capable of being bound by an antibody fragment or antibody molecule selected by the methods described herein, and/or by mAb84 and/or by mAb85.

Antibody Molecules

The present invention is concerned with methods for selecting an antibody molecule as a candidate for having cytotoxic activity against a specified cell type, for example cytotoxic activity against a cell that expresses PODXL and/or cytotoxic activity against an undifferentiated pluripotent stem cell.

Candidate antibody molecules are selected by their ability to bind glycans comprising Fucα1-2Galβ1-3GlcNAc. In some embodiments candidate antibody molecules may bind the fucose residue. In other embodiments candidate antibody molecules may bind the galactose residue. In other embodiments candidate antibody molecules may bind the N-acetyl glucosamine residue. Preferably candidate antibody molecules bind both the fucose and galactose residues. Preferably antibody molecules bind the fucose, galactose and N-acetyl glucosamine residues.

Antibody molecules include binding members or substances having an antibody antigen-binding site. The structure of antibodies and antibody fragments is well known. Generally, an antibody molecule comprises an immunoglobulin heavy chain variable region (VH domain or VH region)

which is paired with a light chain variable region (VL domain or VL region) to provide an antibody antigen binding domain or binding site. Antibody molecules may further comprise antibody constant regions or parts thereof. For example, a VL domain may be attached at its C-terminal end to antibody light chain constant domains including human Cκ or Cλ chains, preferably Cλ chains. Similarly, an antibody molecule based on a VH domain may be attached at its C-terminal end to all or part of an immunoglobulin heavy chain derived from any antibody isotype. Examples of antibody molecules include immunoglobulin isotypes and their isotypic subclasses; antibody fragments, such as Fab, Fab', Fab'-SH, scFv, dsFv, Fv, dAb and Fd; engineered antibody molecules, such as $Fab_2$, $Fab_3$, diabodies, triabodies, tetrabodies and minibodies; and any other polypeptide comprising an antibody antigen-binding site, whether natural or wholly or partially synthetic. Various antibody molecules, fragments and formats have been described, see for example Pluckthun (1997), incorporated herein by reference.

An antibody molecule selected by the method of the present invention, whether in monomeric, dimeric or multimeric form, includes an antibody fragment. An antibody fragment may be, or may be based on, part of a whole antibody. An antibody fragment may not be a whole antibody. Preferably, an antibody fragment is smaller than a whole antibody.

Antibody molecules include chimeric molecules comprising an antigen binding domain, or equivalent, fused to another polypeptide. Cloning and expression of chimeric antibodies are described in EP-A-0120694 and EP-A-0125023.

Antibody molecules include antibody molecules which are monomers—i.e. monomeric antibody molecules—and antibody molecules which include two monomers, which may be referred to as dimeric antibody molecules. Furthermore, antibody molecules may be multimers such as dimers or tetramers. A multimer or a tetramer may, for example, include more than one dimeric antibody molecule. A monomer may comprise an antigen binding domain, or equivalent, e.g. an Fv fragment, fused to a dimerization domain. Preferably, a monomer is monovalent, i.e. it has one antigen binding domain. A dimeric or multimeric (e.g. tetrameric) antibody molecule may comprise a pair of monomers which interact to form a dimer. For example, a dimeric antibody molecule may have two Fv fragments, connected by interacting dimerization domains. Preferably, a dimer is bivalent (or divalent), i.e. it has two antigen binding domains. A multimer may have two or more monomers and thus may have two or more antigen binding domains—i.e. a multimer may be multivalent.

The antibody fragments of a multimeric (e.g. dimeric) antibody molecule may be of identical amino acid sequence, or may have one or more identical complementarity determining region (CDR) amino acid sequences. For example, a dimeric antibody molecule with identical or substantially identical antibody fragments may be referred to as a homodimer or a homodimeric antibody molecule. Alternatively, the fragments in a multimeric antibody molecule may be of different amino acid sequence. For example, they may have different CDR sequences, different framework region sequences, and/or different VH and/or VL region sequences. Preferably, an antibody fragment of the present invention has one or more of the CDR amino acid sequences of mAb84, and/or one or more variants of those CDR amino acid sequences.

Methods of the present invention may be used to select an antibody molecule, including antibody fragments as described above, as a candidate for having cytotoxic activity, in particular cytotoxic activity against a cell which expresses PODXL and/or against an undifferentiated pluripotent stem cell. An example of an antibody which is known to have cytotoxic activity against an undifferentiated pluripotent stem cell is mAb84. The amino acid sequence (and encoding polynucleotide sequence) of the whole mAb84 antibody and the $V_H$ and $V_L$ chains of mAb84 are known, e.g. see WO 2007/102787 which is incorporated herein by reference, and FIGS. 11 and 12 herein.

Preferably, an antibody molecule selected by the methods of the present invention binds PODXL (preferably human PODXL). For example, a monomeric antibody molecule may bind PODXL. Preferably, a dimeric or multimeric antibody molecule binds PODXL. Preferably, the VH and VL regions of an antibody fragment form an antigen binding site which binds PODXL.

An antibody molecule selected by the methods of the present invention will generally be specific for PODXL. In other words, an antibody molecule may bind PODXL with a greater affinity than other mammalian proteins, particularly other human proteins. For example, an antibody molecule may bind PODXL with a similar, or substantially similar affinity to that of mAb84. The kinetics of mAb84 binding to PODXL on the surface of hESCs have been determined as follows: $K_a$ (association rate) is $2.5 \times 10^7$ M; $K_D$ (dissociation rate) is $4 \times 10^{-8}$ M; $k_{off}$ is $2.9 \times 10^{-3}$ s$^{-1}$; $k_{on}$ is 7.1 e4 M$^{-1}$ s$^{-1}$.

The antibodies selected by the present method may be called anti-glycan antibodies or anti-PODXL antibodies.

An antibody molecule selected by the methods of the present invention may show no binding or substantially no binding to other mammalian proteins, and in particular to other proteins which are expressed on the cell surface. For example, an antibody molecule may show no binding or substantially no binding to any or all of the following: stage-specific embryonic antigens (SSEA)-3 and SSEA-4, tumor rejection antigen (Tra)-1-60 and Tra-1-81. Preferably, an antibody molecule selected by the methods of the present invention binds PODXL on the surface of an undifferentiated pluripotent stem cell or cells, such as an undifferentiated hES cell and/or an undifferentiated induced pluripotent stem cell.

Typically, specificity may be determined by means of a binding assay such as ELISA employing a panel of antigens.

Binding of an antibody molecule selected by the methods described herein with PODXL may be abolished by competition with excess recombinant PODXL.

Binding affinity and neutralisation potency of different antibody molecules selected by the methods described herein can be compared under appropriate conditions using routine techniques.

Preferably, an antibody molecule selected by methods of the present invention binds specifically to undifferentiated pluripotent stem cell(s), e.g. the antibody molecule binds PODXL on the surface of undifferentiated pluripotent stem cell(s), such as undifferentiated hES cells and/or undifferentiated induced pluripotent stem cells. An antibody molecule may show no binding or substantially no binding to pluripotent stem cell(s) which have undergone, or are undergoing differentiation. Preferably, an antibody molecule selected by methods of the present invention binds to N-linked and/or O-linked glycans on PODXL.

Sample

Some methods of the present invention involve a sample containing antibody molecules. The sample may be any quantity of antibody molecules which contains, or is suspected of containing, one or more candidate cytotoxic antibody molecules. The sample may contain any combination of antibody molecules herein described.

Stem Cells

The term "stem cell" generally refers to a cell that on division faces two developmental options: the daughter cells can be identical to the original cell (self-renewal) or they may be the progenitors of more specialised cell types (differentiation). The stem cell is therefore capable of adopting one or other pathway (a further pathway exists in which one of each cell type can be formed). Stem cells are therefore cells which are not terminally differentiated and are able to produce cells of other types.

As used in this document the term "stem cell" particularly refers to pluripotent stem cells, particularly mammalian (e.g. human) pluripotent stem cells.

Embryonic Stem Cells

Embryonic Stem (ESCs) cells may be isolated from the inner cell mass (ICM) of the blastocyst, which is the stage of embryonic development when implantation occurs. ESCs may be mammalian ESCs. For example they may be human or non-human, eg mouse or rat ESCs.

ESCs are pluripotent stem cells that have the ability to proliferate indefinitely in vitro in the undifferentiated state. Under the appropriate conditions, ESCs can also be differentiated in vitro and in vivo to cell types representative of all three germ layers (mesoderm, endoderm and ectoderm). Morphologically, the cells have a high nuclear to cytoplasmic ratio and grow as distinct colonies. They also express high levels of alkaline phosphatase, telomerase and the transcription factors Oct-4 and Nanog. Routinely, hESC are characterized by the expression of cell surface markers, including stage-specific embryonic antigens (SSEA)-3 and SSEA-4, tumor rejection antigen (Tra)-1-60 and Tra-1-81. However, these surface antigens are not unique to hESC and have been previously characterized in human embryonal carcinoma (EC) cells.

In the present invention, undifferentiated embryonic stem cells express PODXL on their surface.

Pluripotent Stem Cells

Pluripotent stem cells are true stem cells, with the potential to make any differentiated cell in the body. However, they cannot contribute to making the extraembryonic membranes which are derived from the trophoblast. Several types of pluripotent stem cells have been found.

Multipotent Stem Cells

Multipotent stem cells are true stem cells but can only differentiate into a limited number of types. For example, the bone marrow contains multipotent stem cells that give rise to all the cells of the blood but not to other types of cells. Multipotent stem cells are found in adult animals. It is thought that every organ in the body contains them where they can replace dead or damaged cells.

Methods of characterising stem cells are known in the art, and include the use of standard assay methods such as clonal assay, flow cytometry, long-term culture and molecular biological techniques e.g. PCR, RT-PCR and Southern blotting.

Adult Stem Cells

Adult stem cells comprise a wide variety of types including neuronal, skin and the blood forming stem cells which are the active component in bone marrow transplantation.

These latter stem cell types are also the principal feature of umbilical cord-derived stem cells. Adult stem cells can mature both in the laboratory and in the body into functional, more specialised cell types although the exact number of cell types is limited by the type of stem cell chosen.

Induced Pluripotent Stem Cells

Induced pluripotent stem cells, commonly abbreviated as iPS cells or iPSCs, are a type of pluripotent stem cell artificially derived from a non-pluripotent cell, typically an adult somatic cell, by inserting certain genes. iPS cells are reviewed and discussed in Takahashi, K. & Yamanaka (2006), Yamanaka S, et. al. (2007), Wernig M, et. al. (2007), Maherali N, et. al. (2007), Yu J, et al. (2007) and Takahashi et al., (2007), all of which are incorporated herein by reference.

iPS cells are typically derived by transfection of certain stem cell-associated genes into non-pluripotent cells, such as adult fibroblasts. Transfection is typically achieved through viral vectors, for example through retroviral reprogramming. Transfected genes include the master transcriptional regulators Oct-3/4 (Pouf51) and Sox2, although it is suggested that other genes enhance the efficiency of induction. After 3-4 weeks, small numbers of transfected cells begin to become morphologically and biochemically similar to pluripotent stem cells, and are typically isolated through morphological selection, doubling time, or through a reporter gene and antibiotic infection.

IPSCs may be induced from somatic cells such as fibroblasts by transfection with one or more transcription factors. In some cases, cells are transformed with Oct3/4, Sox2, c-Myc and Klf4. The cells may be additionally transfected with other genes, including transcription factors and/or marker genes. The genes may be introduced using a transposon system such as the Cre/loxP recombination system, or using non-integrating vectors in order to produce iPSCs free of exogenous reprogramming genes. Transfection may be achieved using viral vectors, such as a retrovirus. The virus may be an amphotropic virus. Once the cells have been transfected, they may be grown on feeder cells before transfer to an ESC culture medium.

The IPSCs may be derived from rabbit, guinea pig, rat, mouse or other rodent, cat, dog, pig, sheep, goat, cattle, horse, non-human primate or other non-human vertebrate organism or non-human mammal. In preferred embodiments the IPSCs are derived from human cells.

iPS cells useful in the invention may be derived from any suitable cell type, including lung, foreskin fibroblasts, skin fibroblasts, keratinocytes, blood progenitor cells, bone marrow cells, hepatocytes, gastric epithelial cells, pancreatic cells, neural stem cells, B lymphocytes, ES derived somatic cells and embryonic fibroblasts. The iPS cells may be derived from human, mouse or other mammals. Preferably, the iPS cells are human. In some cases, the cells are not human dermal fibroblasts. The IPSCs may exhibit similar patterns of gene expression and phenotype to ESCs. In the present invention, the undifferentiated IPSCs express PODXL on their surface.

Like ESCs, future therapeutic applications of differentiated induced pluripotent stem cells carry a risk of teratoma formation by contaminating residual undifferentiated IPSC. Despite this problem, currently there are not many strategies developed to separate these cell populations.

Culture of Stem Cells

Any suitable method of culturing stem cells may be used.

Any suitable container may be used to propagate stem cells. Suitable containers include those described in US Patent Publication US2007/0264713 (Terstegge).

Containers may include bioreactors and spinners, for example. A "bioreactor", as the term is used in this document, is a container suitable for the cultivation of eukaryotic cells, for example animal cells or mammalian cells, such as in a large scale. A typical cultivation volume of a regulated bioreactor is between 20 ml and 500 ml.

The bioreactor may comprise a regulated bioreactor, in which one or more conditions may be controlled or monitored, for example, oxygen partial pressure. Devices for measuring and regulating these conditions are known in the art.

For example, oxygen electrodes may be used for oxygen partial pressure. The oxygen partial pressure can be regulated via the amount and the composition of the selected gas mixture (e.g., air or a mixture of air and/or oxygen and/or nitrogen and/or carbon dioxide). Suitable devices for measuring and regulating the oxygen partial pressure are described by Bailey, J E. (Bailey, J E., Biochemical Engineering Fundamentals, second edition, McGraw-Hill, Inc. ISBN 0-07-003212-2 Higher Education, (1986)) or Jackson A T. Jackson A T., Verfahrenstechnik in der Biotechnologie, Springer, ISBN 3540561900 (1993)).

Other suitable containers include spinners. Spinners are regulated or unregulated bioreactors, which can be agitated using various agitator mechanisms, such as glass ball agitators, impeller agitators, and other suitable agitators. The cultivation volume of a spinner is typically between 20 ml and 500 ml. Roller bottles are round cell culture flasks made of plastic or glass having a culture area of between 400 and 2000 $cm^2$. The cells are cultivated along the entire inner surface of these flasks; the cells are coated with culture medium accomplished by a "rolling" motion, i.e. rotating the bottles about their own individual axis.

Alternatively, culture may be static, i.e. where active agitation of the culture/culture media is not employed. By reducing agitation of the culture, aggregates of cells may be allowed to form. Whilst some agitation may be employed to encourage distribution and flow of the culture media over the cultured cells this may be applied so as not to substantially disrupt aggregate formation. For example, a low rpm agitation, e.g. less than 30 rpm or less than 20 rpm, may be employed.

Propagation with Passage

The methods and compositions described here may comprise passaging, or splitting during culture. The methods may involve continuous or continual passage.

By "continual" or "continuous", we mean that our methods enable growth of stem cells in a fashion that enables them to be passaged, e.g., taken off the plates or microcarriers on which they are growing and transferred to other plates, microcarriers or particles, and that this process may be repeated at least once, for example twice, three times, four times, five times, etc. In some cases, this may be repeated any number of times, for example indefinitely or infinitely.

Cells in culture may be dissociated from the substrate or flask, and "split", subcultured or passaged, by dilution into tissue culture medium and replating.

Cells growing on particles may be passaged back onto particle culture. Alternatively, they may be passaged back onto conventional (2D) cultures. Tissue culture cells growing on plates may be passaged onto particle culture.

The term "passage" may generally refer to the process of taking an aliquot of a cell culture, dissociating the cells completely or partially, diluting and inoculating into medium.

The passaging may be repeated one or more times. The aliquot may comprise the whole or a portion of the cell culture. The cells of the aliquot may be completely, partially or not confluent. The passaging may comprise at least some of the following sequence of steps: aspiration, rinsing, trypsinization, incubation, dislodging, quenching, re-seeding and aliquoting. The protocol published by the Hedrick Lab, UC San Diego may be used (http://hedricklab.ucsd.edu/Protocol/COSCell.html).

The cells may be dissociated by any suitable means, such as mechanical or enzymatic means known in the art. The cells may be broken up by mechanical dissociation, for example using a cell scraper or pipette. The cells may be dissociated by sieving through a suitable sieve size, such as through 100 micron or 500 micron sieves. The cells may be split by enzymatic dissociation, for example by treatment with collagenase or trypLE harvested. The dissociation may be complete or partial.

The dilution may be of any suitable dilution. The cells in the cell culture may be split at any suitable ratio. For example, the cells may be split at a ratio of 1:2 or more, 1:3 or more, 1:4 or more or 1:5 or more. Thus, stem cells may be passaged for 1 passage or more. For example, stem cells may be passaged for 2, 3, 4, 5, 6, 7, 8, 9, 10, 11, 12, 13, 14, 15, 16, 17, 18, 19, 20, 21, 22, 23, 24, 25 passages or more. Passages may be expressed as generations of cell growth. Stem cells may be propagated for 1, 2, 3, 4, 5, 6, 7, 8, 9, 10, 11, 12, 13, 14, 15, 16, 17, 18, 19, 20, 21, 22, 23, 24, 25 generations or more. Passages may also be expressed as the number of cell doublings. Stem cells may be propagated for 1, 2, 3, 4, 5, 6, 7, 8, 9, 10, 11, 12, 13, 14, 15, 16, 17, 18, 19, 20, 21, 22, 23, 24, 25 cell doublings or more.

Maintenance of Stem Cell Characteristics

The propagated stem cells may retain at least one characteristic of a mammalian (e.g. a primate or human) stem cell. The stem cells may retain the characteristic after one or more passages. They may do so after a plurality of passages. They may do so after the stated number of passages as described above.

The characteristic may comprise a morphological characteristic, immunohistochemical characteristic, a molecular biological characteristic, etc. The characteristic may comprise a biological activity.

Stem Cell Characteristics

The stem cells may display any of the following stem cell characteristics.

Stem cells may display increased expression of Oct4 and/or SSEA-1 and/or TRA-1-60. Stem cells which are self-renewing may display a shortened cell cycle compared to stem cells which are not self-renewing.

Stem cells may display defined morphology. For example, in the two dimensions of a standard microscopic image, human embryonic stem cells display high nuclear/cytoplasmic ratios in the plane of the image, prominent nucleoli, and compact colony formation with poorly discernable cell junctions.

Stem cells may also be characterized by expressed cell markers as described in further detail below.

Expression of Pluripotency Markers

The biological activity that is retained may comprise expression of one or more pluripotency markers.

Stage-specific embryonic antigens (SSEA) are characteristic of certain embryonic cell types. Antibodies for SSEA markers are available from the Developmental Studies Hybridoma Bank (Bethesda Md.). Other useful markers are detectable using antibodies designated Tra-1-60 and Tra-1-81 (Andrews et al., Cell Lines from Human Germ Cell Tumors, in E. J. Robertson, 1987, supra). Human embryonic stem cells are typically SSEA-1 negative and SSEA-4 positive. hEG cells are typically SSEA-1 positive. Differentiation of primate pluripotent stem cells (pPS) cells in vitro results in the loss of SSEA-4, Tra-1-60, and Tra-1-81 expression and increased expression of SSEA-1. pPS cells can also be characterized by the presence of alkaline phosphatase activity, which can be detected by fixing the cells with 4% paraformaldehyde, and then developing with Vector Red as a substrate, as described by the manufacturer (Vector Laboratories, Burlingame Calif.).

Embryonic stem cells are also typically telomerase positive and OCT-4 positive. Telomerase activity can be determined using TRAP activity assay (Kim et al., Science 266:2011, 1997), using a commercially available kit (TRAPeze® XK Telomerase Detection Kit, Cat. s7707; Intergen Co., Purchase N.Y.; or TeloTAGGG™ Telomerase PCR ELISA plus, Cat. 2,013,89; Roche Diagnostics, Indianapolis). hTERT expression can also be evaluated at the mRNA level by RT-PCR. The LightCycler TeloTAGGG™ hTERT quantification kit (Cat. 3,012,344; Roche Diagnostics) is available commercially for research purposes.

Any one or more of these pluripotency markers, including FOXD3, PODXL, alkaline phosphatase, OCT-4, SSEA-4, TRA-1-60 and Mab84, etc, may be retained by the propagated stem cells.

Detection of markers may be achieved through any means known in the art, for example immunologically. Histochemical staining, flow cytometry (FACS), Western Blot, enzyme-linked immunoassay (ELISA), etc may be used.

Flow immunocytochemistry may be used to detect cell-surface markers. immunohistochemistry (for example, of fixed cells or tissue sections) may be used for intracellular or cell-surface markers. Western blot analysis may be conducted on cellular extracts. Enzyme-linked immunoassay may be used for cellular extracts or products secreted into the medium.

For this purpose, antibodies to the pluripotency markers as available from commercial sources may be used.

Antibodies for the identification of stem cell markers including the Stage-Specific Embryonic Antigens 1 and 4 (SSEA-1 and SSEA-4) and Tumor Rejection Antigen 1-60 and 1-81 (TRA-1-60, TRA-1-81) may be obtained commercially, for example from Chemicon International, Inc (Temecula, Calif., USA). The immunological detection of these antigens using monoclonal antibodies has been widely used to characterize pluripotent stem cells (Shamblott M. J. et. al. (1998) PNAS 95: 13726-13731; Schuldiner M. et. al. (2000). PNAS 97: 11307-11312; Thomson J. A. et. al. (1998). Science 282: 1145-1147; Reubinoff B. E. et. al. (2000). Nature Biotechnology 18: 399-404; Henderson J. K. et. al. (2002). Stem Cells 20: 329-337; Pera M. et. al. (2000). J. Cell Science 113: 5-10.).

The expression of tissue-specific gene products can also be detected at the mRNA level by Northern blot analysis, dot-blot hybridization analysis, or by reverse transcriptase initiated polymerase chain reaction (RT-PCR) using sequence-specific primers in standard amplification methods. Sequence data for the particular markers listed in this disclosure can be obtained from public databases such as GenBank (URL www.ncbi.nlm.nih.qov:80/entrez). See U.S. Pat. No. 5,843,780 for further details.

Substantially all of the propagated cells, or a substantial portion of them, may express the marker(s). For example, the percentage of cells that express the marker or markers may be 50% or more, 60% or more, 70% or more, 80% or more, 90% or more, 93% or more, 95% or more, 97% or more, 98% or more, 99% or more, or substantially 100%.

Cell Viability

The biological activity may comprise cell viability after the stated number of passages. Cell viability may be assayed in various ways, for example by Trypan Blue exclusion.

A protocol for vital staining follows. Place a suitable volume of a cell suspension (20-200 µL) in appropriate tube add an equal volume of 0.4% Trypan blue and gently mix, let stand for 5 minutes at room temperature. Place 10 µl of stained cells in a hemocytometer and count the number of viable (unstained) and dead (stained) cells. Calculate the average number of unstained cells in each quadrant, and multiply by $2\times10^4$ to find cells/ml. The percentage of viable cells is the number of viable cells divided by the number of dead and viable cells.

The viability of cells may be 50% or more, 60% or more, 70% or more, 80% or more, 90% or more, 93% or more, 95% or more, 97% or more, 98% or more, 99% or more, or substantially 100%.

Karyotype

The propagated stem cells may retain a normal karyotype during or after propagation. A "normal" karyotype is a karyotype that is identical, similar or substantially similar to a karyotype of a parent stem cell from which the stem cell is derived, or one which varies from it but not in any substantial manner. For example, there should not be any gross anomalies such as translocations, loss of chromosomes, deletions, etc.

Karyotype may be assessed by a number of methods, for example visually under optical microscopy. Karyotypes may be prepared and analyzed as described in McWhir et al. (2006), Hewitt et al. (2007), and Gallimore and Richardson (1973). Cells may also be karyotyped using a standard G-banding technique (available at many clinical diagnostics labs that provide routine karyotyping services, such as the Cytogenetics Lab at Oakland Calif.) and compared to published stem cell karyotypes.

All or a substantial portion of propagated cells may retain a normal karyotype. This proportion may be 50% or more, 60% or more, 70% or more, 80% or more, 90% or more, 93% or more, 95% or more, 97% or more, 98% or more, 99% or more, or substantially 100%.

Pluripotency

The propagated stem cells may retain the capacity to differentiate into all three cellular lineages, i.e., endoderm, ectoderm and mesoderm. Methods of induction of stem cells to differentiate each of these lineages are known in the art and may be used to assay the capability of the propagated stem cells. All or a substantial portion of propagated cells may retain this ability. This may be 50% or more, 60% or more, 70% or more, 80% or more, 90% or more, 93% or more, 95% or more, 97% or more, 98% or more, 99% or more, or substantially 100% of the propagated stem cells.

The pluripotency of the generated stem cells may be determined by use of suitable assays. Such assays may comprise detecting one or more markers of pluripotency, e.g. SSEA-1 antigen, alkaline phosphatase activity, detection of Oct-4 gene and/or protein expression, by observing the extent of teratoma formation in SCID mice or formation of embryoid bodies. Pluripotency of hESC may be defined by the expression of one or more markers such as Oct-4, SSEA-4, Tra-1-60, Tra-1-81, SOX-2 and GCTM-2.

Co-Culture and Feeders

Methods may comprise culturing stem cells in the presence or absence of co-culture. The term "co-culture" refers to a mixture of two or more different kinds of cells that are grown together, for example, stromal feeder cells. The two or more different kinds of cells may be grown on the same surfaces, such as particles or cell container surfaces, or on different surfaces. The different kinds of cells may be grown on different particles.

Feeder cells, as the term is used in this document, may mean cells which are used for or required for cultivation of cells of a different type. In the context of stem cell culture, feeder cells have the function of securing the survival, proliferation, and maintenance of cell pluripotency. Cell pluripotency may be achieved by directly co-cultivating the feeder cells. Alternatively, or in addition, the feeder cells may be cultured in a medium to condition it. The conditioned medium may be used to culture the stem cells.

The inner surface of the container such as a culture dish may be coated with a feeder layer of mouse embryonic skin cells that have been treated so they will not divide. The feeder cells release nutrients into the culture medium which are required for ES cell growth. The stem cells growing on particles may therefore be grown in such coated containers.

Arrangements in which feeder cells are absent or not required are also possible. For example, the cells may be grown in medium conditioned by feeder cells or stem cells.

Media and Feeder Cells

Media for isolating and propagating pluripotent stem cells can have any of several different formulas, as long as the cells obtained have the desired characteristics, and can be propagated further.

Suitable sources are as follows: Dulbecco's modified Eagles medium (DMEM), Gibco#11965-092; Knockout Dulbecco's modified Eagles medium (KO DMEM), Gibco#10829-018; 200 mM L-glutamine, Gibco#15039-027; non-essential amino acid solution, Gibco 11140-050; beta-mercaptoethanol, Sigma#M7522; human recombinant basic fibroblast growth factor (bFGF), Gibco#13256-029. Exemplary serum-containing embryonic stem (ES) medium is made with 80% DMEM (typically KO DMEM), 20% defined fetal bovine serum (FBS) not heat inactivated, 0.1 mM non-essential amino acids, 1 mM L-glutamine, and 0.1 mM beta-mercaptoethanol. The medium is filtered and stored at 4 degrees C. for no longer than 2 weeks. Serum-free embryonic stem (ES) medium is made with 80% KO DMEM, 20% serum replacement, 0.1 mM non-essential amino acids, 1 mM L-glutamine, and 0.1 mM beta-mercaptoethanol. An effective serum replacement is Gibco#10828-028. The medium is filtered and stored at 4 degrees C. for no longer than 2 weeks. Just before use, human bFGF is added to a final concentration of 4 ng/mL (Bodnar et al., Geron Corp, International Patent Publication WO 99/20741).

The media may comprise Knockout DMEM media (Invitrogen-Gibco, Grand Island, N.Y.), supplemented with 10% serum replacement media (Invitrogen-Gibco, Grand Island, N.Y.), 5 ng/ml FGF2 (Invitrogen-Gibco, Grand Island, N.Y.) and 5 ng/ml PDGF AB (Peprotech, Rocky Hill, N.J.).

Feeder cells (where used) may be propagated in mEF medium, containing 90% DMEM (Gibco#11965-092), 10% FBS (Hyclone#30071-03), and 2 mM glutamine. mEFs are propagated in T150 flasks (Coming#430825), splitting the cells 1:2 every other day with trypsin, keeping the cells subconfluent. To prepare the feeder cell layer, cells are irradiated at a dose to inhibit proliferation but permit synthesis of important factors that support human embryonic stem cells (about 4000 rads gamma irradiation). Six-well culture plates (such as Falcon#304) are coated by incubation at 37 degrees C. with 1 mL 0.5% gelatin per well overnight, and plated with 375, 000 irradiated mEFs per well. Feeder cell layers are typically used 5 h to 4 days after plating.

Conditions for culturing other stem cells are known, and can be optimized appropriately according to the cell type. Media and culture techniques for particular cell types referred to in the previous section are provided in the references cited.

Serum Free Media

The methods and compositions described here may include culture of stem cells in a serum-free medium.

The term "serum-free media" may comprise cell culture media which is free of serum proteins, e.g. fetal calf serum. Serum-free media are known in the art, and are described for example in U.S. Pat. Nos. 5,631,159 and 5,661,034. Serum-free media are commercially available from, for example, Gibco-BRL (Invitrogen).

The serum-free media may be protein free, in that it may lack proteins, hydrolysates, and components of unknown composition. The serum-free media may comprise chemically-defined media in which all components have a known chemical structure. Chemically-defined serum-free media is advantageous as it provides a completely defined system which eliminates variability and allows for improved reproducibility and more consistent performance, and decreases possibility of contamination by adventitious agents.

The serum-free media may comprise Knockout DMEM media (Invitrogen-Gibco, Grand Island, N.Y.).

The serum-free media may be supplemented with one or more components, such as serum replacement media, at a concentration of for example, 5%, 10%, 15%, etc. The serum-free media may be supplemented with 10% serum replacement media from Invitrogen-Gibco (Grand Island, N.Y.).

The serum-free medium in which the dissociated or disaggregated embryonic stem cells are cultured may comprise one or more growth factors. A number of growth factors are known in the art, including FGF2, IGF-2, Noggin, Activin A, TGF beta 1, HRG1 beta, LIF, S1P, PDGF, BAFF, April, SCF, Flt-3 ligand, Wnt3A and others. The growth factor(s) may be used at any suitable concentration such as between 1 pg/ml to 500 ng/ml.

Media Supplements

Culture media may be supplemented with one or more additives. For example, these may be selected from one or more of: a lipid mixture, Bovine Serum Albumin (e.g. 0.1% BSA), hydrolysate of soybean protein.

Sources of Induced Pluripotent Stem Cells

Several methods have now been provided for the isolation of pluripotent stem cells that do not lead to the destruction of an embryo, e.g. by transforming (inducing) adult somatic cells or germ cells. These methods include:

1. Reprogramming by nuclear transfer. This technique involves the transfer of a nucleus from a somatic cell into an oocyte or zygote. In some situations this may lead to the creation of an animal-human hybrid cell. For example, cells may be created by the fusion of a human somatic cell with an animal oocyte or zygote or fusion of a human oocyte or zygote with an animal somatic cell.
2. Reprogramming by fusion with embryonic stem cells. This technique involves the fusion of a somatic cell with an embryonic stem cell. This technique may also lead to the creation of animal-human hybrid cells, as in 1 above.
3. Spontaneous re-programming by culture. This technique involves the generation of pluripotent cells from non-pluripotent cells after long term culture. For example, pluripotent embryonic germ (EG) cells have been generated by long-term culture of primordial germ cells (PGC) (Matsui et al., Derivation of pluripotential embryonic stem cells from murine primordial germ cells in culture. Cell 70, 841-847, 1992, incorporated herein by reference). The development of pluripotent stem cells after prolonged culture of bone marrow-derived cells has also been reported (Jiang et al., Pluripotency of mesenchymal stem cells derived from adult marrow. Nature 418, 41-49, 2002, incorporated herein by reference). They designated these cells multipotent adult progenitor cells (MAPCs). Shinohara et al also demonstrated that pluripotent stem cells can be generated during the course of culture of germline stem (GS) cells from neonate mouse testes, which they designated multipotent germline stem (mGS) cells (Kanatsu- Shinohara et al., Generation of pluripotent stem cells from neonatal mouse testis. Cell 119, 1001-1012, 2004).

4. Reprogramming by defined factors. For example the generation of iPS cells by the retrovirus-mediated introduction of transcription factors (such as Oct-3/4, Sox2, c-Myc, and KLF4) into mouse embryonic or adult fibroblasts, e.g. as described above. Kaji et al (Virus-free induction of pluripotency and subsequent excision of reprogramming factors. Nature. Online publication 1 Mar. 2009) also describe the non-viral transfection of a single multiprotein expression vector, which comprises the coding sequences of c-Myc, Klf4, Oct4 and Sox2 linked with 2A peptides, that can reprogram both mouse and human fibroblasts. iPS cells produced with this non-viral vector show robust expression of pluripotency markers, indicating a reprogrammed state confirmed functionally by in vitro differentiation assays and formation of adult chimaeric mice. They succeeded in establishing reprogrammed human cell lines from embryonic fibroblasts with robust expression of pluripotency markers.

Methods 1-4 are described and discussed by Shinya Yamanaka in Strategies and New Developments in the Generation of Patient-Specific Pluripotent Stem Cells (Cell Stem Cell 1, July 2007 ª2007 Elsevier Inc), incorporated herein by reference.

5. Derivation of hESC lines from single blastomeres or biopsied blastomeres. See Klimanskaya I, Chung Y, Becker S, Lu S J, Lanza R. Human embryonic stem cell lines derived from single blastomeres. Nature 2006; 444:512, Lei et al Xeno-free derivation and culture of human embryonic stem cells: current status, problems and challenges. Cell Research (2007) 17:682-688, Chung Y, Klimanskaya I, Becker S, et al. Embryonic and extraembryonic stem cell lines derived from single mouse blastomeres. Nature. 2006; 439:216-219. Klimanskaya I, Chung Y, Becker S, et al. Human embryonic stem cell lines derived from single blastomeres. Nature. 2006; 444:481-485. Chung Y, Klimanskaya I, Becker S, et al. Human embryonic stem cell lines generated without embryo destruction. Cell Stem Cell. 2008; 2:113-117 and Dusko Ilic et al (Derivation of human embryonic stem cell lines from biopsied blastomeres on human feeders with a minimal exposure to xenomaterials. Stem Cells And Development), all incorporated herein by reference.

6. hESC lines obtained from arrested embryos which stopped cleavage and failed to develop to morula and blastocysts in vitro. See Zhang X, Stojkovic P, Przyborski S, et al. Derivation of human embryonic stem cells from developing and arrested embryos. Stem Cells 2006; 24:2669-2676 and Lei et al Xeno-free derivation and culture of human embryonic stem cells: current status, problems and challenges. Cell Research (2007) 17:682-688, both incorporated herein by reference.

7. Parthogenesis (or Parthenogenesis). This technique involves chemical or electrical stimulation of an unfertilised egg so as to cause it to develop into a blastomere from which embryonic stem cells may be derived. For example, see Lin et al. Multilineage potential of homozygous stem cells derived from metaphase II oocytes. Stem Cells. 2003; 21(2):152-61 who employed the chemical activation of nonfertilized metaphase II oocytes to produce stem cells.

8. Stem cells of fetal origin. These cells lie between embryonic and adult stem cells in terms of potentiality and may be used to derive pluripotent or multipotent cells. Human umbilical-cord-derived fetal mesenchymal stem cells (UC fMSCs) expressing markers of pluripotency (including Nanog, Oct-4, Sox-2, Rex-1, SSEA-3, SSEA-4, Tra-1-60, and Tra-1-81, minimal evidence of senescence as shown by P-galactosidase staining, and the consistent expression of telomerase activity) have been successfully derived by Chris H. Jo et al (Fetal mesenchymal stem cells derived from human umbilical cord sustain primitive characteristics during extensive expansion. Cell Tissue Res (2008) 334:423-433, incorporated herein by reference). Winston Costa Pereira et al (Reproducible methodology for the isolation of mesenchymal stem cells from human umbilical cord and its potential for cardiomyocyte generation J Tissue Eng Regen Med 2008; 2: 394-399, incorporated herein by reference) isolated a pure population of mesenchymal stem cells from Wharton's jelly of the human umbilical cord. Mesenchymal stem cells derived from Wharton's jelly are also reviewed in Troyer & Weiss (Concise Review: Wharton's Jelly-Derived Cells Are a primitive Stromal Cell Population. Stem Cells 2008:26:591-599). Kim et al (Ex vivo characteristics of human amniotic membrane-derived stem cells. Cloning Stem Cells 2007 Winter; 9(4): 581-94, incorporated herein by reference) succeeded in isolating human amniotic membrane-derived mesenchymal cells from human amniotic membranes. Umbilical cord is a tissue that is normally discarded and stem cells derived from this tissue have tended not to attract moral or ethical objection.

Induced pluripotent stem cells have the advantage that they can be obtained by a method that does not cause the destruction of an embryo, more particularly by a method that does not cause the destruction of a human or mammalian embryo. As such, aspects of the invention may be performed or put into practice by using cells that have not been prepared exclusively by a method which necessarily involves the destruction of human or animal embryos from which those cells may be derived. This optional limitation is specifically intended to take account of Decision G0002/06 of 25 Nov. 2008 of the Enlarged Board of Appeal of the European Patent Office.

Differentiation of Undifferentiated Cells

Pluripotent stem cells may be induced to differentiate into a variety of different cell types.

For example, the pluripotent stem cells may be induced to differentiate into cardiac cells (cardiomyocytes), hepatocytes, neural cells, cartilage (chondrocytes), muscle, fat (adipocytes), bone (osteocytes) or other cells. The pluripotent stem cells may be induced to form tissues such as epithelial tissues, mesoderm, endoderm, ectoderm or epidermis.

Methods of differentiating stem cells are known in the art and are described in for example Itskovitz-Eldor (2000) and Graichen et al (2007) and may be used with IPSCs. The cultured stem cells may also be used for the formation of embryoid bodies.

Embryoid bodies, and methods for making them, are known in the art. The term "embryoid body" refers to spheroid colonies seen in culture which may be produced by the growth of embryonic stem cells in suspension. Embryoid bodies are of mixed cell types, and the distribution and timing of the appearance of specific cell types corresponds to that observed within the embryo. Embryoid bodies may be generated by plating out embryonic stem cells onto media such as semi-solid media. Methylcellulose media may be used as described in Lim et al, Blood. 1997; 90:1291-1299.

Embryonic stem cells may be induced to form embryoid bodies, for example using the methods described in Itskovitz-Eldor (2000). The embryoid bodies contain cells of all three embryonic germ layers (endoderm, ectoderm, mesoderm).

The embryoid bodies may be further induced to differentiate into different lineages for example by exposure to the appropriate induction factor or an environmental change.

Graichen et al (2007) describes the formation of cardiomyocytes from human embryonic stem cells by manipulation of the p38MAP kinase pathway. Graichen demonstrates induction of cardiomyocyte formation from stem cells by exposure to a specific inhibitor of p38 MAP kinase such as SB203580 at less than 10 μm.

Differentiated cells may be employed for any suitable purpose, such as regenerative therapy and cell transplantation as known in the art.

Glycans

The present inventors have developed methods of selecting candidate antibody molecules based on their ability to bind glycans comprising Fucα1-2Galβ1-3GlcNAc. The abbreviated terminology used to describe these glycans is commonly understood in the art. Thus such glycans comprise fucose (Fuc), galactose (Gal) and N-acetylglucosamine residues (GlcNAc).

The IUPAC name for fucose is (3S,4R,5S,6S)-6-Methyltetrahydro-2H-pyran-2,3,4,5-tetraol. The molecular formula of fucose is $C_6H_{12}O_5$. The chemical structure of fucose is given in FIG. 10A.

The IUPAC name for galactose is (2S,3R,4S,5S,6R)-6-methyloltetrahydropyran-2,3,4,5-tetrol. The molecular formula of galactose is $C_6H_{12}O_5$. The chemical structure of galactose is given in FIG. 10B.

The IUPAC name for N-acetylglucosamine is 2-(Acetylamino)-2-deoxy-D-glucose. The molecular formula for N-acetylglucosamine is $C_8H_{15}NO_6$. The chemical structure of N-acetylglucosamine is given in FIG. 10C.

In addition, the present inventors have developed ways of using glycans comprising Fucα1-2Galβ1-3GlcNAc to select in vitro an antibody molecule that binds PODXL and/or is cytotoxic. Furthermore, the present inventors have developed ways of using glycans comprising Fucα1-2Galβ1-3GlcNAc to determine in vitro whether an antibody molecule that is known to bind PODXL is cytotoxic.

The structure and biosynthesis of glycans is well known in the art, see for example Essentials of Glycobiology[31]. Glycans consist of chains of monosaccharide residues which have become covalently linked by glycosylation. As such they are polysaccharises or oligosaccharides and carbohydrates. Glycosylation is the enzymatic process that links saccharides to produce glycans. These glycans may be attached to proteins, as in glycoproteins and proteoglycans, or to other organic molecules such as lipids. In particular, one example of a glycosylated protein is PODXL.

Glycans may consist of O-glycosidic linkages of monosaccharide residues (also known as O-linked glycans) or N-glycosidic linkages of monosaccharide residues (also known as N-linked glycans). The process of N-linked and O-linked glycosylation has been well studied in the art, see Protein Structure and Function[33].

Briefly, almost all secreted and membrane-associated proteins of eukaryotic cells are glycosylated, with oligosaccharides attached to the polypeptide chain at one or more positions by either N- or O-glycosidic bonds. N-linked and O-linked glycans are categorized by their method of glycan attachment. For N-linked glycans, the core in most eukaryotes is the same, and derives from a larger preformed precursor, Glc3Man3GlcNAc2. As the protein is being synthesized in the endoplasmic reticulum (ER), the precursor is transferred to asparagine residues in the N-glycosylation sequence NXS[33]. To produce the mature oligosaccharides, the N-glycosylation core is first trimmed in the ER and additional processing can then occur in the Golgi apparatus giving rise to diverse complex sugars[33]. In contrast, O-linked glycans can have several different core structures, usually attached through N-acetylgalactosamine to the side chain of serine or threonine residues; these are extended by the addition of monosaccharide residues[33].

In preferred aspects, the glycans used in methods of the present invention may be N-linked glycans. In other aspects, the glycans used in methods of the present invention may be O-linked glycans.

PODXL has both putative N-linked and O-linked glycan sites on its sequence.

Glycans are generally found on the exterior surface of cells and have many protective, stabilizing, organizational, and barrier functions. For example, glycans attached to matrix molecules, such as proteoglycans, are important for the maintenance of tissue structure, porosity, and integrity.

Glycans used in methods of the present invention are heteropolymers. As is commonly understood in the art, a heteropolymer is formed from two or more residues that are different from one another.

In preferred aspects glycans used in methods of the present invention are heteropolymers comprising fucose (Fuc), galactose (Gal) and N-acetyl glucosamine residues (GlcNAc). In more preferred embodiments the glycan comprises Fucα1-2Galβ1-3GlcNAc.

In some aspects the glycan comprises Fucα1-2Galβ1-3GlcNAc. In preferred aspects the glycan may comprise or consist of one or more of:

Fucα1-2Galβ1-3GlcNAcβ1-3Galβ1-4Glcβ;
Neu5Acα2-6Galβ1-4GlcNAcβ1-6(Fucα1-2Galβ1-3GlcNAcβ1-3)Galβ-4Glc;
Fucα1-2Galβ1-3GlcNAcβ;
Fucα1-2Galβ1-3GlcNAcβ1-3Galβ-4Glcβ;
Fucα1-2Galβ1-3GlcNAcβ1-3GalNAc;
Fucα1-2Galβ1-3GlcNAcβ1-3(Galβ1-4GlcNAcβ1-6) Galβ1-4Glc;
Fucα1-2Galβ1-3GlcNAβ1-3(Galβ1-4(Fucα1-3) GlcNAcβ1-6)Galβ1-4Glc;
Fucα1-2Galβ1-3GlcNAcβ; or
Fucα1-2Galβ1-3GlcNAcβ1-2Manα1-3(Fucα1-2Galβ1-3GlcNAcβ1-2Manα1-6)Manβ1-4GlcNAcβ1-4GlcNAcβ;

In some embodiments glycans of the present invention may also comprise a spacer molecule. Preferred spacer molecules are listed in Table 1.

In some preferred embodiments the glycan may comprise or consist of one or more of:

Fucα1-2Galβ1-3GlcNAcβ1-3Galβ1-4Glcβ-Sp8;
Neu5Acα2-6Galβ1-4GlcNAcβ1-6(Fucα1-2Galβ1-3GlcNAcβ1-3)Galβ-4Glc-Sp21;
Fucα1-2Galβ1-3GlcNAcβ-Sp0;
Fucα1-2Galβ1-3GlcNAcβ1-3Galβ1-4Glcβ-Sp10;
Fucα1-2Galβ1-3GlcNAcβ1-3GalNAc-Sp14;
Fucα1-2Galβ1-3GlcNAcβ1-3(Galβ1-4GlcNAcβ1-6) Galβ1-4Glc-Sp21;
Fucα1-2Galβ1-3GlcNAcβ1-3(Galβ1-4(Fucα1-3) GlcNAβ1-6)Galβ1-4Glc-Sp21;
Fucα1-2Galβ1-3GlcNAcβ-Sp8; or
Fucα1-2Galβ1-3GlcNAcβ1-2Manα1-3(Fucα1-2Galβ1-3GlcNAcβ1-2Manα1-6)Manβ1-4GlcNAcβ-Sp20;

Where SpX denotes a spacer molecule as described in Table 1.

Optionally, the glycan is not a glycosaminoglycan (GAG), e.g. heparin, heparan sulphate (HS), dermatin, keratin, chondroitin or their sulphates.

Glycan Length

Glycans used in methods of the present invention comprise linear or branched chains of at least three monosaccharide residues. In some embodiments linear or branched glycans may comprise at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty one, at least twenty two, at least twenty three, at least twenty four, at least twenty five, at least twenty six, at least twenty seven, at least twenty eight, at least twenty nine or at least thirty residues. In some embodiments glycans may contain up to thirty five, forty, forty five, fifty, fifty five, sixty, sixty five or more than sixty five monosaccharide residues.

In some embodiments the glycan chains contain less than sixty residues. Alternatively the glycan chains contain less than fifty; forty five; forty; thirty five; thirty; twenty five; twenty; fifteen; ten or five residues.

Linear and Branched Glycans.

Glycans used in methods of the present invention may have a linear or a branched structure.

In a linear glycan, each residue in the glycan chain is linked to not more than two other residues. An example of a linear glycan is shown in FIG. 2. Branched glycans differ from linear glycans in that one or more residues in the glycan chain are linked to three or more other residues. An example of a branched glycan is shown in FIG. 1.

Free Ends

Glycans used in methods of the present invention may have one or more 'free' ends.

When one or more glycans are immobilised on a solid support (see below), or attached to a polypeptide, then the free ends are those which are not attached to the solid support or polypeptide. As it is not attached to the solid support, the free end of a glycan can be bound by candidate antibody molecules. In some embodiments the free end may contain the glycan residue or residues which are bound by candidate antibodies.

In glycans comprising Fucα1-2Galβ1-3GlcNAc, the free end may be that closest to the fucose residue.

The terminal saccharide residue at the free end(s) is known as a free end terminal. A terminal saccharide residue is only bound to one other residue in the glycan. Preferably the free end terminal is a fucose residue. Most preferably the free end terminal is a fucose residue attached to a galactose residue which is attached to an N-acetyl glucosamine residue in the following order: fucose (terminal)-galactose-N-acetyl glucosamine. The N-acetyl glucosamine residue is attached to the remainder of the glycan. In some embodiments candidate antibodies bind to the free end terminal.

Linear glycans may have one or two free ends. Branched glycans may have one, two or more than two free ends. Preferably branched glycans have two free ends. In some embodiments the two or more free ends of a branched glycan are identical in structure, i.e they contain the same saccharide residues arranged in the same order. Preferably the free ends of a branched glycan are identical. Most preferably each of the identical free ends has a fucose residue as the free end terminal. Most preferably each of the identical free ends has a terminal fucose residue attached to a galactose residue and an N-acetyl glucosamine residue in the following order: fucose (terminal)-galactose-N-acetyl glucosamine.

In other embodiments the one or more free ends of a branched glycan are not identical in structure, i.e. each free end contains different saccharide residues or the same or substantially the same saccharide residues but arranged in a different order. Preferably at least one of the free ends has a fucose residue as the terminal saccharide. Preferably at least one of the free ends has a free end terminal fucose residue attached to a galactose residue and an N-acetyl glucosamine residue in the following order: fucose (terminal)-galactose-N-acetyl glucosamine.

The branches in a branched glycan may be the same length (i.e. they may contain the same number of glycan residues in the branch), or they may be different lengths.

Linker Ends

The distal end from the free end is known as the linker end. When glycans are attached to proteins the linker end is the end which is attached (e.g. covalently bonded) to the protein. When one or more glycans are immobilised on a solid support, e.g in a glycan array, then the linker end is the end which is attached (e.g. covalently bonded) to the solid support. The linker end may be attached (e.g. covalently bonded) to a spacer molecule which is attached to the solid support. In glycans comprising Fucα1-2Galβ1-3GlcNAc, the linker end is preferably the end which is distal to the fucose residue.

Preferably both linear and branched glycans have a single linker end. In some embodiments, branched glycans have two or more free ends and one linker end. Preferably, branched glycans have two free ends and one linker end The terminal saccharide at the linker end is the linker end terminal.

Solid Support

In some embodiments the glycans used in the methods of the present invention may be immobilised, i.e. held or attached, onto a solid support. The solid support can be any suitable material to which glycans can be attached. Examples of preferred solid supports include glass slides, multiwell plates or silicon thin-film cells. Solid supports may be coated with an appropriate material (e.g a matrix) to make them suitable for binding by glycans and/or by spacer molecules. Conveniently the solid support comprises any suitable matrix such as agarose, acrylamide, Sepharose™ or Sephadex™. The solid support may be a solid substrate such as a microtitre plate or chip, or a column. Alternatively the solid support may be formed from a material which can be bound by glycans and/or spacer molecules.

Glycans may be immobilised on the solid support by binding between the glycan and the solid support. Glycans may be immobilised by attaching the glycan to the solid support directly or indirectly.

Immobilisation is indirect when the glycan is attached to the solid support via a spacer molecule (spacer molecules are discussed below). In preferred embodiments the spacer molecule is attached to the glycan at the linker end. In more preferred embodiments the spacer molecule is also attached to the solid support. In more preferred embodiments the spacer molecule is attached to the linker end of the glycan at a first end of the spacer molecule and attached to the solid support at a second end of the spacer molecule.

Immobilisation of a glycan is direct when the linker end of the glycan is attached to the solid support without a spacer molecule, i.e. binding occurs directly between the linker end of the glycan and the solid support.

Preferably the solid support is suitable for immobilising glycans. In some embodiments the solid support is coated with a material capable of binding glycans and/or spacer molecules. In preferred embodiments the solid support is coated with a material capable of forming covalent bonds with glycans and/or spacer molecules. In preferred embodiments the glycans and/or spacer molecules are immobilised on the solid support by covalent bonds between the glycan/spacer molecule and the solid support.

The material coating the solid support may be a matrix comprising a reactive group capable of binding, e.g covalently bonding, a group on the glycan and/or spacer molecule. Most preferably, covalent bonding occurs between amino groups on the glycan and/or spacer molecules and amino groups on the coating of the solid support.

Suitable solid supports for immobilising glycans are well known in the art and include NHS (N-hydroxysuccinimide)-activated glass slides. NHS-activated slides immobilise ligands containing amino groups by covalent attachment of the amino group to the NHS-activated group to form an amide linkage.

Glycan Array

In preferred embodiments the solid support forms part of a glycan array. Glycan arrays are well known in the art; see for example Liang et al 2009. (Expert Rev Proteomics. 2009 December; 6(6):631-45); Blixt et al. 2004 (PNAS 2004 101 (49): pp 17033-17038) the contents of which are hereby incorporated by reference.

A glycan array comprises a solid support on which one or more glycans have been immobilised (e.g. covalently bonded), at separate locations. The glycans may all have the same structure or they may have one or more different structures. Briefly, glycans immobilised on a solid support are contacted with antibody molecules. The solid support is then washed to remove any unbound antibody molecules. Binding between antibody molecules and glycans can then be detected directly or indirectly. Binding between antibody molecules and glycans can be detected directly using a detectable marker or 'tag' (e.g. a fluorescent marker or biotin) coupled to the antibody molecule. Alternatively, binding can be detected indirectly by contacting the bound antibodies with a secondary antibody coupled to a detectable marker.

A preferred glycan array is the printed glycan array provided by the Consortium for Functional Glycomics (www.functionalglycomics.org). The printed array uses a library of natural and/or synthetic glycans printed on to glass microscope slides. One or more candidate antibodies are added to the array in conditions where binding between the glycans and the candidate antibodies may occur. The slides are then washed to remove unbound antibodies. Binding between glycans and antibodies is detected indirectly as follows: The bound antibodies are contacted with secondary antibodies tagged with fluorescent reagents (e.g. Alexa Fluor dyes). Binding between the antibody molecules and secondary antibodies is then detected using a scanner (e.g ProScanArray scanner) to detect emission spectra of the fluorescent reagent.

The glycan array may include at least one positive and at least one negative control. In some embodiments the glycan array may also include at least one background control. The use of positive, negative and background controls in arrays is well known in the art. A negative control is known to give a negative result. The negative control may be a molecule which is known not to bind antibody molecules. Alternatively the negative control may be created by the absence of a glycan bound to the solid support, i.e, so there is nothing for a candidate antibody to bind. The positive control confirms that the basic conditions of the experiment were able to produce a positive result. The positive control may be a molecule, e.g. a glycan, which is known to bind an antibody molecule.

The glycans immobilised on the array preferably have different structures. Preferably some or all of the glycans comprise Fucα1-2Galβ1-3GlcNAc. The glycans used in the array may be linear and/or branched glycans.

Alternative methods for screening glycans, other than printed glycan arrays are also known in the art. For example, ELISA-based microplate arrays.

Core Fucose

In some embodiments the glycans used in methods of the present invention do not contain a core fucose. By core fucose we mean a fucose residue located at or near the linker end of the glycan. The core fucose is distinct from a fucose residue located at the terminal free end of the glycan. In some embodiments the core fucose is a fucose residue located at the linker end of the glycan, i.e the terminal residue at the linker end is a fucose residue. In some embodiments the core fucose is a fucose residue located near, i.e within a few residues, of the terminal residue at the linker end of the glycan. In some embodiments the core fucose is located within one or more of 2, 3, 4, 5, 6, 7, 8, 9, or 10 residues of the linker end of the glycan.

Without being bound by theory we believe that a core fucose can interfere with binding of the glycan to the solid support and/or binding of the glycan to the antibody molecule.

Optionally, the glycans used in methods of the present invention do not include:

Fucα1-2Galβ1-3GlcNAcβ1-2Manα1-3(Fucα1-2Galβ1-3GlcNAcβ1-2Manα1-6)Manβ1-4GlcNAc1-4(Fucα1-6)GlcNAcβ; or,

Fucα1-2Galβ1-3GlcNAcβ1-2Manα1-3(Fucα1-2Galβ1-3GlcNAcβ1-2Manα1-6)Manβ1-4GlcNAcβ1-4(Fucα1-6)GlcNAcβ-Sp22.

Spacer Molecules

Glycans may be indirectly immobilised on the solid support using a spacer molecule. A spacer molecule may be any suitable molecule capable of binding both the glycan and the solid support. Preferably such molecules have an amino group. More preferably such molecules are able to bind the glycan and solid support by forming covalent bonds with the glycan molecule and a suitable solid support.

Such molecules may have a first end capable of binding the glycan, e.g. through covalent bonding and a second end capable of binding the solid support e.g. through covalent bonding. Preferably the spacer molecule may have one or more amino groups.

Preferred spacer molecules are those shown in Table 1. One or more spacers molecule may be used to attach each glycan to the solid support. The spacer molecule is attached to the glycan at the linker end (sometimes annotated as the 'Sp' end). In some embodiments a spacer molecule is not used to attach the glycan to the solid support and the linker end where the glycan is attached directly to the solid support.

Synthetic glycans may be manufactured to incorporate a spacer molecule. Glycans with an incorporated spacer molecule can then be bound to a solid support by the spacer molecule.

TABLE 1

| Code | Spacer molecule |
|------|-----------------|
| Sp0  | —$CH_2CH_2NH_2$ |
| Sp8  | —$CH_2CH_2CH_2NH_2$ |
| Sp9  | —$CH_2CH_2CH_2CH_2CH_2NH_2$ |
| Sp10 | —$NHCOCH_2NH$ |
| Sp11 | —$OCH_2C_6H_4$-p-$NHCOCH_2NH$ |
| Sp12 | Asparagine |
| Sp13 | Glycine |
| Sp14 | Threonine |
| Sp15 | Serine |
| Sp16 | —$PNP(OC_6H_4NH_2)$ |
| Sp17 | —$OCH_2C_6H_4NH_2$ |
| Sp18 | —$O(CH_2)_3NHCO(CH_2)_5NH_2$ |
| Sp19 | EN or NK |
| Sp20 | GENR |

TABLE 1-continued

| Code | Spacer molecule |
| --- | --- |
| Sp21 | —N(CH$_3$)—O—(CH$_2$)$_2$—NH$_2$ |
| Sp22 | NST |
| MDPLys | Mur-L-Ala-D-iGlnb-(CH$_2$)$_4$NH$_2$ |

EN or NK = amino acids Glu (E) and Asn (N), where the glycan is linked to Asn
NST = amino acids Asn (N), Ser (S) and Thr (T), where the glycan is linked to Asn
PNP = p-nitrophenol
GENR = amino acids Gly (G), Glu (E), Asn (N), Arg (R), where the glycan is linked to Asn Measurement of Binding Between Antibody Molecules and Glycans Binding between antibody molecules and glycans may be measured by any suitable method. For example, binding may be measured indirectly or directly, using secondary antibodies or detectable tags as described above. Methods for detecting binding between antibody molecules and glycans are described in Essentials of Glycobiology.

Relative Binding

In some embodiments, methods of the present invention may require the determination of the relative binding between antibody molecules and glycans. The relative binding value is calculated by (a) determining the binding between a first antibody molecule and a glycan; (b) determining the binding between a second antibody molecule and the same glycan; (c) comparing the value of (a) to the value of (b). Preferably the value of (a) is divided by the value of (b) to produce the relative binding value. Alternatively the value of (b) is divided by the value of (a). Alternatively the ratio of binding in (a) and the binding in (b) may be calculated to produce the relative binding value.

As long as the method of calculating the relative binding value is kept constant, then the relative binding value can be used as a comparison of the binding between different antibody molecules and glycans. The relative binding value can be used to compare the binding of the same antibody molecule to different glycans, or to compare the binding of the same glycan to different antibody molecules. In particular the relative binding value can be used to indicate candidate antibody molecules which bind particularly strongly to glycans.

In some embodiments methods may include the step of comparing the relative binding of the glycan and a test antibody molecule to the binding of the glycan and a non-cytotoxic PODXL-binding antibody molecule, e.g. mAb85, and selecting as a candidate an antibody molecule with a relative binding value above a pre-determined value.

Briefly, here the relative binding is calculated by (a) determining binding between the antibody molecule being tested and a glycan; (b) determining binding between the non-cytotoxic PODXL-binding antibody molecule and the same glycan and (c) dividing the value of (a) by the value of (b) to produce the relative binding value.

In some embodiments methods may include the step of comparing the relative binding of the glycan and a test antibody molecule to the binding of the glycan and a cytotoxic PODXL-binding antibody molecule, e.g. mAb84, and selecting as a candidate an antibody molecule with a relative binding value above a pre-determined value.

Briefly, here the relative binding is calculated by (a) determining binding between the antibody molecule being tested and a glycan; (b) determining binding between the cytotoxic PODXL-binding antibody molecule and the same glycan and (c) dividing the value of (a) by the value of (b) to produce the relative binding value.

In some embodiments, the step of determining binding between the non-cytotoxic PODXL-binding antibody molecule and the glycan, or between the cytotoxic PODXL-binding antibody molecule and the glycan, is carried out only once. This value can then be used as a reference, against which the test antibody molecule glycan-binding values can be compared to produce the relative binding value.

In preferred embodiments relative binding is calculated using one or more of the following steps:
  i) contacting the antibody molecule with a glycan comprising Fucα1-2Galβ1-3GlcNAc;
  ii) determining binding between the antibody molecule and the glycan comprising Fucα1-2Galβ1-3GlcNAc;
followed by:
  iii) contacting a non-cytotoxic PODXL-binding molecule with a glycan comprising Fucα1-2Galβ1-3GlcNAc;
  iv) determining binding between the non-cytotoxic PODXL-binding molecule and the glycan comprising Fucα1-2Galβ1-3GlcNAc;
and/or
  v) contacting a cytotoxic PODXL-binding molecule with a glycan comprising Fucα1-2Galβ1-3GlcNAc;
  vi) determining binding between the cytotoxic PODXL-binding molecule and the glycan comprising Fucα1-2Galβ1-3GlcNAc.

In some embodiments the method includes the step of selecting an antibody molecule having a relative binding equal to or greater than that of a cytotoxic PODXL-binding antibody molecule as a candidate cytotoxic antibody molecule.

In some embodiments the method includes the step of selecting an antibody molecule having a relative binding of 30 or more times that of the non-cytotoxic PODXL-binding antibody molecule as a candidate cytotoxic antibody molecule. In some embodiments the antibody molecule selected as a candidate cytotoxic antibody molecule may have a relative binding of 40, 50, 50, 70, 80, 90, 100, 150, 200, 250, 300, 350, 400, 450, 500, 550, 600, 650, 700, 750, 800, 850, 900, 950 or 1000 or more times that of the non-cytotoxic PODXL-binding antibody molecule. In some embodiments the antibody molecule selected as a candidate cytotoxic antibody molecule may have a relative binding of 1500, 2000, 2500, 3000, 3500, 4000, 4500, 5000, 5500, 6000, 6500, 7000, 7500, 8000, 8500, 9000, 9500 or 10000 or more times that of the non-cytotoxic PODXL-binding antibody molecule.

In some embodiments the non-cytotoxic PODXL-binding antibody molecule may be replaced in the method by any antibody with a known binding intensity to a glycan comprising Fucα1-2Galβ1-3GlcNAc. The binding intensity is known if it has been previously measured. Such an antibody is capable of acting as a control against which the binding of candidate antibody molecules to the glycan can be compared. Thus the method includes the step of selecting an antibody molecule having a relative binding of or more times that of the control antibody molecule as a candidate cytotoxic antibody molecule. In some embodiments the antibody molecule selected as a candidate cytotoxic antibody molecule may have a relative binding of 40, 50, 50, 70, 80, 90, 100, 150, 200, 250, 300, 350, 400, 450, 500, 550, 600, 650, 700, 750, 800, 850, 900, 950 or 1000 or more times that of the control antibody molecule. In some embodiments the antibody molecule selected as a candidate cytotoxic antibody molecule may have a relative binding of 1500, 2000, 2500, 3000, 3500, 4000, 4500, 5000, 5500, 6000, 6500, 7000, 7500, 8000, 8500, 9000, 9500 or 10000 or more times that of the control antibody molecule.

Absolute Binding

In some embodiments a calculation of the relative binding is not needed. In such embodiments antibody molecules which bind the glycan most strongly are selected as candidate cytotoxic antibody molecules. Preferably candidate antibody molecules are selected based on the binding between the antibody molecule and a glycan or an array of glycans comprising Fucα1-2Galβ1-3GlcNAc. This is known as the absolute binding value.

In some embodiments candidate antibody molecules are selected from a sample containing such antibody molecules based on their absolute binding value. In preferred embodiments the sample contains more than one different antibody molecule.

In preferred embodiments methods of the present invention comprise selecting an antibody molecule having an absolute binding value in the top 10% of antibody molecules in a sample as a candidate cytotoxic antibody molecule. In other embodiments the top 0.1%, 0.5%, 1%, 2%, 3%, 4%, 5%, 15%, 20%, 25% or 30% of antibody molecules in a sample are selected as candidate cytotoxic antibody molecules.

Binding Affinity

As is commonly known in the art, the strength (of affinity) with which an antibody molecule binds an epitope is called its binding affinity. Affinity can be quantified by determining an association constant, K. Methods for determining the binding affinity between an antibody and an epitope are well known in the art. See, for example, Essentials of Glycobiology[31].

The Kd (dissociation constant) indicates the strength of binding between an antibody (A) and epitope (B) in terms of how easy it is to separate the complex AB. The strength of the binding between A and B will be a balance between AB (antibody bound to epitope) or A and B (antibody not bound to epitope).

This relationship can be written as an equation:

$k1$(rate of dissociation)$AB \dashrightarrow A+B$ $k2$(rate of association)$A+B \dashrightarrow AB$ At equilibrium, $k2[AB]=k1[A][B]$.

This can be rearranged to: $k2/k1=[A][B]/[AB]=Kd$

The smaller the $K_D$ value, the stronger the binding between A and B.

The association constant $K_A$, (sometimes called the affinity constant) is the inverted dissociation constant (reciprocal of $K_D$). The affinity constant is a measure of the affinity of the antibody for the epitope. The larger the $K_A$ value, the stronger the binding between A and B.

Kits

Kits of the present invention may include at least one glycan comprising Fucα1-2Galβ1-3GlcNAc. The kit may include a solid support to which the glycan(s) are attached, as described above.

Kits of the present invention may also include one or more molecules capable of acting as a control molecule. Preferably the molecule provides a positive control, i.e the molecule is known to bind to a glycan comprising Fucα1-2Galβ1-3GlcNAc and so will provide a positive result. An example of a suitable positive control is the mAb 84 antibody. The control molecule can be any molecule which is known to bind a glycan comprising Fucα1-2Galβ1-3GlcNAc with a known binding intensity. By known binding intensity we mean that the binding between the control molecule and the glycan has been established.

Kits may also include one or more non-cytotoxic control molecules. These may be molecules which are known to be non-cytotoxic and to bind glycans comprising Fucα1-2Galβ1-3GlcNAc with a relative binding of less than 500. Alternatively they may bind with a relative binding of less than 400, 300, 200, 100, 50 or 10. By comparing the binding of the non-cytotoxic control molecule and the candidate antibody molecule, antibody molecules can be selected which bind glycans more strongly than a non-cytotoxic control as candidates for having cytotoxic activity against an undifferentiated pluripotent stem cell and/or a cell which expresses PODXL.

An example of a non-cytotoxic control molecule is the mAb85 antibody described in WO 2007/102787.

Kits may also include a further agent that detects binding between the glycan and an antibody molecule. Preferably the further agent is a labelled secondary antibody molecule.

Formulating Pharmaceutically Useful Compositions and Medicaments

Cytotoxic antibody molecules, isolated and/or identified by methods of the present invention may be formulated into pharmaceutically useful compositions. In addition to the steps of the methods described herein, such methods may further comprise:

(a) mixing the antibody or antibodies obtained, identified, selected or produced with a pharmaceutically acceptable carrier, adjuvant or diluent.

Step (a) preferably results in formulation/preparation of a pharmaceutical composition or medicament suitable for therapeutic use.

Symbol and Text Nomenclature for Representation of Glycan Structure

Glycan structures are described and represented using standard IUPAC (International Union of Pure and Applied Chemistry) nomenclature and symbols, see for example Essentials of Glycobiology[31] or Principles of Chemical Nomenclature: a Guide to IUPAC Recommendations[34]. See also www.iupac.org The IUPAC symbol nomenclature as applied to glycans by the Consortium for Functional Glycomics is described below.

Hexoses: Circles
N-Acetylhexosamines: Squares
Hexosamines: Squares divided diagonally
Galactose stereochemistry=yellow with black outline
Glucose stereochemistry=blue with black outline
Mannose stereochemistry=green with black outline
Fucose=red with black outline
Xylose=five pointed star, orange with black outline.

When desired, linkage information can be represented in text next to a line connecting the symbols.

Examples of IUPAC symbol nomenclature are shown in FIG. 1A and FIG. 1B.

IUPAC text nomenclature can be written in either a linear or 2D version. Examples of text nomenclature are shown in FIG. 1B and FIG. 2B.

Definitions

By 'cytotoxic' we mean being toxic to cells, resulting in cell death. Antibodies selected by the method of the present invention may be cytotoxic to any cell which is expressing PODXL and/or an undifferentiated pluripotent stem cell.

By 'cytotoxic antibody molecule' we mean an antibody, or fragment of an antibody, which has cytotoxic activity against an undifferentiated induced pluripotent stem cell.

By 'non-cytotoxic antibody molecule' we mean an antibody, or fragment of an antibody, which does not have cytotoxic activity against an undifferentiated induced pluripotent stem cell.

BRIEF DESCRIPTION OF THE FIGURES

Embodiments and experiments illustrating the principles of the invention will now be discussed with reference to the accompanying figures in which:

FIG. 1A. 2D representation of a typical branched glycan using the IUPAC symbol code. The glycan has been annotated to show the linker end and the two free ends.

FIG. 1B. IUPAC 2D text and linear text code for the glycan shown in FIG. 1A.

FIG. 2A. IUPAC 2D symbol code of a typical linear glycan annotated to show the linker end and free end.

FIG. 2B. IUPAC 2D text code and linear text code for the glycan shown in FIG. 2A.

FIG. 3A. Table of data from version 4.1 of the CFG glycan array tested with mAb84 antibodies. The table has been sorted by average binding to show the glycans which bind mAb84 most strongly at the top. Average=average binding between antibody and glycan. The average is of four replicates. Binding is measured in relative fluorescence units (RFU value). StDev=standard deviation of the mean. SEM=standard error of the mean % CV=100×(StDev/Mean). The CV (coefficient of variation) is a measure of the variation of the results from the mean. The number of each glycan in V4.1 of the array is also shown.

FIG. 4A. Table of data from version 4.1 of the CFG glycan array tested with mAb85 antibodies. The table has been sorted by average binding to show the glycans which bind mAb85 most strongly at the top. Average=average binding between antibody and glycan. The average is of four replicates. Binding is measured in relative fluorescence unity (RFU value). StDev=standard deviation of the mean. SEM=standard error of the mean. % CV=100×(StDev/Mean). The CV (coefficient of variation) is a measure of the variation of the results from the mean. The number of each glycan in V4.1 of the array is also shown.

FIG. 5. Table showing the binding of 9 glycans to mAb84 (column labelled average binding mAb84), mAb85 (column labelled average binding mAb85) and the relative binding of the glycans to mAb84 compared to (divided by) mAb85 (column labelled relative binding). The 9 glycans used in this table are those which bound most strongly to mAb84 in the table shown in FIG. 4 and all contain Fucα1-2Galβ1-3GlcNAc residues.

This table shows that the binding of cytotoxic mAb84 antibodies to these glycans is at least 37 times more than the binding of non-cytotoxic mAb85 antibodies to the same glycans. Therefore the relative binding value may be used to select candidate antibodies.

FIG. 6. Amino acid sequence of 528 amino acid Podocalyxin-like protein 1 precursor (SEQ ID NO: 1).

FIG. 7. Amino acid sequence of human PODXL GenBank accession number O00592.2 GI:229462740 (SEQ ID NO: 2).

FIG. 8. Amino acid sequence of human PODXL GenBank accession number AAI43319.1 GI:219520307 (SEQ ID NO: 3).

Figure 9:

FIG. 9. Amino acid sequence of two PODXL variants (SEQ ID NOs: 8 & 9).

Figure 10:
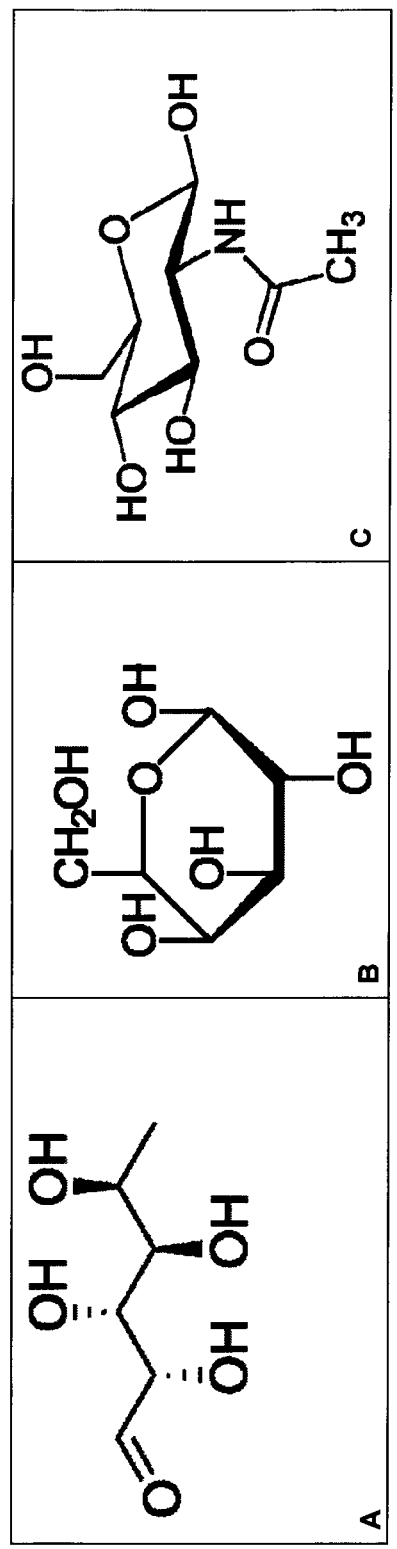

FIG. 10. (A) chemical structure of Fucose (B) chemical structure of Galactose C) chemical structure of N-acetylglucosamine FIG. 11. Amino acid sequence (and encoding polynucleotide sequence) of the $V_L$ chain of mAb 84 (SEQ ID NOs: 4 & 5). Amino acids not underlined correspond to the framework region. The amino acids underlined correspond to the complementarity determining regions (CDRs).

FIG. 12. Amino acid sequence (and encoding polynucleotide sequence) of the $V_H$ chain of mAb 84 (SEQ ID NO: 6 & 7). The amino acids not underlined correspond to the framework region. The amino acids underlined correspond to the CDRs.

Figure 13:
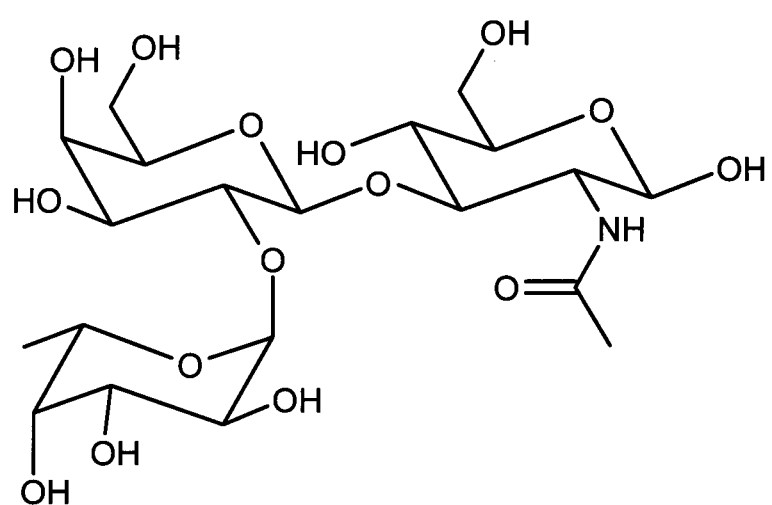

FIG. 13. Chemical structure of Fucα1-2Galβ1-3GlcNAc.

Figure 14:
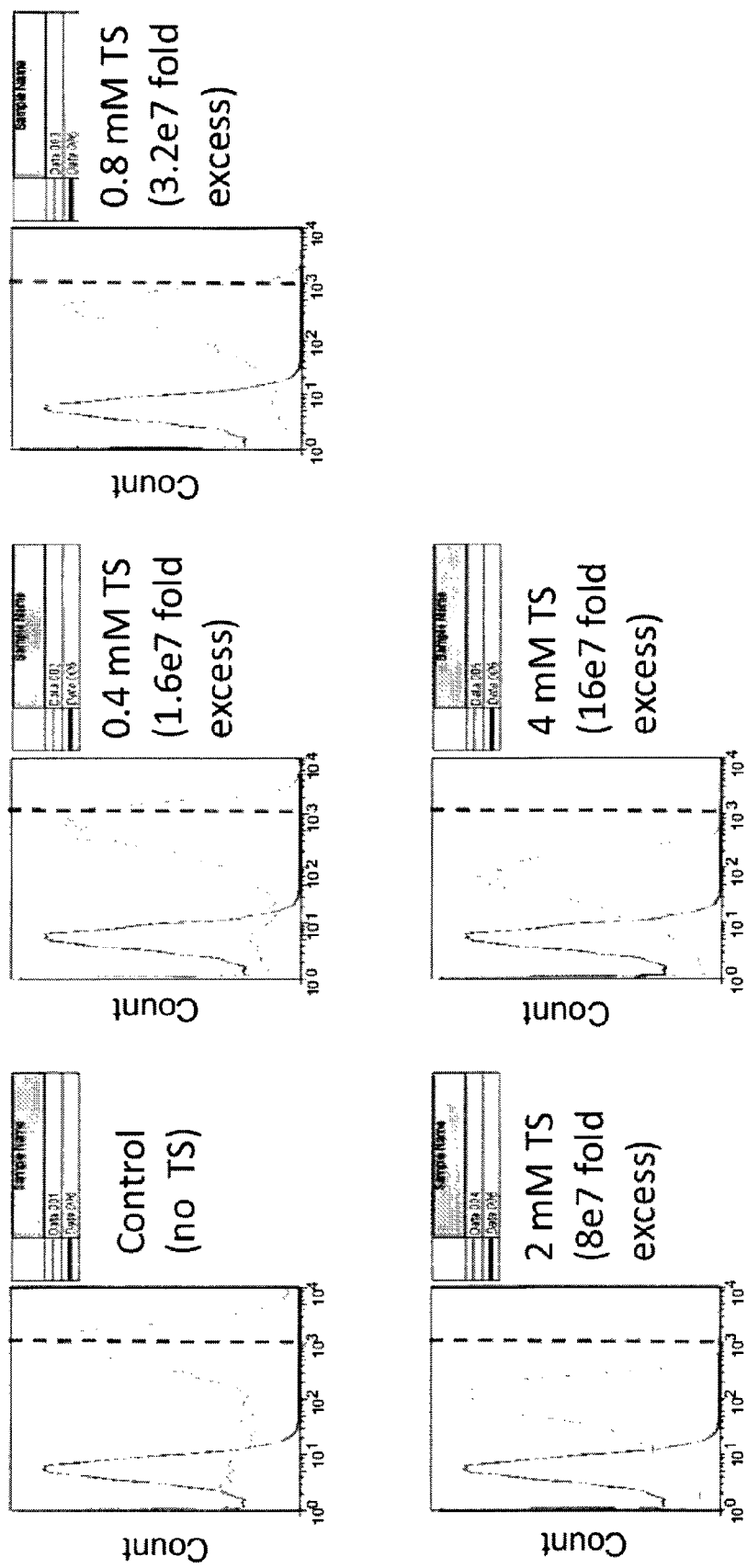

FIG. 14. The trisaccharide Fucα1-2Galβ1-3GlcNAc blocks mAb84 binding human embryonic stem cells (hESC). Green line (right hand line) indicates binding to hESC. Increasing concentrations of the trisaccharide reduce mAb84 binding to hESC as shown by a shift of the peak to the left.

Figure 15:
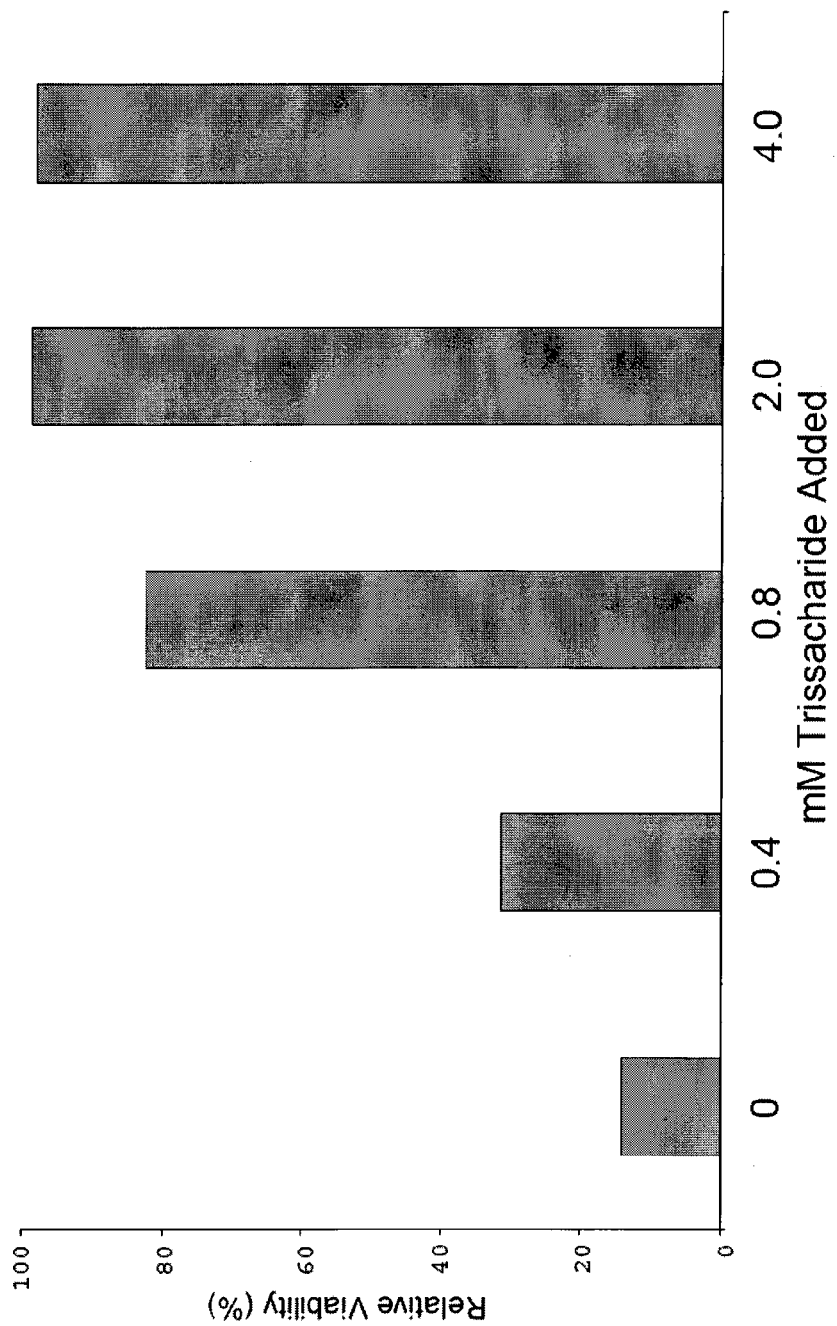

FIG. 15. Graph showing relative viability of hESC in response to mAb84 with addition of increasing concentrations of the trisaccharide Fucα1-2Galβ1-3GlcNAc. Cytotoxicity is reduced and then abolished with increasing concentrations of Fucα1-2Galβ1-3GlcNAc.

EXAMPLES

Materials and Methods
Protocol for Glycan Binding Assay
  Materials needed:
    Glycan printed slides (Core D), printed on the side of the slide with the white etched barcode and black marks—DO NOT TOUCH THIS AREA.
    Cover slips (Fisher scientific, 12-545F)
    Humidified Slide processing chambers (Fisher scientific, NC9091416), or homemade system using Petri Dish, with wet paper towels in the bottom of the chamber
    100 ml Coplin jars for washing slides
    Tris-HCl (Fisher scientific, BP152-1)
    NaCl (Fisher scientific, S271-3)
    $CaCl_2$ (Fisher scientific, C79-500)
    $MgCl_2$ (Fisher scientific, BP214-500)
    Potassium Phosphate Monobasic (Fisher scientific, P285-3)
    $dH_2O$
    Cyanine 5-Streptavidin (ZYMED 43-4316)
    Appropriate secondary antibody, fluorescently labeled if available
    BSA (Fisher scientific, Bp1600-100)
    Tween-20 (EMD Biosciences, 655205)
    Sodium Azide (fisher scientific, S227-500)
    ProScanArray Scanner (Perkin Elmer)
  Buffers:
    TSM=20 mM Tris-HCl, pH 7.4 150 mM NaCl, 2 mM $CaCl_2$, 2 mM $MgCl_2$
    TSM Wash Buffer (TSMW)=TSM Buffer+0.05% Tween-20
    TSM Binding Buffer (TSMBB)=TSM buffer+0.05% Tween 20+1% BSA
  Protocol:
1. Make working stocks of washing buffers (TSM, TSM Wash Buffer, and $H_2O$) or collect reagents and bring to room temperature if they have been in the refrigerator.
   1.1. Buffer (A) TSM-20 mM Tris-HCl, pH 7.4 150 mM NaCl, 2 mM $CaCl_2$, 2 mM $MgCl_2$
   1.2. Buffer (B) TSM Wash Buffer (TSMW)—TSM Buffer+0.05% Tween-20
   1.3. Buffer (C) TSM Binding Buffer (TSMBB)—TSM buffer+0.05% Tween 20+1% BSA
   1.4. $dH_2O$ 2. Prepare 100 μl of sample by diluting antibody in TSMBB or appropriate Binding Buffer based on properties of Antibody to a final concentration of 5-50 μg/ml or an appropriate concentration required for the analysis.

mAb84 antibodies were added at a concentration of 50 μg/ml.

mAb85 antibodies were added at a concentration of 50 μg/ml.

3. Remove slide(s) from dessicator and label slide with sample name near barcode, outside of the black marks.
4. Hydrate the slide by placing in a glass Coplin staining jar containing 100 ml of TSMW for 5 min.
5. Remove excess liquid from slide by setting the slide upright to drain the liquid off.
6. Carefully apply 70 μl of sample close to the left edge slide in between the black marks.
7. Slowly place cover slip on slide, trying to avoid the formation of bubbles in the sample under the cover slip. Remove any bubbles by gently tapping the cover slip with a pipette tip if necessary, or slowly lifting one side of the cover slip. Make sure the cover slip is between the black marks.
8. Incubate slide in a humidified tray in the dark (to preserve fluorescent reagents) for 1 hr at RT.
9. After 1 hr incubation, remove cover slip by gently allowing it to slip off into the glass trash/biohazard trash.
10. Wash the slide by gently dipping 4 times into 100 ml of each of the following buffers in Coplin Jars:
    10.1. TSMW
    10.2. TSM
11. Remove excess water from slide by tipping the slide upright.
12. Add 70 μl of AlexaFluor-488-labeled (or other label) secondary antibody containing 1 μl of Cyanine 5-labeled streptavidin (final concentration 0.5 μg/ml).
13. Cover slip as above (6, 7) and incubate as above (8).
14. After 1 hr incubation, remove cover slip by gently allowing it to slip off into the glass trash/biohazard trash.
15. Wash the slide by gently dipping 4 times into 100 ml of each of the following buffers in Coplin Jars:
    15.1. TSMW
    15.2. TSM
    15.3. dH$_2$O
16. Spin slide in slide centrifuge for ~15 seconds or remove water under a gentle stream of nitrogen.
17. Scan.

See also: www.functionalglycomics.org

Figure 3B:
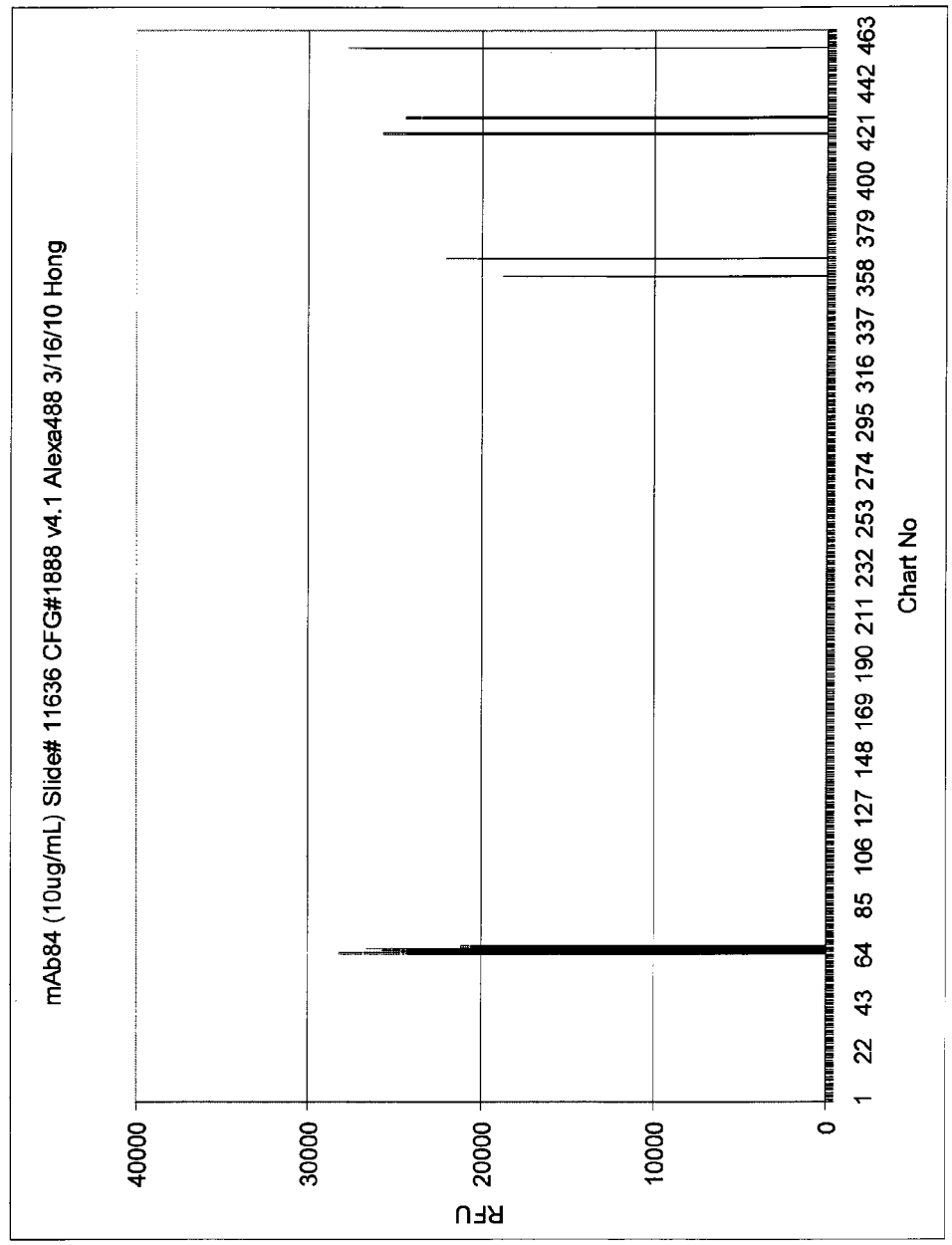
FIG. 3B. Graph summarising the results in FIG. 3A. The number of each glycan is shown along the X axis (labelled in FIG. 3B as 'Chart No'). These correspond to the glycan numbers in FIG. 3A. The binding between each glycan and mAb84 is shown on the Y axis. Binding is measured in relative fluorescence units ('RFU').
Figure 4B:
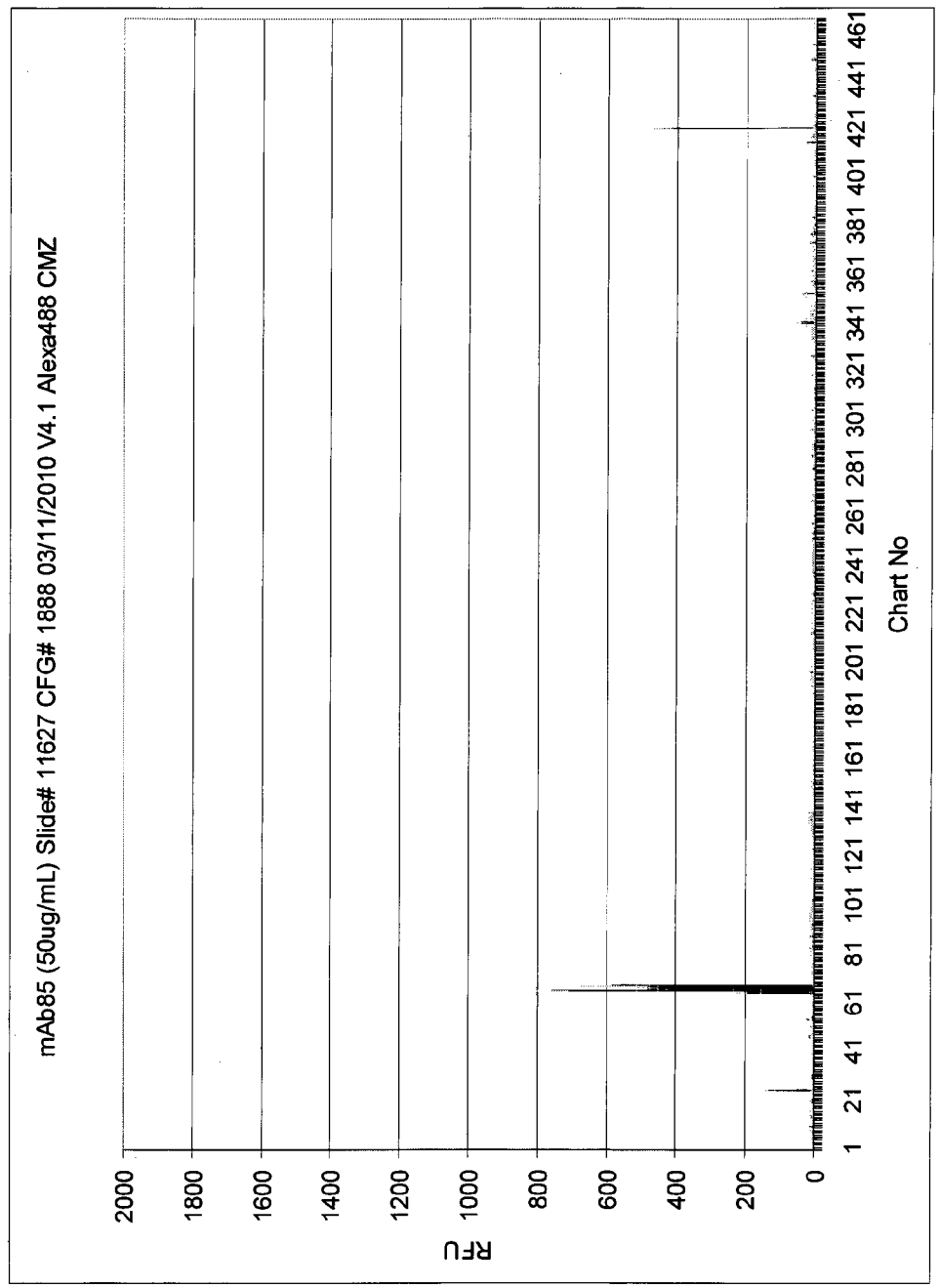
FIG. 4B. Graph summarising the results in FIG. 4. The number of each glycan is shown along the X axis (labelled in FIG. 4B as 'Chart No'). These correspond to the glycan numbers in FIG. 4A. The binding between each glycan and mAb85 is shown on the Y axis. Binding is measured in relative fluorescence units ('RFU').

Glycan Array mAb84 and mAb85 antibodies were sent to the Consortium for Functional Glycomics for testing in accordance with the protocol described above. Version 4.1 of a printed glycan array was used. Version 4.1 contains 465 glycans printed onto glass slides in replicates of six. The full list of 465 glycans is shown in FIGS. 3 and 4. The list is also available from the CFG website at: www.functionalglycomics.org. Further details of the printed glycan array are also described in Blixt et al (2004)[32].

mAb84 antibodies were contacted with the glycans. The slide was washed to remove unbound antibodies. Bound antibodies were detected using AlexaFluor-488-labeled secondary antibodies as described above. The secondary antibodies were then detected using a fluorescence scanner. Binding is presented in relative fluorescence units (RFU). A higher RFU value indicates that glycans were bound with the higher intensity.

Six replicates were used; the highest and lowest points from each set of six replicates were removed so that the average is of four replicates. This eliminates some of the false hits that contain a single very high or low point.

Example 1

The inventors have discovered that mAb 84 does not bind to:

unglycosylated PODXL (in vitro transcription and translation (TnT))

PODXL over-expressed in HEK and COS cells

The gene encoding PODXL was isolated and sequenced from hESC. The gene was cloned into vectors and expressed either unglycosylated (in vitro TnT) or in mammalian cells (HEK or COS cells which are capable of glycosylating the expressed protein).

The proteins obtained were then resolved on SDS-PAGE, Western blotted and probed with antibodies. The antibodies used were commercially available anti-PODXL antibodies (monoclonal and polyclonal) and mAb 84. For in vitro TnT-expressed PODXL, it was found that only the polyclonal anti-PODXL detected a band of ~55 kDa which corresponds to the molecular weight (MW) of unglycosylated PODXL. Monoclocal anti-PODXL and mAb84 did not detect the unglycosylated PODXL. For COS and HEK expressed PODXL, only monoclonal anti-PODXL detected both the expressed PODXL and PODXL from hESC.

In either COS or HEK cells, PODXL is glycosylated (and so has a higher MW). However the band is lower than PODXL expressed in hESC (HES-3). Also, mAb 84 only detected hESC—PODXL but not expressed PODXL. This led to the conclusion that there is a stem cell-specific modification (glycosylation) to PODXL. Without being bound by theory, it appears that when PODXL is glycosylated by stem cells the resulting glycan structure is different that of PODXL glycosylated by other cells.

Example 2

Cytotoxic mAb84 antibodies selectively bind to glycans comprising Fucα1-2Galβ1-3GlcNAc residues in a glycan array.

The cytotoxic antibody mAb84 was tested for binding with 465 different glycans in V4.1 of the Printed Glycan Array (Consortium for Functional Glycomics) using the protocol described above.

Briefly, antibodies were diluted 1:100 to 10 μg/ml in binding buffer contacted with the glycan array and detected with Alexa488 labeled anti-mouse IgM (Invitrogen, A21042). The array was washed to remove unbound antibodies. The array was contacted with a labelled secondary antibody, which was able to bind to mAb84 antibodies. The labelled secondary antibody was then detected and quantified. mAb84 antibodies were found to selectively bind to glycans containing Fucα1-2Galβ1-3GlcNAc residues. Without being bound by theory, we believe that the mAb84 antibody is specific for the Fucα1-2Galβ1-3GlcNAc residues in these glycans.

The full list of glycans tested for binding with mAb84, and the binding of mAb84 to these glycans is shown in FIG. 3.

Example 3

Non-cytotoxic mAb85 antibodies have the same glycan specificity as mAb84, but a much lower affinity for these glycans.

Non-cytotoxic mAb85 antibodies were tested for binding with 465 glycans in V4.1 of the Printed Glycan Array (Consortium for Functional Glycomics) using the protocol described above. This was the same type of array used to test mAb84 antibodies as described in Example 3. mAb85 antibodies were found to bind similar glycans to mAb84 antibodies. In particular, mAb85 bound to glycans comprising Fucα1-2Galβ1-3GlcNAc. However, binding between mAb85 and glycans comprising Fucα1-2Galβ1-3GlcNAc was found to be significantly lower than the binding between cytotoxic mAb84 to the same glycans.

The full list of glycans tested for binding with mAb85, and the binding of mAb85 to these glycans is shown in FIG. 4.

Example 4

The binding values of mAb84 and mAb85 to glycans comprising Fucα1-2Galβ1-3GlcNAc were compared to generate the relative binding value for each glycan. Specifically, the absolute binding value for each glycan bound by mAb84 was divided by the corresponding absolute binding value for the same glycan bound to mAb85. The results are presented in FIG. 5.

The results show that although glycans comprising Fucα1-2Galβ1-3GlcNAc are bound by both cytotoxic (mAb84) and non-cytotoxic (mAb85) antibodies, cytotoxic antibodies have a stronger affinity for these glycans and bind them more strongly. The relative binding value shows that cytotoxic mAb84 antibodies bind glycans at least 37 times more strongly than non-cytotoxic mAb85 antibodies.

Example 5

The importance of the trisaccharide Fucα1-2Galβ1-3GlcNA in mediating the cytotoxic interaction of mAb84 on human embryonic stem cells (hESC) was investigated by assessing the ability of synthetic soluble trisaccharide Fucα1-2Galβ1-3GlcNA to (i) inhibit the binding of mAb84 to hESC and (ii) reduce the cytotoxic effect of mAb84 on hESC.

mAb84 (25 pM, 5 μg) in 200 μl volume was added to 2×10$^5$ hESC and preincubated for 15 minutes prior to addition of synthetic soluble trisaccharide Fucα1-2Galβ1-3GlcN (in concentrations of 0 (control), 0.4 mM, 0.8 mM, 2 mM, 4 mM).

Increasing concentrations of the trisaccharide Fucα1-2Galβ1-3GlcNAc were shown to dose dependently inhibit mAb84 binding to hESC (FIG. 14). In FIG. 14 the right hand line indicates binding to hESC, and increasing concentrations of the trisaccharide reduce mAb84 binding to hESC as shown by a shift of the peak to the left.

Relative viability of hESC in response to increasing concentrations of the trisaccharide Fucα1-2Galβ1-3GlcNA was also assessed. FIG. 15 shows a reduction of the cytotoxic effect of mAb84 with increasing concentrations of Fucα1-2Galβ1-3GlcNAc (concentrations of 0 (control), 0.4 mM, 0.8 mM, 2 mM, 4 mM). The cytotoxic effect was abolished at concentrations of 2 mM and 4 mM.

This data shows that binding of mAb84 to hESC and the cytotoxic effect of mAb84 on hESC are mediated by the trisaccharide Fucα1-2Galβ1-3GlcNA.

References

1. Choo et al (2008). Selection Against Undifferentiated Human Embryonic Stem Cells By A Cytotoxic Antibody Recognizing Podocalyxin-like Protein-1. Stem Cells 26(6):1454-63.
2. Takahashi et al (2007) Induction of Pluripotent Stem Cells from Adult Human Fibroblasts by Defined Factors. Cell 131(5):861-72.
3. Yu et al (2007) Induced Pluripotent Stem Cell Lines Derived from Human Somatic Cells. Science 318(5858): 1917-20.
4. Choo et al (2004) Expansion of pluripotent human embryonic stem cells on human feeders. Biotechnology and .Bioengineering 88:321-331.
5. Brandenberger et al (2004) Transcriptome characterization elucidates signaling networks that control human ES cell growth an differentiation. Nature Biotechnology 22:707-716
6. Cai et al (2006) Assessing self-renewal and differentiation in human embryonic stem cell limes. Stem cells 24:516-530
7. Cai et al (2005) Development of antibodies to human embryonic stem cell antigens. BMC Dev Biol 5:26
8. Wei et al (2005) Transcriptome profiling of human and murine ESCs identifies divergent paths required to maintain the stem cell state. Stem Cells 23:166-185
9. Schopperle et al. (2007) The TRA-1-60 and TRA-1-81 human pluripotent stem cell markers are expressed on podocalyxin in embryonal carcinoma. Stem cells 25:723-730.
10. Yamanaka et al (2009) A Fresh Look at iPS Cells. Cell 137: 13-17
11. Okita et al (2007) Generation of germline-competent induced pluripotent stem cells. Nature 448:313-318.
12. Chung Y, Klimanskaya I, Becker S, et al. Embryonic and extraembryonic stem cell lines derived from single mouse blastomeres. Nature. 2006; 439:216-219.
13. Chung Y, Klimanskaya I, Becker S, et al. Human embryonic stem cell lines generated without embryo destruction. Cell Stem Cell. 2008; 2:113-117.
14. Jiang, Y., Jahagirdar, B. N., Reinhardt, R. L., Schwartz, R. E., Keene, C. D., Ortiz-Gonzalez, X. R., Reyes, M., Lenvik, T., Lund, T., Blackstad, M., et al. (2002). Pluripotency of mesenchymal stem cells derived from adult marrow. Nature 418, 41-49.
15. Kaji et al. Virus-free induction of pluripotency and subsequent excision of reprogramming factors. Nature. Online publication 1 Mar. 2009.
16. Kanatsu-Shinohara, M., Inoue, K., Lee, J., Yoshimoto, M., Ogonuki, N., Miki, H., Baba, S., Kato, T., Kazuki, Y., Toyokuni, S., et al. (2004). Generation of pluripotent stem cells from neonatal mouse testis. Cell 119, 1001-1012.
17. Kershaw et al (1997) J. Biol. Chem. 272, 15708-15714.
18. Kim et al. Ex vivo characteristics of human amniotic membrane-derived stem cells. Cloning Stem Cells 2007 Winter; 9(4):581-94.
19. Lin et al. Multilineage potential of homozygous stem cells derived from metaphase II oocytes. Stem Cells. 2003; 21(2):152-61.
20. Lei et al Xeno-free derivation and culture of human embryonic stem cells: current status, problems and challenges. Cell Research (2007) 17:682-688.
21. Maherali N, et. al. Directly reprogrammed fibroblasts show global epigenetic remodeling and widespread tissue contribution. Cell Stem Cell 2007; 1:55-70.
22. Matsui, Y., Zsebo, K., and Hogan, B. L. (1992). Derivation of pluripotential embryonic stem cells from murine primordial germ cells in culture. Cell 70, 841-847.
23. Takahashi K, Tanabe K, Ohnuki M, Narita M, Ichisaka T, Tomoda K, Yamanaka S. (2007). Induction of pluripotent stem cells from adult human fibroblasts by defined factors. Cell. 131(5):861-72.

24. Takahashi, K. & Yamanaka, S. Induction of pluripotent stem cells from mouse embryonic and adult fibroblast cultures by defined factors. Cell 2006; 126:663-676.
25. Wernig M, et. al. In vitro reprogramming of fibroblasts into a pluripotent ES-cell-like state. Nature 2007; 448:318-24.
26. Yamanaka S, et. al. Generation of germline-competent induced pluripotent stem cells. Nature 2007; 448:313-7.
27. Yu J, Vodyanik M A, Smuga-Otto K, Antosiewicz-Bourget J, Frane J L, Tian S, Nie J, Jonsdottir G A, Ruotti V, Stewart R, Slukvin II, Thomson J A. Induced pluripotent stem cell lines derived from human somatic cells. Science. 318(5858):1917-20. Epub 2007 Nov. 20.
28. Zhang X, Stojkovic P, Przyborski S, et al. Derivation of human embryonic stem cells from developing and arrested embryos. Stem Cells 2006; 24:2669-2676.
29. H. L. Tan et al. (2009) mAb 84, a cytotoxic antibody that kills undifferentiated human embryonic stem cells via oncosis. Stem Cells 27 (8):1792-1801.
30. A. Pluckthun & P. Pack. (1997) New protein engineering approaches to multivalent and bispecific antibody fragments. Immunotechnology. 3 (2):83-105.
31. Varki. A, Cummings. R, Esko. J, Freeze. H, Hart. G & Marth, J. Eds. Essentials of Glycobiology $2^{nd}$ Edition. Cold Spring Harbor Laboratory Press.
32. Blixt. O, Head. S, Mondala, T. Scanlan. C. Huflejt, M E. Alvarez. R, Bryan. MC, Fazio. F, Lacarese. D, Stevens. J, Razi. N, Stevens. D J, Skehel. J J, van Die. I, Burton. D R, Wilson, I A, Cummings. R, Bovin. N, Wong. C H, Paulson. J C. Printed covalent glycan array for ligand profiling of diverse glycan binding proteins. PNAS (2004) vol. 101 no.49 pages 17033-17038.
33. Petsko, G A & Ringe D. Protein structure and function (2004) New Science Press.
34. Principles of Chemical Nomenclature: a Guide to IUPAC Recommendations Leigh, G. J.; Favre, H. A. & Metanomski, W. V. Blackwell Science, (1998)

The invention claimed is:

1. A method of selecting an antibody molecule as a candidate for having cytotoxic activity against a cell which expresses podocalyxin-like protein (PODXL), or is an undifferentiated pluripotent stem cell, wherein the antibody molecule binds PODXL, the method comprising the steps of:
 (i) comparing the binding of a PODXL-binding antibody molecule to a glycan comprising Fucα1-2Galβ1-3GlcNAc with the binding of a non-cytotoxic PODXL-binding antibody molecule to a glycan comprising Fucα1-2Galβ1-3GlcNAc; and
 (ii) selecting as a candidate cytotoxic antibody molecule a said PODXL-binding antibody molecule that has a relative binding to said glycan of 30 or more times greater than said non-cytotoxic PODXL-binding antibody molecule.

2. The method of claim 1, wherein the glycan consists of a glycan selected from the group:
 Fucα1-2Galβ1-3GlcNAcβ1-3Galβ1-4Glcβ;
 Neu5Acα2-6Galβ1-4GlcNAcβ1-6(Fucα1-2Galβ1-3GlcNAcβ1-3)Galβ-4Glc;
 Fucα1-2Galβ1-3GlcNAcβ;

Fucα1-2Galβ1-3GlcNAcβ1-3GalNAc;
Fucα1-2Galβ1-3GlcNAcβ1-3(Galβ1-4GlcNAcβ1-6)
   Galβ1-4Glc;
Fucα1-2Galβ1-3GlcNAcβ1-3(Galβ1-4(Fucα1-3)
   GlcNAcβ1-6)Galβ1-4Glc;
Fucα1-2Galβ1-3GlcNAc; or
Fucα1-2Galβ1-3GlcNAcβ1-2Manα1-3(Fucα1-2Galβ1-
   3GlcNAcβ1-2Manα1-6)Manβ1-4GlcNAcβ1-
   4GlcNAcβ.

3. The method of claim 1, further comprising:
(iii) testing the candidate antibody for cytotoxic activity against a cell which expresses PODXL or is an differentiated pulripotent stem cell.

4. The method of claim 1, wherein said relative binding is 100 or more times, 500 or more times, 1000 or more times, or 10000 or more times greater than said non-cytotoxic PODXL-binding antibody molecule.

5. A method of selecting an antibody molecule as a candidate for having cytotoxic activity against an undifferentiated pluripotent stem cell, or as a candidate for binding PODXL and having cytotoxic activity against a cell which expresses PODXL, the method comprising the steps of:
(i) comparing the binding of a PODXL-binding antibody molecule to a glycan comprising Fucα1-2Galβ1-3GlcNAc with the binding of a non-cytotoxic PODXL-binding antibody molecule to a glycan comprising Fucα1-2Galβ1-3GlcNAc; and
(ii) selecting as a candidate cytotoxic antibody molecule a said PODXL-binding antibody molecule that has a relative binding to said glycan of 30 or more times greater than said non-cytotoxic PODXL-binding antibody molecule.

6. The method of claim 5, further comprising:
(iii) testing the candidate antibody for cytotoxic activity against an undifferentiated pluripotent stem cell or for PODXL binding and/or having cytotoxic activity against a cell which expresses PODXL.

7. The method of claim 5, wherein the relative binding is 100 or more times, 500 or more times, 1000 or more times, or 10000 or more times greater than said non-cytotoxic PODXL-binding antibody molecule.

8. A method of selecting an antibody molecule as a candidate for binding PODXL and/or for having cytotoxic activity against a cell which expresses PODXL or is an undifferentiated stem cell, the method comprising selecting an antibody molecule which binds a glycan comprising Fucα1-2Galβ1-3GlcNAc.

9. The method of any one of claim 5, wherein the glycan consists of a glycan selected from the group:
Fucα1-2Galβ1-3GlcNAcβ1-3Galβ1-4Glcβ;
Neu5Acα2-6Galβ1-4GlcNAcβ1-6(Fucα1-2Galβ1-
   3GlcNAcβ1-3)Galβ-4Glc;
Fucα1-2Galβ1-3GlcNAcβ;
Fucα1-2Galβ1-3GlcNAcβ1-3GalNAc;
Fucα1-2Galβ1-3GlcNAcβ1-3(Galβ1-4GlcNAcβ1-6)
   Galβ1-4Glc;
Fucα1-2Galβ1-3GlcNAcβ1-3(Galβ1-4(Fucα1-3)
   GlcNAcβ1-6)Galβ1-4Glc;
Fucα1-2Galβ1-3GlcNAcβ; or
Fucα1-2Galβ1-3GlcNAcβ1-2Manα1-3(Fucα1-2Galβ1-
   3GlcNAcβ1-2Manα1-6)Manβ1-4GlcNAcβ1-
   4GlcNAcβ.

10. The method of claim 5, wherein the glycan consists of a glycan selected from the group:
Fucα1-2Galβ1-3GlcNAcβ1-3Galβ1-4Glcβ-Sp8;
Neu5Acα2-6Galβ1-4GlcNAcβ1-6(Fucα1-2Galβ1-
   3GlcNAcβ1-3)Galβ-4Glc-Sp21;
Fucα1-2Galβ1-3GlcNAcβ-Sp0;
Fucα1-2Galβ1-3GlcNAcβ1-3Galβ1-4Glcβ-Sp10;
Fucα1-2Galβ1-3GlcNAcβ1-3GalNAc-Sp14;
Fucα1-2Galβ1-3GlcNAcβ1-3(Galβ1-4GlcNAcβ1-6)
   Galβ1-4Glc-Sp21;
Fucα1-2Galβ1-3GlcNAcβ1-3(Galβ1-4(Fucα1-3)
   GlcNAcβ1-6)Galβ1-4Glc-Sp21;
Fucα1-2Galβ1-3GlcNAcβ-Sp8; or
Fucα1-2Galβ1-3GlcNAcβ1-2Manα1-3(Fucα1-2Galβ1-
   3GlcNAcβ1-2Manα1-6)Manβ1-4GlcNAcβ1-
   4GlcNAcβ-Sp20.

11. A kit of parts comprising:
(a) a glycan comprising Fucα1-2Galβ1-3GlcNAc;
(b) an agent that detects binding between the glycan and an antibody molecule; and
(c) a non-cytotoxic control molecule which binds the glycan.

12. A method of selecting an antibody molecule, from a sample containing such molecules, as a candidate for having cytotoxic activity against an undifferentiated pluripotent stem cell, wherein the antibody molecule binds PODXL, the method comprising the steps of:
i) contacting the sample of antibody molecules with a plurality of glycans comprising Fucα1-2Galβ1-3GcNAc;
ii) selecting an antibody molecule having an absolute binding to at least one said glycan in the top 10% as a candidate cytotoxic antibody molecule.

13. A method of selecting an antibody molecule as a candidate for having cytotoxic activity against an undifferentiated pluripotent stem cell or a cell which expresses podocalyxin-like protein (PODXL), wherein the antibody molecule binds PODXL, the method comprising the steps of:
(i) measuring the binding of a PODXL-binding antibody molecule to a glycan comprising Fucα1-2Galβ1-3GlcNAc; and
(ii) selecting as a candidate cytotoxic antibody molecule a said PODXL-binding antibody molecule that has a binding to said glycan equal to or greater than that of a cytotoxic PODXL-binding antibody molecule.

14. The method of claim 12 further comprising:
(iii) testing the candidate antibody for cytotoxic activity against an undifferentiated pluripotent stem cell or a cell that expresses PODXL.

15. A method of selecting an antibody molecule as a candidate for having cytotoxic activity against a cell which expresses podocalyxin-like protein (PODXL) or against an undifferentiated pluripotent stem cell, wherein the antibody molecule binds PODXL, the method comprising the steps of:
(i) comparing the binding of a PODXL-binding antibody molecule to a glycan comprising Fucα1-2Galβ1-3GlcNAc with the binding of a cytotoxic PODXL-binding antibody molecule to a glycan comprising Fucα1-2Galβ1-3GlcNAc; and
(ii) selecting as a candidate cytotoxic antibody molecule a said PODXL-binding antibody molecule that has a binding to said glycan equal to or greater than that of the said cytotoxic PODXL-binding antibody molecule.

16. The method of claim 15, further comprising:
(iii) testing the candidate antibody for cytotoxic activity against a cell which expresses PODXL.

17. The use of any one of claim 12, wherein the glycan consists of a glycan selected from the group:
Fucα1-2Galβ1-3GlcNAcβ1-3Galβ1-4Glcβ;
Neu5Acα2-6Galβ1-4GlcNAcβ1-6(Fucα1-2Galβ1-
   3GlcNAcβ1-3)Galβ-4Glc;
Fucα1-2Galβ1-3GlcNAcβ;

Fucα1-2Galβ1-3GlcNAcβ1-3GalNAc;
Fucα1-2Galβ1-3GlcNAcβ1-3(Galβ1-4GlcNAcβ1-6)
  Galβ1-4Glc;
Fucα1-2Galβ1-3GlcNAcβ1-3(Galβ1-4(Fucα1-3)
  GlcNAcβ1-6)Galβ1-4Glc;
Fucα1-2Galβ1-3GlcNAcβ; or
Fucα1-2Galβ1-3GlcNAcβ1-2Manα1-3(Fucα1-2Galβ1-
  3GlcNAcβ1-2Manα1-6)Manβ1-4GlcNAcβ1-
  4GlcNAcβ.

18. The method of claim 12 wherein the glycan consists of a glycan selected from the group:
Fucα1-2Galβ1-3GlcNAcβ1-3Galβ1-4Glcβ-Sp8;
Neu5Acα2-6Galβ1-4GlcNAcβ1-6(Fucα1-2Galβ1-
  3GlcNAcβ1-3)Galβ-4Glc-Sp21;
Fucα1-2Galβ1-3GlcNAcβ-Sp0;
Fucα1-2Galβ1-3GlcNAcβ1-3Galβ1-4Glcβ-Sp10;
Fucα1-2Galβ1-3GlcNAcβ1-3GalNAc-Sp14;
Fucα1-2Galβ1-3GlcNAcβ1-3(Galβ1-4GlcNAcβ1-6)
  Galβ1-4Glc-Sp21;
Fucα1-2Galβ1-3GlcNAcβ1-3(Galβ1-4(Fucα1-3)
  GlcNAcβ1-6)Galβ1-4Glc-Sp21;
Fucα1-2Galβ1-3GlcNAcβ-Sp8; or
Fucα1-2Galβ1-3GlcNAcβ1-2Manα1-3(Fucα1-2Galβ1-
  3GlcNAcβ1-2Manα1-6)Manβ1-4GlcNAcβ1-
  4GlcNAcβ-Sp20.

19. The method of claim 6 wherein the relative binding is 100 or more times, 500 or more times, 1000 or more times, or 10000 or more times greater than said non-cytotoxic PODXL-binding antibody molecule.

20. The method of claim 13 further comprising:
(iii) testing the candidate antibody for cytotoxic activity against an undifferentiated pluripotent stem cell or a cell that expresses PODXL.

21. The method of claim 13, wherein the glycan consists of a glycan selected from the group:
Fucα1-2Galβ1-3GlcNAcβ1-3Galβ1-4Glcβ;
Neu5Acα2-6Galβ1-4GlcNAcβ1-6(Fucα1-2Galβ1-
  3GlcNAcβ1-3)Galβ-4Glc;
Fucα1-2Galβ1-3GlcNAcβ;
Fucα1-2Galβ1-3GlcNAcβ1-3GalNAc;
Fucα1-2Galβ1-3GlcNAcβ1-3(Galβ1-4GlcNAcβ1-6)
  Galβ1-4Glc;
Fucα1-2Galβ1-3GlcNAcβ1-3(Galβ1-4(Fucα1-3)
  GlcNAcβ1-6)Galβ1-4Glc;
Fucα1-2Galβ1-3GlcNAcβ; or
Fucα1-2Galβ1-3GlcNAcβ1-2Manα1-3(Fucα1-2Galβ1-
  3GlcNAcβ1-2Manα1-6)Manβ1-4GlcNAcβ1-
  4GlcNAcβ.

22. The method of claim 13, wherein the glycan consists of a glycan selected from the group:
Fucα1-2Galβ1-3GlcNAcβ1-3Galβ1-4Glcβ-Sp8;
Neu5Acα2-6Galβ1-4GlcNAcβ1-6(Fucα1-2Galβ1-
  3GlcNAcβ1-3)Galβ-4Glc-Sp21;
Fucα1-2Galβ1-3GlcNAcβ-Sp0;
Fucα1-2Galβ1-3GlcNAcβ1-3Galβ1-4Glcβ-Sp10;
Fucα1-2Galβ1-3GlcNAcβ1-3GalNAc-Sp14;
Fucα1-2Galβ1-3GlcNAcβ1-3(Galβ1-4GlcNAcβ1-6)
  Galβ1-4Glc-Sp21;
Fucα1-2Galβ1-3GlcNAcβ1-3(Galβ1-4(Fucα1-3)
  GlcNAcβ1-6)Galβ1-4Glc-Sp21;
Fucα1-2Galβ1-3GlcNAcβ-Sp8; or
Fucα1-2Galβ1-3GlcNAcβ1-2Manα1-3(Fucα1-2Galβ1-
  3GlcNAcβ1-2Manα1-6)Manβ1-4GlcNAcβ1-
  4GlcNAcβ-Sp20.

\* \* \* \* \*